(12) United States Patent
Zhang et al.

(10) Patent No.: US 11,548,900 B2
(45) Date of Patent: Jan. 10, 2023

(54) OXAZINO-QUINAZOLINE AND OXAZINO-QUINOLINE TYPE COMPOUND, PREPARATION METHOD AND USES THEREOF

(71) Applicant: BEIJING SCITECH-MQ PHARMACEUTICALS LIMITED, Beijing (CN)

(72) Inventors: Qiang Zhang, Beijing (CN); Shannan Yu, Beijing (CN); Zhongxiang Wang, Beijing (CN); Shouye Feng, Beijing (CN); Nanqiao Zheng, Beijing (CN); Hailong Yang, Beijing (CN); Leifu Yang, Beijing (CN); Hongbo Zhang, Beijing (CN); Likai Zhou, Beijing (CN); Zhanqiang Xu, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 163 days.

(21) Appl. No.: 16/978,158

(22) PCT Filed: Mar. 5, 2019

(86) PCT No.: PCT/CN2019/077028
§ 371 (c)(1),
(2) Date: Sep. 3, 2020

(87) PCT Pub. No.: WO2019/170088
PCT Pub. Date: Sep. 12, 2019

(65) Prior Publication Data
US 2021/0040114 A1 Feb. 11, 2021

(30) Foreign Application Priority Data
Mar. 6, 2018 (CN) .......................... 201810182708.1

(51) Int. Cl.
| | | |
|---|---|---|
| C07D 498/04 | (2006.01) |
| C07D 519/00 | (2006.01) |
| A61K 31/5383 | (2006.01) |
| A61P 1/00 | (2006.01) |
| A61P 1/16 | (2006.01) |
| A61P 9/10 | (2006.01) |
| A61P 11/00 | (2006.01) |
| A61P 17/00 | (2006.01) |
| A61P 17/06 | (2006.01) |
| A61P 17/14 | (2006.01) |
| A61P 19/02 | (2006.01) |
| A61P 19/08 | (2006.01) |
| A61P 27/02 | (2006.01) |
| A61P 35/00 | (2006.01) |
| A61P 35/02 | (2006.01) |
| A61P 37/00 | (2006.01) |
| A61P 37/02 | (2006.01) |
| A61P 37/06 | (2006.01) |

(52) U.S. Cl.
CPC ......... *C07D 498/04* (2013.01); *C07D 519/00* (2013.01)

(58) Field of Classification Search
CPC ............... C07D 498/04; C07D 519/00; A61K 31/5383; A61P 1/00; A61P 1/16; A61P 9/10; A61P 11/00; A61P 17/00; A61P 17/06; A61P 17/14; A61P 19/02; A61P 19/08; A61P 27/02; A61P 35/00; A61P 35/02; A61P 37/00; A61P 37/02; A61P 37/06
See application file for complete search history.

(56) References Cited

PUBLICATIONS

Segovia-Mendoza, M., "Efficacy and mechanism of action of the tyrosine kinase inhibitors gefitinib, lapatinib and neratinib in the treatment of HER2-positive breast cancer: preclinical and clinical evidence." American journal of cancer research 5.9 (2015): 2531.*

* cited by examiner

*Primary Examiner* — John M Mauro
(74) *Attorney, Agent, or Firm* — McCarter & English, LLP; Xin Zhang; Xiaoyuan Ding

(57) ABSTRACT

Provided are an oxazino-quinazoline and oxazino-quinoline type compound, a preparation method, and uses thereof. More particularly provided is a compound shown in formula (I), an isomer, a hydrate, a solvate, a pharmaceutically acceptable salt, a prodrug thereof, a preparation method, and uses thereof in preparing a drug acting as a kinase inhibitor.

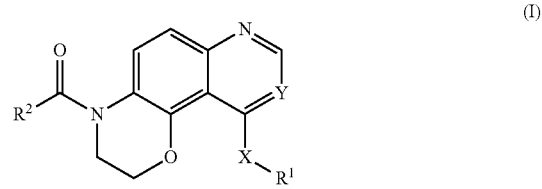

(I)

22 Claims, No Drawings

OXAZINO-QUINAZOLINE AND OXAZINO-QUINOLINE TYPE COMPOUND, PREPARATION METHOD AND USES THEREOF

CROSS REFERENCE TO RELATED APPLICATIONS

The present application is a 35 U.S.C. § 371 national stage application of International Application No. PCT/CN2019/077028 filed on Mar. 5, 2019, which claims the priority of the Chinese Patent Application No. 201810182708.1 filed on Mar. 6, 2018. The entire contents of each of aforementioned applications are expressly incorporated herein by reference as part of the disclosure of the present application.

TECHNICAL FIELD

The present disclosure belongs to the technical field of medicinal chemistry and specifically relates to an oxazino-quinazoline and oxazino-quinoline compound, preparation method thereof and application thereof.

BACKGROUND OF THE INVENTION

Protein kinase is an important signal messenger of cell life activity, which can catalyze the transfer of γ-phosphate group at the terminal of the ATP to the hydroxyl receptor in the amino acid residues (serine, threonine, tyrosine) of the substrate, thereby activating the target protein (Johnson L. N., and Lewis R. J., (2001) Structural basis for control by phosphorylation. Cheminform. 101, 2209). Protein kinases are involved in many physiological processes, including cell proliferation, survival, apoptosis, metabolism, transcription, and differentiation (Adams J. A., (2001) Kinetic and catalytic mechanisms of protein kinases. Chemical reviews. 101, 2271). Among the existing drug targets in the human body, members of the protein kinase family account for up to 10% (Santos R., Ursu O., Gaulton A., et al. (2017) A comprehensive map of molecular drug targets. Nature Reviews Drug Discovery. 16, 19).

Epidermal growth factor receptor (ErbB) tyrosine kinase can regulate cell proliferation, migration, differentiation, apoptosis, and cell movement through a variety of pathways. In many forms of malignant tumors, members of the ErbB family and part of their ligands are often overexpressed, amplified, or mutated, which makes them become important therapeutic targets. The family of protein kinases includes: ErbB1/EGFR/HER1, ErbB2/HER2, ErbB3/HER3 and ErbB4/HER4. Wherein, EGFR and HER2 are important targets for the development of non-small cell lung cancer and breast cancer drugs (Dienstmann R., et. al., (2001) Personalizing Therapy with Targeted Agents in Non-Small Cell Lung Cancer. ONCOTARGET. 2(3), 165; Mitri Z., et. al. (2012) The HER2 Receptor in Breast Cancer: Pathophysiology, Clinical Use, and New Advances in Therapy, Chemotherapy Research & Practice, Volume 2012 (23), 743193). In addition, in terms of structural characteristics, EGFR and HER2 are highly conserved in the intracellular tyrosine kinase structural region (ATP pocket) containing catalytically active sites. Therefore, EGFR and HER2 kinase inhibitors that are already marketed and under research often have similar chemical structures.

The kinase inhibitors Gefitinib, Erlotinib, and Icotinib target EGFR for the treatment of non-small cell carcinoma. Afatinib, Lapatinib and Neratinib target HER2 and EGFR, wherein Afatinib is used to treat non-small cell carcinoma, Lapatinib and Neratinib are used to treat breast cancer. These kinase inhibitors all contain a quinazoline or quinoline core, and a hydrophobic aromatic substituent is introduced at the 4-position connected through the heteroatoms.

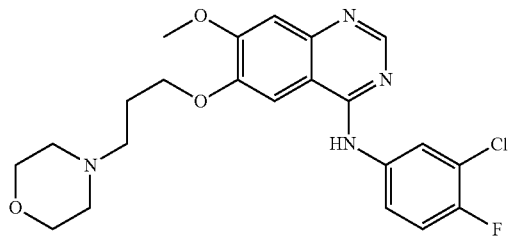

Gefitinib

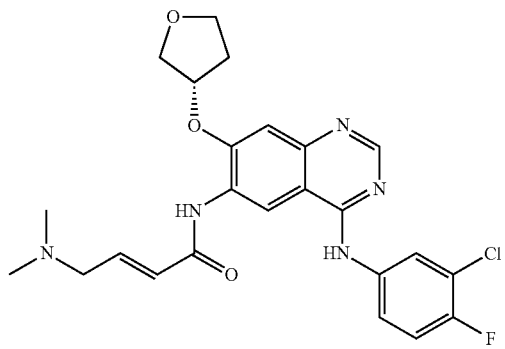

Afatinib

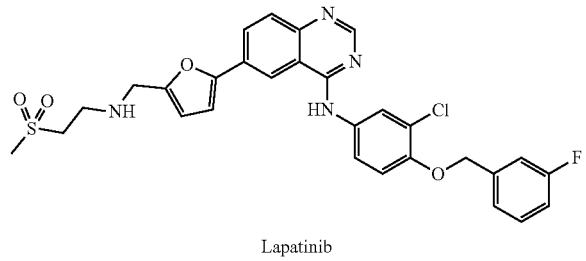

Lapatinib

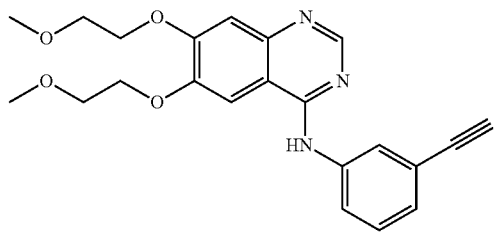

Erlotinib

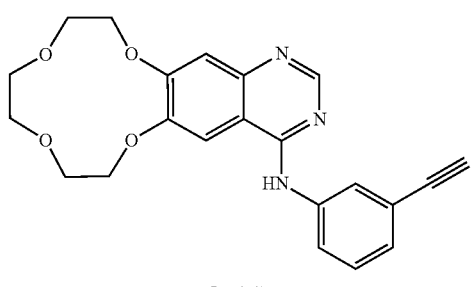

Icotinib

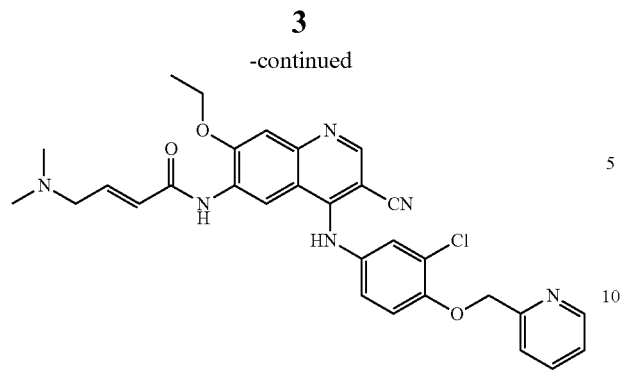

Neratinib

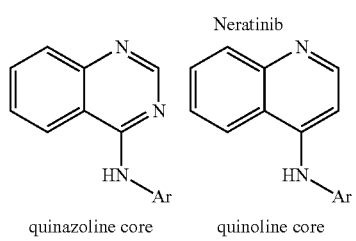

quinazoline core    quinoline core

The above-mentioned marketed kinase inhibitor drugs generally have shortcomings such as drug resistance and severe toxic side effects. In particular, Lapatinib and Neratinib produce serious gastrointestinal side effects after administration, including emesis and diarrhea. Therefore, there is urgent need to develop new HER2 and EGFR kinase inhibitor drugs. Structure-based drug design strategies can discover new active molecules with better efficacy, drug metabolism and drug toxicology, and the development of new active molecules with novel core structures can often facilitate the discovery of a whole series of new drug molecules.

SUMMARY OF THE INVENTION

The present disclosure provides a compound represented by formula (I), or isomers, hydrates, solvates, pharmaceutically acceptable salts or prodrugs thereof, Formula (I)

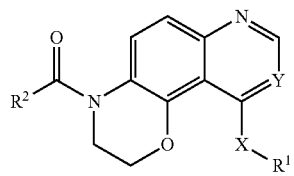

in the formula (I),
X is O, or NH;
Y is N or C—Z, wherein, Z is —H or —CN;
$R^1$ is

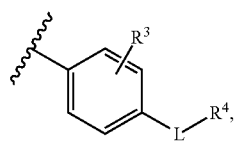

$R^3$ is —H, halogen, $C_1$-$C_3$ alkyl, $C_1$-$C_3$ alkoxy, $C_1$-$C_3$ alkyl substituted by halogen, or $C_1$-$C_3$ alkoxy substituted by halogen;

L is

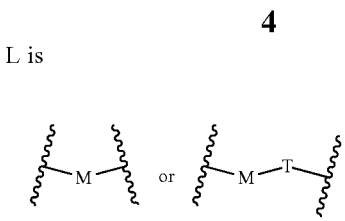

M is O or S;

T is linear $C_1$-$C_3$ alkyl, or linear $C_1$-$C_3$ alkyl independently substituted by $R^5$ and $R^6$, respectively;

$R^5$ and $R^6$ are independently —H, halogen, $C_1$-$C_3$ alkyl, or $C_1$-$C_3$ alkyl substituted by halogen;

$R^4$ is aryl, 5- to 6-membered heteroaryl, aryl substituted by 1-3 identical or different $R^7$, or 5- to 6-membered heteroaryl substituted by 1-3 identical or different $R^7$, wherein the heteroaryl group is a heteroaryl group containing 1-3 heteroatoms selected from N, O or S;

$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl;

$R^2$ is

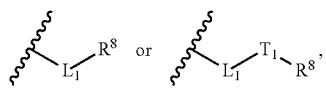

$L_1$ is selected from

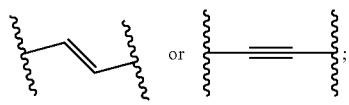

$T_1$ is linear $C_1$-$C_8$ alkyl, or linear $C_1$-$C_8$ alkyl independently substituted by $R^9$ and $R^{10}$, respectively;

$R^9$ and $R^{10}$ are each independently —H, or $C_1$-$C_3$ alkyl;

$R^8$ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —$NR^{11}R^{12}$;

$R^{11}$ and $R^{12}$ are each independently —H, $C_1$-$C_6$ alkyl, $C_3$-$C_6$ cycloalkyl, $C_1$-$C_6$ alkyl substituted by hydroxy, or $C_1$-$C_6$ alkyl substituted by $C_1$-$C_3$ alkoxy;

the 4- to 7-membered heterocyclyl is a heterocyclyl containing 1-2 heteroatoms selected from N, O or S, the heterocyclyl is unsubstituted or substituted by one or two of the group consisting of: $C_1$-$C_3$ alkyl, aldehyde group, $C_1$-$C_4$ alkylacyl, aminoacyl, aminoacyl wherein the amino is substituted with mono- or di-$C_1$-$C_3$ alkyl, $C_1$-$C_3$ alkylsulfonyl, and $C_1$-$C_3$ alkylsulfinyl, or the sulfur in the heterocycle is oxidized by one to two oxygen atoms.

In one alternative embodiment,
$R^1$ is

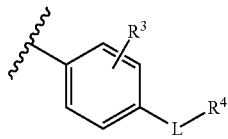

$R^3$ is —H, fluorine, chlorine, bromine, methyl, ethyl, methoxy, ethoxy, trifluoromethyl or trifluoromethoxy;

L is

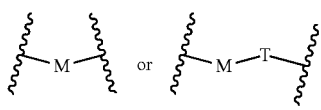

M is O or S;

T is linear $C_1$-$C_2$ alkyl, or linear $C_1$-$C_2$ alkyl independently substituted by $R^5$ and $R^6$, respectively;

$R^5$ and $R^6$ are each independently is —H, —F, methyl, ethyl or trifluoromethyl;

$R^4$ is aryl, 5- to 6-membered heteroaryl, aryl substituted by 1-2 identical or different $R^7$, or 5- to 6-membered heteroaryl substituted by 1-2 identical or different $R^7$, wherein the aryl or heteroaryl group is selected from the group consisting of: phenyl, pyridyl, pyrimidinyl, thiazolyl, thienyl, pyrrolyl, thiadiazolyl, furyl, oxazolyl or isoxazolyl;

$R^7$ is —H, —F, —Cl, —Br, —$CF_3$, —$OCF_3$, amino, hydroxy, cyano, methylthio, ethylthio, propylthio, isopropylthio, methylamino, ethylamino, dimethylamino, diethylamino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methylaminoethoxy, methylaminopropoxy, ethylaminoethoxy, ethylaminopropoxy, dimethylaminoethoxy, dimethylaminopropoxy, diethylaminoethoxy, or diethylaminopropoxy.

In another alternative embodiment,
$R^2$ is

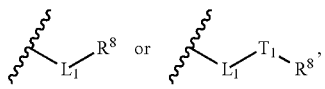

$L_1$ is selected from:

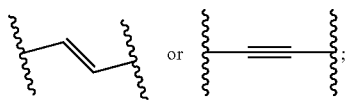

$T_1$ is linear $C_1$-$C_6$ alkyl, or linear $C_1$-$C_6$ alkyl independently substituted by $R^9$ and $R^{10}$, respectively;

$R^9$ and $R^{10}$ are independently —H or methyl;

$R^8$ is —H, hydroxy, methyl, ethyl, propyl, isopropyl, cyclopropyl, cyclobutyl, cyclopentyl, cyclohexyl, methoxy, ethoxy, propoxy, isopropoxy, methylthio, ethylthio, propylthio, isopropylthio, 5- to 6-membered heterocyclyl or —$NR^{11}R^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, cyclohexyl, hydroxyethyl, hydroxypropyl, hydroxybutyl, hydroxypentyl, hydroxyhexyl, methoxyethyl, methoxypropyl, methoxybutyl, methoxypentyl, methoxyhexyl, ethoxyethyl, ethoxypropyl, ethoxybutyl, ethoxypentyl, ethoxyhexyl, propoxyethyl, propoxypropyl, propoxybutyl, propoxypentyl, propoxyhexyl, isopropoxyethyl, isopropoxypropyl, isopropoxybutyl, isopropoxypentyl or isopropoxyhexyl;

the 5- to 6-membered heterocyclyl is a heterocyclyl containing 1-2 heteroatoms selected from N, O or S, the 5- to 6-membered heterocyclyl is unsubstituted or substituted by one or two of the group consisting of: methyl, ethyl, propyl, isopropyl, aldehyde group, formyl, acetyl, propionyl, butyryl, isobutyryl, aminoacyl, methylaminoacyl, dimethylaminoacyl, methylsulfonyl, ethylsulfonyl, isopropylsulfonyl, methylsulfinyl, ethylsulfinyl, and isopropylsulfinyl, or sulfur in the heterocycle is oxidized by one to two oxygen atoms;

the 5- to 6-membered heterocycle is selected from:

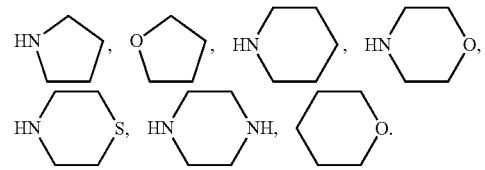

Alternatively,
$R^2$ is

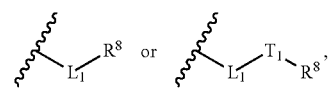

$L_1$ is selected from:

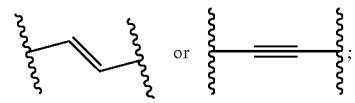

$T_1$ is linear $C_1$-$C_6$ alkyl, or linear $C_1$-$C_6$ alkyl independently substituted by $R^9$ and $R^{10}$, respectively;

$R^9$ and $R^{10}$ are each independently —H or methyl;

$R^8$ is —H, hydroxy, methyl, ethyl, propyl, isopropyl, methoxy, ethoxy, propoxy, isopropoxy, methylthio, ethylthio, propylthio, isopropylthio, cyclopropyl, cyclobutyl, cyclopentyl, cyclohexyl, 5- to 6-membered heterocyclyl or —$NR^{11}R^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, hydroxyethyl, hydroxypropyl, hydroxybutyl, hydroxypentyl, methoxyethyl, methoxypropyl, methoxybutyl, methoxypentyl, ethoxyethyl, ethoxypropyl, ethoxybutyl, ethoxypentyl, propoxyethyl, propoxypropyl, propoxybutyl, propoxypentyl, isopropoxyethyl, isopropoxypropyl, isopropoxybutyl or isopropoxypentyl;

the 5- to 6-membered heterocyclyl is a heterocyclyl containing 1-2 heteroatoms selected from N, O or S, the 5- to 6-membered heterocyclyl is unsubstituted or substituted by one or two of the group consisting of: methyl, ethyl, propyl, isopropyl, aldehyde group, formyl, acetyl, propionyl, butyryl, isobutyryl, aminoacyl, methylaminoacyl, dimethylaminoacyl, methylsulfonyl, ethylsulfonyl, isopropylsulfonyl, methylsulfinyl, ethylsulfinyl, and isopropylsulfinyl, or the sulfur in the heterocycle is oxidized by one to two oxygen atoms;

the 5- to 6-membered heterocyclyl is selected from:

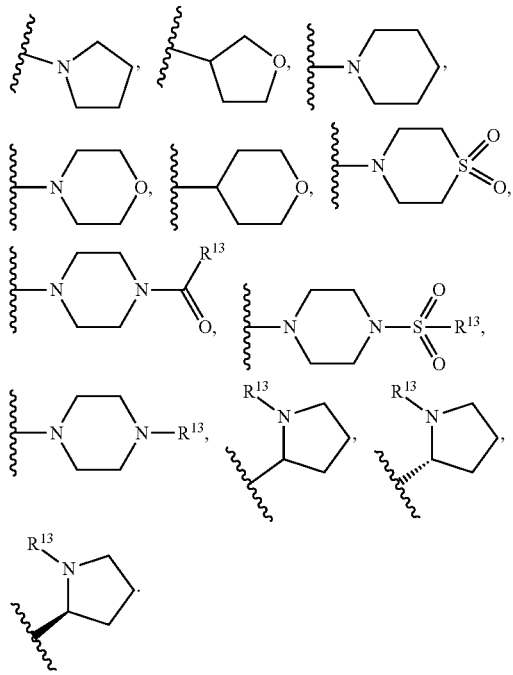

$R^{13}$ is —H, amino, methylamino, dimethylamino, methyl, ethyl, propyl, or isopropyl.

According to another aspect of the present disclosure, a compound of formula (I), or isomers, hydrates, solvates, pharmaceutically acceptable salts and prodrugs thereof are provided, Formula (I)

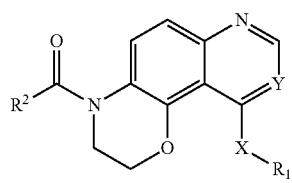

in the formula (I),
X is O, or NH;
Y is N or C—Z, wherein Z is —H or —CN, alternatively, Y is N;

$R^1$ is

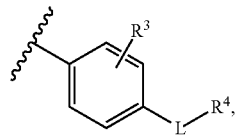

$R^3$ is —H, halogen, $C_1$-$C_3$ alkyl, $C_1$-$C_3$ alkoxy, $C_1$-$C_3$ alkyl substituted by halogen or $C_1$-$C_3$alkoxy substituted by halogen; alternatively, $R^3$ is —H, fluorine, chlorine, bromine, methyl, ethyl, methoxy, ethoxy, trifluoromethyl or trifluoromethoxy;

L is

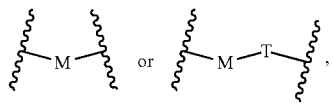

M is O or S;
T is linear $C_1$-$C_3$ alkyl, or linear $C_1$-$C_3$ alkyl independently substituted by $R^5$ and $R^6$, respectively; alternatively, T is linear $C_1$-$C_2$ alkyl, or linear $C_1$-$C_2$ alkyl independently substituted by $R^5$, and $R^6$, respectively;

$R^5$ and $R^6$ are each —H, halogen, $C_1$-$C_3$ alkyl, or $C_1$-$C_3$ alkyl substituted by halogen; alternatively, $R^5$ are $R^6$ are each —H, —F, methyl, ethyl or trifluoromethyl;

$R^4$ is substituted or unsubstituted fused heteroaryl, wherein the substituted fused heteroaryl is substituted by 1-3 identical or different $R^7$, the fused ring heteroaryl group is a heteroaryl group containing 1-3 heteroatoms selected from N, O or S; alternatively, $R^4$ is

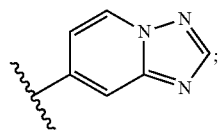 [SMILES: *c1ccn2ncnc2c1]

$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl; alternatively, $R^7$ is —H, —F, —Cl, —Br, —CF$_3$, —OCF$_3$, amino, hydroxy, cyano, methylthio, ethylthio, propylthio, isopropylthio, methylamino, ethylamino, dimethylamino, diethylamino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methoxyethoxy, methylaminopropoxy, ethylaminoethoxy, ethylaminopropoxy, dimethylaminoethoxy, dimethylaminopropoxy, diethylaminoethoxy, or diethylaminopropoxy;

alternatively, $R^1$ is

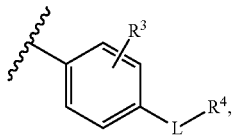

$R^3$ is —H, fluorine, chlorine, bromine, methyl, ethyl, methoxy, ethoxy, trifluoromethyl or trifluoromethoxy;

L is

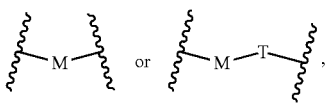

M is O or S;

T is linear $C_1$-$C_2$ alkyl, or linear $C_1$-$C_2$ alkyl independently substituted by $R^5$ and $R^6$, respectively;

$R^5$ and $R^6$ are each independently —H, —F, methyl, ethyl or trifluoromethyl;

$R^4$ is unsubstituted or substituted

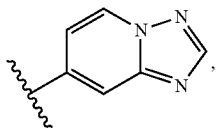 [SMILES: *c1ccn2ncnc2c1]

wherein the group is substituted by 1-3 identical or different $R^7$, $R^7$ is —H, —F, —Cl, —Br, —$CF_3$, —$OCF_3$, amino, hydroxy, cyano, methylthio, ethylthio, propylthio, isopropylthio, methylamino, ethylamino, dimethylamino, diethylamino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methylaminoethoxy, methylaminopropoxy, ethylaminoethoxy, ethylaminopropoxy, dimethylaminoethoxy, dimethylaminopropoxy, diethylaminoethoxy, or diethylaminopropoxy.

$R^2$ is

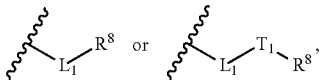

$L_1$ is selected from:

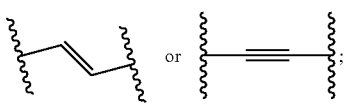

$T_1$ is linear $C_1$-$C_8$ alkyl, or linear $C_1$-$C_8$ alkyl independently substituted by $R^9$ and $R^{10}$, respectively;

$R^9$ and $R^{10}$ are each independently —H, or $C_1$-$C_3$ alkyl;

$R^8$ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —$NR^{11}R^{12}$;

$R^{11}$ and $R^{12}$ are each independently —H, $C_1$-$C_6$ alkyl, $C_3$-$C_6$ cycloalkyl, $C_1$-$C_6$ alkyl substituted by hydroxy or $C_1$-$C_6$ alkyl substituted by $C_1$-$C_3$ alkoxy;

the 4- to 7-membered heterocyclyl is a heterocyclyl containing 1-2 heteroatoms selected from N, O or S, the heterocyclyl is unsubstituted or substituted by any one or two of the group consisting of: $C_1$-$C_3$ alkyl, aldehyde group, $C_1$-$C_4$ alkylacyl, aminoacyl, aminoacyl wherein the amino is substituted with mono- or di-$C_1$-$C_3$ alkyl, $C_1$-$C_3$ alkylsulfonyl, $C_1$-$C_3$ alkylsulfinyl, hydroxy, halogen, $C_1$-$C_3$ hydroxyalkyl, and $C_1$-$C_3$ haloalkyl, or the sulfur in the heterocycle is oxidized by one to two oxygen atoms.

alternatively, $R^2$ is

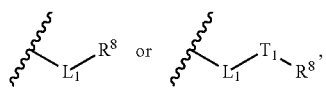

$L_1$ is selected from:

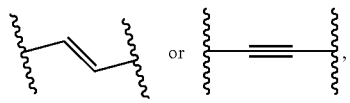

$T_1$ is linear $C_1$-$C_6$ alkyl, or linear $C_1$-$C_6$ alkyl independently substituted by $R^9$ and $R^{10}$, respectively;

$R^9$ and $R^{10}$ are each independently —H or methyl;

$R^8$ is —H, hydroxy, methyl, ethyl, propyl, isopropyl, cyclopropyl, cyclobutyl, cyclopentyl, cyclohexyl, methoxy, ethoxy, propoxy, isopropoxy, methylthio, ethylthio, propylthio, isopropylthio, 5- to 6-membered heterocyclyl or —$NR^{11}R^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, cyclohexyl, hydroxyethyl, hydroxypropyl, hydroxybutyl, hydroxypentyl, hydroxyhexyl, methoxyethyl, methoxypropyl, methoxybutyl, methoxypentyl, methoxyhexyl, ethoxyethyl, ethoxypropyl, ethoxybutyl, ethoxypentyl, ethoxyhexyl, propoxyethyl, propoxypropyl, propoxybutyl, propoxypentyl, propoxyhexyl, isopropoxyethyl, isopropoxypropyl, isopropoxybutyl, isopropoxypentyl or isopropoxyhexyl;

the 5- to 6-membered heterocyclyl is a heterocyclyl containing 1-2 heteroatoms selected from N, O or S, the 5- to 6-membered heterocyclyl is unsubstituted or substituted by any one or two from the group consisting of: methyl, ethyl, propyl, isopropyl, aldehyde group, formyl, acetyl, propionyl, butyryl, isobutyryl, aminoacyl, methylaminoacyl, dimethylaminoacyl, methylsulfonyl, ethylsulfonyl, isopropylsulfonyl, methylsulfinyl, ethylsulfinyl, isopropylsulfinyl, hydroxy, fluorine, chlorine, hydroxymethyl, hydroxyethyl, hydroxypropyl, and trifluoromethyl, or the sulfur in the heterocycle is oxidized by one to two oxygen atoms;

the 5- to 6-membered heterocycle is selected from:

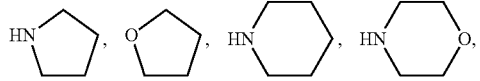

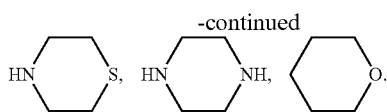

Alternatively, $R^2$ is

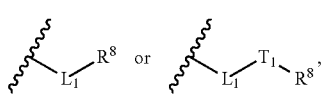

$L_1$ is selected from:

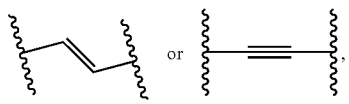

$T_1$ is linear $C_1$-$C_6$ alkyl, or linear $C_1$-$C_6$ alkyl independently substituted by $R^9$ and $R^{10}$, respectively;

$R^9$ and $R^{10}$ are each independently —H or methyl;

$R^8$ is —H, hydroxy, methyl, ethyl, propyl, isopropyl, methoxy, ethoxy, propoxy, isopropoxy, methylthio, ethylthio, propylthio, isopropylthio, cyclopropyl, cyclobutyl, cyclopentyl, cyclohexyl, 5- to 6-membered heterocyclyl or —$NR^{11}R^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, hydroxyethyl, hydroxypropyl, hydroxybutyl, hydroxypentyl, methoxyethyl, methoxypropyl, methoxybutyl, methoxypentyl, ethoxyethyl, ethoxypropyl, ethoxybutyl, ethoxypentyl, propoxyethyl, propoxypropyl, propoxybutyl, propoxypentyl, isopropoxyethyl, isopropoxypropyl, isopropoxybutyl or isopropoxypentyl;

the 5- to 6-membered heterocyclyl is a heterocyclyl containing 1-2 heteroatoms selected from N, O or S, wherein the 5- to 6-membered heterocyclyl is unsubstituted or substituted by any one or two of the group consisting of: methyl, ethyl, propyl, isopropyl, aldehyde group, formyl, acetyl, propionyl, butyryl, isobutyryl, aminoacyl, methylaminoacyl, dimethylaminoacyl, methylsulfonyl, ethylsulfonyl, isopropylsulfonyl, methylsulfinyl, ethylsulfinyl, isopropylsulfinyl, hydroxy, fluorine, chlorine, hydroxymethyl, hydroxyethyl, and trifluoromethyl, or the sulfur in the heterocycle is oxidized by one to two oxygen atoms;

the 5- to 6-membered heterocyclyl is selected from:

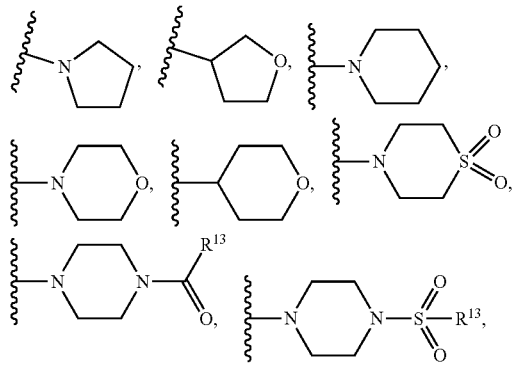

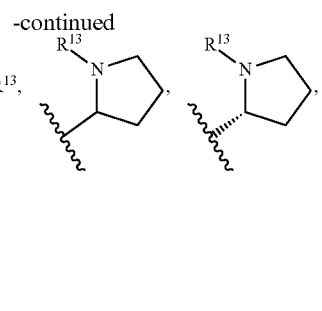

$R^{13}$ is —H, amino, methylamino, dimethylamino, methyl, ethyl, propyl or isopropyl.

According to yet another aspect of the present invention, a compound of formula (I), or isomers, hydrates, solvates, pharmaceutically acceptable salts and prodrugs thereof are provided.

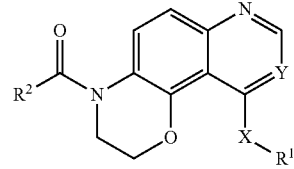

Formula (I)

in the formula (I),

X is O, or NH;

Y is N or C—Z, wherein Z is —H or —CN;

$R^1$ is

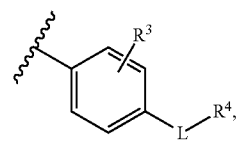

$R^3$ is —H, halogen, $C_1$-$C_3$ alkyl, $C_1$-$C_3$ alkoxy, $C_1$-$C_3$ alkyl substituted by halogen or $C_1$-$C_3$ alkoxy substituted by halogen;

L is

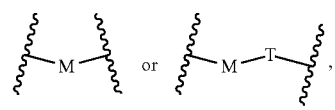

M is O or S;

T is linear $C_1$-$C_3$ alkyl, or linear $C_1$-$C_3$ alkyl independently substituted by $R^5$ and $R^6$, respectively;

$R^5$ and $R^6$ are each independently —H, halogen, $C_1$-$C_3$ alkyl, or $C_1$-$C_3$ alkyl substituted by halogen;

$R^4$ is aryl, 5- to 6-membered heteroaryl, aryl substituted by 1-3 identical or different $R^7$, or 5- to 6-membered heteroaryl substituted by 1-3 identical or different $R^7$, wherein the heteroaryl group is a heteroaryl group containing 1-3 heteroatoms selected from N, O or S;

$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl;

$R^2$ is

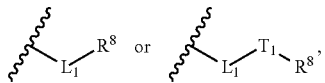

$L_1$ is selected from:

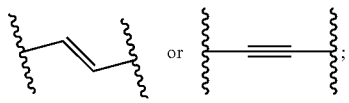

$T_1$ is linear $C_1$-$C_8$ alkyl, or linear $C_1$-$C_8$ alkyl independently substituted by $R^9$ and $R^{10}$, respectively;

$R^9$ and $R^{10}$ are each independently —H, or $C_1$-$C_3$ alkyl;

$R^8$ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —$NR^{11}R^{12}$;

R and $R^{12}$ are each independently —H, $C_1$-$C_6$ alkyl, $C_3$-$C_6$ cycloalkyl, $C_1$-$C_6$ alkyl substituted by hydroxyl or $C_1$-$C_6$ alkyl substituted by $C_1$-$C_3$ alkoxy;

the 4- to 7-membered heterocyclyl is a heterocyclyl containing 1-2 heteroatoms selected from N, O or S, the heterocyclyl is unsubstituted or substituted by any one or two of the group consisting of: $C_1$-$C_3$ alkyl, hydroxy, halogen, $C_1$-$C_3$ hydroxyalkyl, and $C_1$-$C_3$ haloalkyl.

In one alternative embodiment, X is O, or NH, Y is N;

$R^1$ is

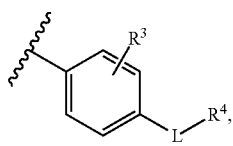

$R^3$ is —H, fluorine, chlorine, bromine, methyl, ethyl, methoxy, ethoxy, trifluoromethyl or trifluoromethoxy;

L is or

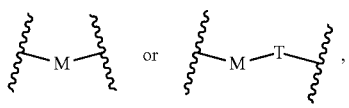

M is O or S;

T is linear $C_1$-$C_2$ alkyl, or linear $C_1$-$C_2$ alkyl independently substituted by $R^5$ and $R^6$, respectively;

$R^5$ and $R^6$ are each independently —H, —F, methyl, ethyl or trifluoromethyl;

$R^4$ is aryl, 5- to 6-membered heteroaryl, aryl substituted by 1-2 identical or different $R^7$, or 5- to 6-membered heteroaryl substituted by 1-2 identical or different $R^7$, wherein the aryl or heteroaryl group is selected from the group consisting of: phenyl, pyridyl, pyrimidinyl, thiazolyl, thienyl, pyrrolyl, thiadiazolyl, furyl, oxazolyl or isoxazolyl;

$R^7$ is —H, —F, —Cl, —Br, —$CF_3$, —$OCF_3$, amino, hydroxy, cyano, methylthio, ethylthio, propylthio, isopropylthio, methylamino, ethylamino, dimethylamino, diethylamino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methylaminoethoxy, methylaminopropoxy, ethylaminoethoxy, ethylaminopropoxy, dimethylaminoethoxy, dimethylaminopropoxy, diethylaminoethoxy, or diethylaminopropoxy.

In another alternative embodiment, $R^2$ is

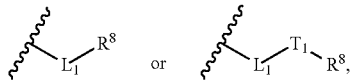

$L_1$ is selected from:

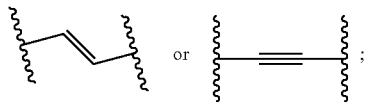

$T_1$ is linear $C_1$-$C_6$ alkyl, or linear $C_1$-$C_6$ alkyl independently substituted by $R^9$ and $R^{10}$, respectively;

$R^9$ and $R^{10}$ are each independently —H or methyl;

$R^8$ is —H, hydroxy, methyl, ethyl, propyl, isopropyl, cyclopropyl, cyclobutyl, cyclopentyl, cyclohexyl, methoxy, ethoxy, propoxy, isopropoxy, methylthio, ethylthio, propylthio, isopropylthio, 5- to 6-membered heterocyclyl or —$NR^{11}R^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, cyclohexyl, hydroxyethyl, hydroxypropyl, hydroxybutyl, hydroxypentyl, hydroxyhexyl, methoxyethyl, methoxypropyl, methoxybutyl, methoxypentyl, methoxyhexyl, ethoxyethyl, ethoxypropyl, ethoxybutyl, ethoxypentyl, ethoxyhexyl, propoxyethyl, propoxypropyl, propoxybutyl, propoxypentyl, propoxyhexyl, isopropoxyethyl, isopropoxypropyl, isopropoxybutyl, isopropoxypentyl or isopropoxyhexyl;

the 5- to 6-membered heterocyclyl is a heterocyclyl containing 1-2 heteroatoms selected from N, O or S, the 5- to 6-membered heterocyclyl is unsubstituted or substituted by any one or two of the group consisting of: methyl, ethyl, propyl, isopropyl, hydroxy, fluorine, chlorine, hydroxymethyl, hydroxyethyl, hydroxypropyl, or trifluoromethyl;

the 5- to 6-membered heterocycle is selected from:

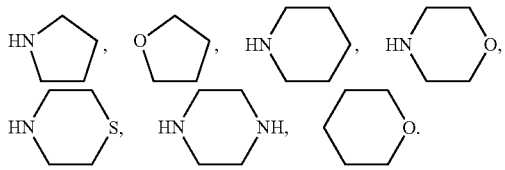

Alternatively,
R² is

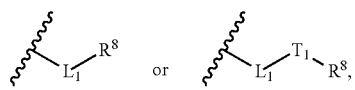

L₁ is selected from:

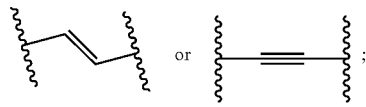

T₁ is linear C₁-C₆ alkyl, or linear C₁-C₆ alkyl independently substituted by R⁹ and R¹⁰, respectively;

R⁹ and R¹⁰ are each independently —H or methyl;

R⁸ is —H, hydroxy, methyl, ethyl, propyl, isopropyl, methoxy, ethoxy, propoxy, isopropoxy, methylthio, ethylthio, propylthio, isopropylthio, cyclopropyl, cyclobutyl, cyclopentyl, cyclohexyl, 5- to 6-membered heterocyclyl or —NR¹¹R¹², R¹¹ and R¹² are each independently is —H, methyl, ethyl, propyl, butyl, pentyl, hexyl, isopropyl, sec-butyl, 1-ethylpropyl, cyclopropyl, cyclobutyl, cyclopentyl, hydroxyethyl, hydroxypropyl, hydroxybutyl, hydroxypentyl, methoxyethyl, methoxypropyl, methoxybutyl, methoxypentyl, ethoxyethyl, ethoxypropyl, ethoxybutyl, ethoxypentyl, propoxyethyl, propoxypropyl, propoxybutyl, propoxypentyl, isopropoxyethyl, isopropoxypropyl, isopropoxybutyl or isopropoxypentyl;

the 5- to 6-membered heterocyclyl is a heterocyclyl containing 1-2 heteroatoms selected from N, O or S, the 5- to 6-membered heterocyclyl is unsubstituted or substituted by one or two of the group consisting of: methyl, ethyl, propyl, isopropyl, hydroxy, fluorine, chlorine, hydroxymethyl, hydroxyethyl, and trifluoromethyl;

the 5- to 6-membered heterocyclyl is selected from:

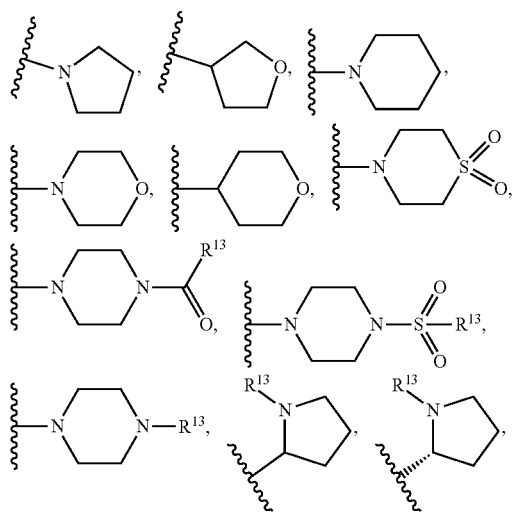

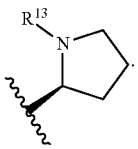

R¹³ is —H, amino, methylamino, dimethylamino, methyl, ethyl, propyl, or isopropyl.

The present disclosure also relates to a method for treating diseases or disorders mediated by kinases such as EGFR, HER2, HER3 and HER4, which includes administering a therapeutically effective amount of compounds of formula (I) or salts thereof to a patient in need (human or other mammals, especially human), and the diseases or disorders mediated by EGFR, HER2, HER3 and HER4 kinase include those mentioned above.

The present disclosure provides a method for preparing the above compound or a pharmaceutically acceptable salt, isomer, hydrate, solvate, or prodrug thereof, which comprises the following steps:

the compound of formula (I) is prepared by the reaction of R²C(O)Cl with the compound of formula (VIII), or by the chlorination reaction of R²COOH followed by the reaction with the compound of formula (VIII);

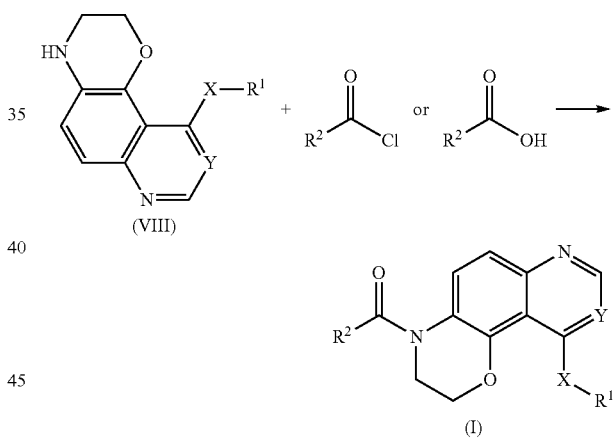

or, when R² is

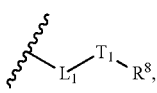

wherein L₁ is

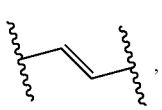

and R⁸ is —NR¹¹R¹², the compound of formula (I) is prepared by the reaction of compound of formula (VIII) with

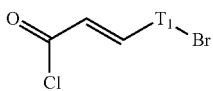

followed by the reaction with HNR[11]R[12],

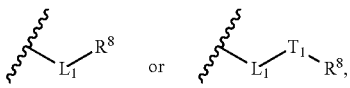

or, when R[2] is

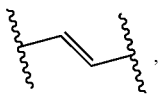 [SMILES: */C=C/*]

wherein L₁ is

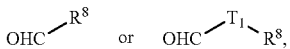

the compound of formula (I) is prepared by the reaction of compound of formula (IX) with

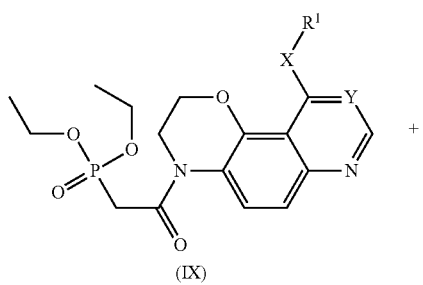

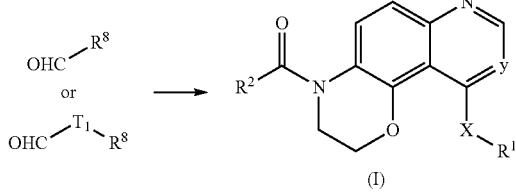

R[1], R[2], R[8], R[9], R[10], R[11], R[12], X, Y, L₁ and T₁ are as defined above.

The present disclosure also provides a compound represented by formula (VIII), wherein R and Y are as defined above,

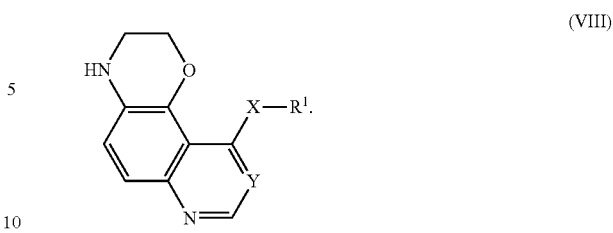

The present disclosure also provides a method for preparing the compound represented by formula (VIII), R[1] is as defined above, and Y is N. The preparation method includes the following steps:

Method A:

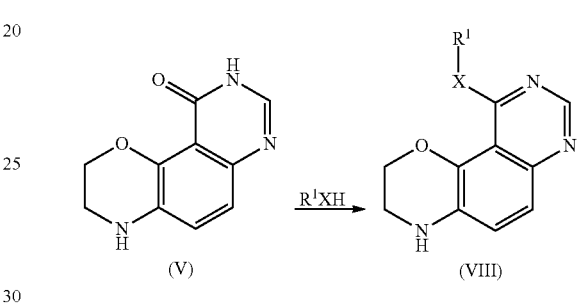

Compound of formula (VIII) is prepared by fully contacting 2,3,4,9-tetrahydro-10H-[1,4]oxazino[2,3-f]quinazolin-10-one as represented by formula (V) with R[1]XH, followed by Castros reagent;

or method B:

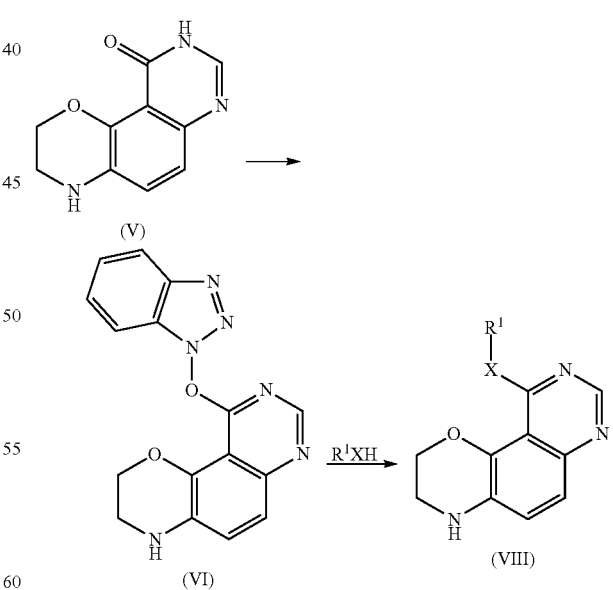

2,3,4,9-tetrahydro-10H-[1,4]oxazino[2,3-f]quinazolin-10-one as represented by formula (V) is fully contacted with Castros reagent to afford the compound of formula (VI), and compound (VI) is further reacted with R[1]XH to afford the compound represented by formula (VIII);

or method C:

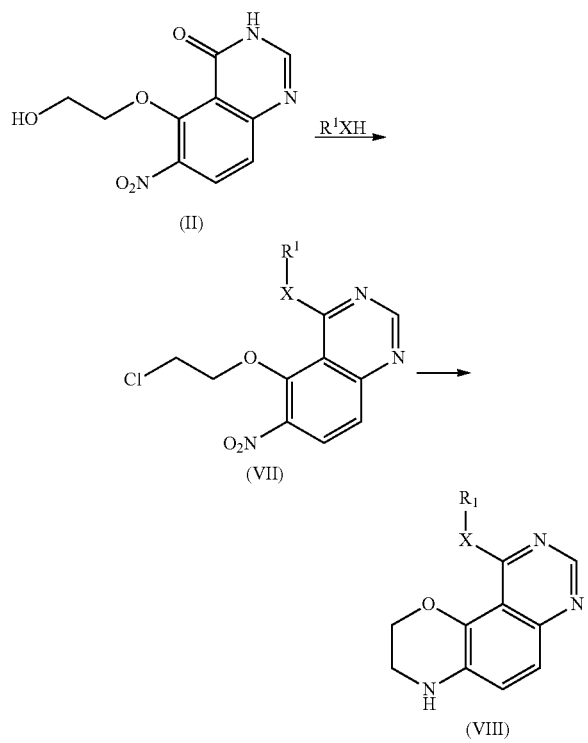

The compound represented by the formula (II) is reacted with a chlorinating reagent and then reacted with R$^1$XH to afford the compound represented by the formula (VII), and the compound represented by the formula (VII) is further subjected to a reduction and cyclization reaction to afford the compound represented by the formula (VIII).

DETAILED DESCRIPTION

The term "substituted" as used herein, includes multiple substituents (e.g., phenyl, aryl, heteroalkyl, heteroaryl), preferably 1 to 5 substituents, more preferably 1 to 3 substituents, most preferably 1 or 2 substituents, independently selected from the list of substituents.

Unless otherwise specified, alkyl includes saturated linear and branched hydrocarbon group, $C_1$-$C_8$ represents the number of carbon atoms of an alkyl is 1-8. Similarly, for example, $C_1$-$C_3$ represents the number of carbon atoms of an alkyl is 1-3, e.g., $C_1$-$C_6$ alkyl includes methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl, and 2-methylpentyl. Alkoxyl is an ether consisting of a linear or branched alkyl as previously described. Similarly, alkenyl and alkynyl groups include linear or branched alkenyl or alkynyl groups.

Cycloalkyl refers to a cyclic group formed by carbon atoms. For example, $C_3$-$C_7$ represents a cycloalkyl group having 3 to 7 carbon atoms, including cyclopropyl, cyclobutyl, cyclopentyl, cyclohexyl, and cycloheptyl. Similarly, cyclic alkenyl group is also included herein.

The term "aryl" as used herein, unless otherwise specified, refers to an unsubstituted or substituted aromatic group, such as phenyl, naphthyl, anthracenyl. The term "arylacyl" refers to —C(O)-aryl.

"Oxidized by one or two oxygen atoms" refers to a sulfur atom oxidized by one oxygen atom to form a double bond between the sulfur and oxygen, or oxidized by two oxygen atoms to form double bonds between the sulfur and two oxygen atoms.

The term "heterocyclyl" as used herein, unless otherwise specified, represents an unsubstituted or substituted stable 3 to 8 membered monocyclic saturated ring system consisting of carbon atoms and 1 to 3 heteroatoms selected from N, O, and S, wherein the N, S heteroatoms can be optionally oxidized, and the N heteroatoms can also be optionally quaternized. The heterocycle can be attached through any heteroatom or carbon atom to form a stable structure. Examples of such heterocyclyl rings include, but are not limited to, azetidinyl, pyrrolidinyl, tetrahydrofuranyl, tetrahydrothiazolyl, tetrahydropyranyl, morpholinyl, thiomorpholinyl, piperidinyl, piperazinyl, oxopiperazinyl, oxopiperidinyl, dioxolanyl, dioxanyl, tetrahydroimidazolyl, tetrahydrooxazolyl, thiomorpholine oxide, thiomorpholine dioxide and oxadiazolyl.

The term "heteroaryl" as used herein, unless otherwise specified, represents an unsubstituted or substituted stable 5 or 6 membered monocyclic aromatic ring system, and may also represent unsubstituted or substituted 9 or 10-membered benzo-fused heteroaromatic ring system or a bicyclic heteroaromatic ring system consisting of carbon atoms and one to three heteroatoms selected from N, O, S, wherein the N, S heteroatoms may optionally be oxidized, and N heteroatoms may optionally be quaternized. Heteroaryl can be attached at any heteroatom or carbon atom to form a stable structure. Heteroaryl includes but is not limited to thienyl, furyl, imidazolyl, pyrrolyl, thiazolyl, oxazolyl, isoxazolyl, pyranyl, pyridinyl, piperazinyl, pyrimidinyl, pyrazinyl, pyridazinyl, pyrazolyl, thiadiazolyl, triazolyl, indolyl, azaindolyl, indazolyl, azaindazolyl, benzimidazolyl, benzofuryl, benzothienyl, benzoisoxazolyl, benzoxazolyl, benzopyrazolyl, benzothiazolyl, benzothiadiazolyl, benzotriazolyl, adeninyl, quinolinyl, or isoquinolinyl.

The term "carbonyl" refers to a C(O) group.

Whenever the terms "alkyl" or "aryl" or either of their prefix roots appear in the name of a substituent (eg, aralkyl, dialkylamino), it shall be interpreted to contain those limitations given for the above "alkyl" and "aryl". Designated numbers of carbon atoms (e.g., $C_1$-$C_6$) shall independently represent the number of carbon atoms in an alkyl moiety or an alkyl moiety in a larger substituent (wherein the alkyl group is the prefix root).

The present disclosure also provides methods for preparing the corresponding compounds, wherein the compounds disclosed herein can be prepared using a variety of synthetic methods, including the methods described below. The compounds of the present disclosure, or pharmaceutically acceptable salts, isomers or hydrates thereof could be synthesized using the following methods and the known synthetic methods in the art of organic synthesis, or by variations of those methods as understood by those skilled in the art. The preferred methods include, but are not limited to, the methods described below.

The synthetic route of the compound of formula (I) is illustrated by the formula (I) wherein Y is N. The present disclosure are mainly illustrated by the following three preparation schemes:

Preparation route I of the compound represented by formula (I): wherein, $R^1$, $R^2$, $R^8$, $R^9$, $R^{10}$, $R^{11}$, $R^{12}$, X, $L_1$ and $T_1$ are as defined above.

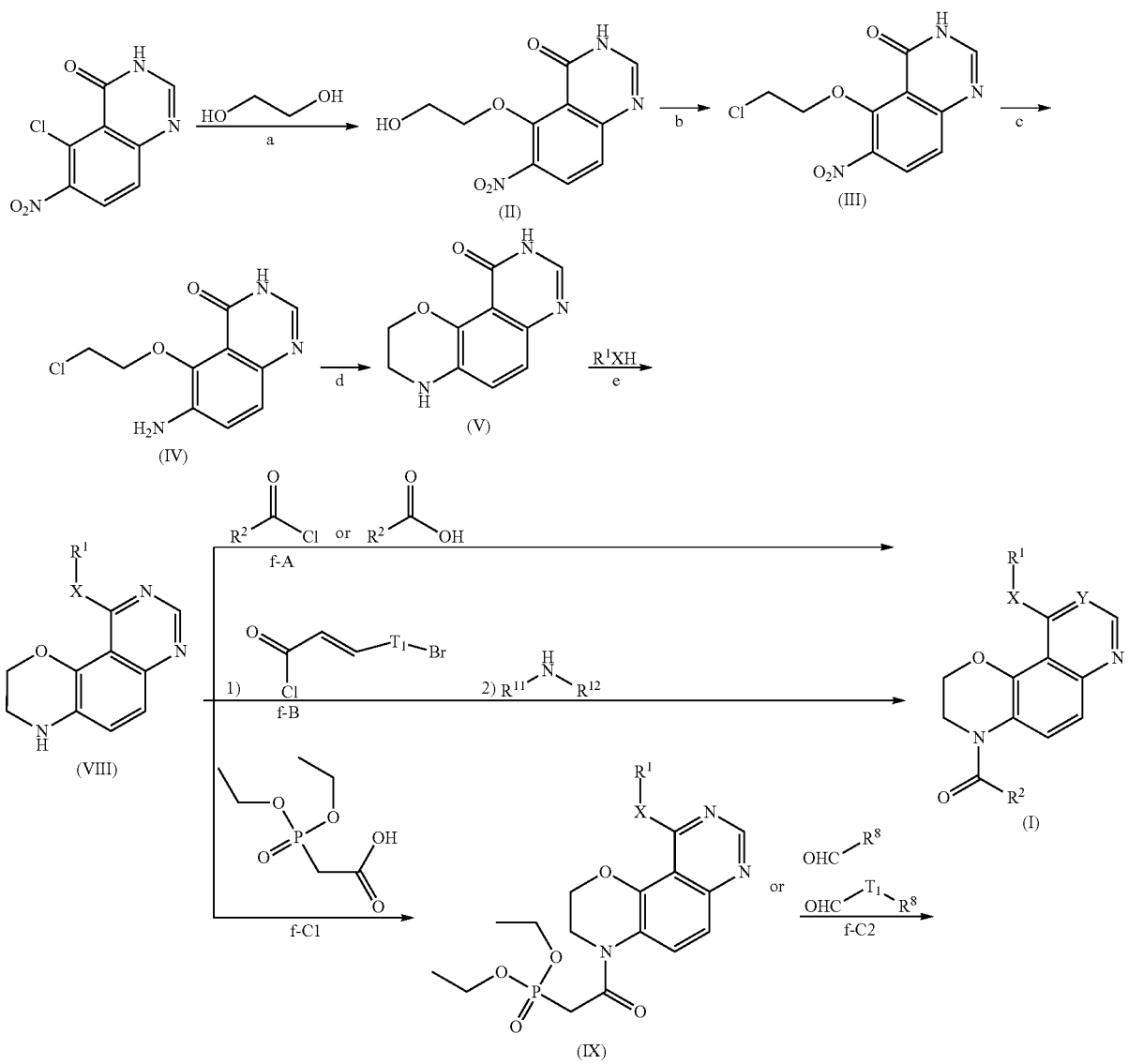

Reaction step a): 5-chloro-6-nitroquinazolin-4(3H)-one is fully contacted with ethylene glycol and sodium hydride to afford the compound represented by formula (II) of 5-(2-hydroxyethoxy)-6-nitroquinazolin-4(3H)-one.

Reaction step b): 5-(2-hydroxyethoxy)-6-nitroquinazolin-4(3H)-one represented by formula (II) is fully contacted with a chlorinating reagent, followed by adding water to afford 5-(2-chloroethoxy)-6-nitroquinazolin-4(3H)-one represented by formula (III). The chlorinating reagent includes, but is not limited to, any one or the combination of two or more of phosphorus oxychloride, sulfoxide chloride, phosphorus trichloride, phosphorus pentachloride and chlorine gas.

Reaction step c): 5-(2-chloroethoxy)-6-nitroquinazolin-4(3H)-one represented by formula (III) is subjected to a reduction reaction to afford 5-(2-chloroethoxy)-6-aminoquinazolin-4(3H)-one represented by formula (IV). The conditions of the reduction reaction include, but are not limited to, hydrogen and raney nickel, hydrogen and palladium on carbon, iron powder, zinc powder and stannous chloride.

Reaction step d): 5-(2-chloroethoxy)-6-aminoquinazolin-4(3H)-one represented by formula (IV) is dissolved in a solvent, and heated to afford 2,3,4,9-tetrahydro-10H-[1,4]oxazino[2,3-f]quinazolin-10-one represented by formula (V); the solvent is preferably selected from any one or the combination of two or more of the following: methanol, ethanol, isopropanol, tetrahydrofuran, N,N-dimethylformamide (DMF), N,N-dimethylacetamide (DMA), N-methylpyrrolidone (NMP), dioxane, and dichloroethane;

alternatively, the reaction can be carried out under base-catalyzed conditions, the base includes, but is not limited to, any one or the combination of two or more of the following: triethylamine, diisopropylethylamine, pyridine, 4-dimethylaminopyridine, 1,8-diazabicycloundec-7-ene, N-methylmorpholine, sodium carbonate, potassium carbonate and cesium carbonate.

Reaction step e): 2,3,4,9-tetrahydro-10H-[1,4]oxazino[2,3-f]quinazolin-10-one represented by formula (V) is fully contacted with $R^1XH$ and Castros reagent to afford an oxazino-quinazoline compound represented by formula (VII).

Alternatively, Castros reagent is selected from any one or the combination of two of the following: (benzotriazol-1- yloxy)tris(dimethylamino)phosphonium hexafluorphosphate (BOP) or (benzotriazol-1-yloxy)tripyrrolidinophosphonium hexafluorophosphate (PyBOP); the reaction can be carried out under base-catalyzed conditions, the base includes, but is not limited to, any one or the combination of two or more of the following: triethylamine, diisopropylethylamine, triethylenediamine (DABCO), 1,8-diazabicycloundec-7-ene (DBU), pyridine, N-methylmorpholine, 4-dimethylaminopyridine, sodium carbonate, potassium carbonate and cesium carbonate.

Reaction step f-A): the compound represented by formula (VIII) is condensed with $R^2C(O)Cl$, or the product of the reaction of $R^2COOH$ and a chlorinating reagent, to afford the compound represented by formula (I);

the chlorinating agent is preferably selected from any one or the combination of two or more of the following: phosphorus oxychloride, thionyl chloride, oxalyl chloride, phosphorus trichloride and phosphorus pentachloride;

alternatively, the reaction can be carried out under base-catalyzed conditions, the base includes, but is not limited to, any one or the combination of two or more of the following: triethylamine, diisopropylethylamine, pyridine, 4-dimethylaminopyridine, 1,8-diazabicycloundec-7-ene, N-methylmorpholine, sodium carbonate, potassium carbonate and cesium carbonate.

Reaction step f-B): or, when $R^2$ is

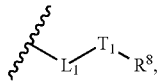

and $R^8$ is $HNR^{11}R^{12}$, and $L_1$ is

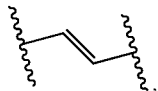

the compound represented by formula (VIII) is reacted with

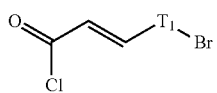

followed by adding amine having $R^{11}$ and $R^{12}$

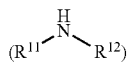

to afford the compound represented by formula (I); alternatively, the above reaction can be carried out in an organic solvent, the organic solvent includes, but is not limited to, any one or the combination of two or more of the following: tetrahydrofuran (THF), N,N-dimethylformamide (DMF), N,N-dimethylacetamide (DMA), N-methylpyrrolidone (NMP), dioxane, and dichloroethane;

Reaction step f-C): or, when $R^2$ is

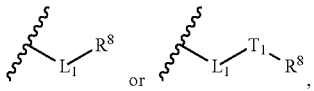

and $L_1$ is

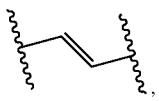

the compound of formula (IX) is obtained from the reaction of step f-C1 by the reaction of the compound of formula (VIII) and 2-(diethoxyphosphoryl)acetic acid under the action of a condensing agent, and the compound of formula (IX) is further reacted with

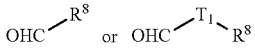

in the reaction step f-C2 to afford compound of formula (I).

Alternatively, the condensing agent includes, but is not limited to, any one or two or more of the following: carbodiimide type condensing agent, onium salt-based condensing agent, organophosphorus condensing agent and other types of condensing agent, alternatively, any one or the combination of two or more of the following: N,N'-carbonyldiimidazole (CDI), N,N'-dicyclohexylcarbodiimide (DCC), N,N'-diisopropylcarbodiimide (DIC), 1-hydroxybenzotriazole (HOBt), N,N-diisopropylethylamine (DIEA), 1-hydroxy-7-azabenzotriazole (HOAt), O-(benzotriazol-1-yl)-N,N,N',N'-tetramethyluronium tetrafluoroborate (TBTU), (benzotriazol-1-yloxy)tris(dimethylamino)phosphonium hexafluorophosphate (BOP), O-(benzotriazol-1-yl)-N,N,N',N'-tetramethyluronium hexafluorophosphate (HBTU), O-(6-chlorobenzotriazol-1-yl)-1,1,3,3-tetramethyluronium hexafluorophosphate (HCTU), O-(7-azabenzotriazol-1-yl)-N,N,N',N'-tetramethyluronium hexafluorophosphate (HATU), propylphosphonic anhydride (T3P), 1-(3-dimethylaminopropyl)-3-ethylcarbodiimide hydrochloride (EDCI), 1-ethyl-3-(3-dimethylaminopropyl)carbodiimide hydrochloride (EDC), (benzotriazol-1-yloxy)tripyrrolidinophosphonium hexafluorophosphate (PyBOP), and (3H-1,2,3-triazolo[4,5-b]pyridin-3-yloxy)tripyrrolidinophosphonium hexafluorophosphate (PyAOP);

alternatively, this step can be carried out in an organic base, the organic base includes, but is not limited to, any one or the combination of two or more of the following: triethylamine, diisopropylethylamine (DIEA), pyridine, 4-dimethylaminopyridine (DMAP), 2,6-dimethylpyridine (Lutidine), 1,8-diazabicycloundec-7-ene (DBU) or N-methylmorpholine.

Alternatively, step f-C2 can be carried out in an aprotic solvent under the action of an base. The aprotic solvent includes, but is not limited to, any one or the combination of two or more of the following: tetrahydrofuran (THF), N,N-dimethylformamide (DMF), N,N-dimethylacetamide (DMA), N-methylpyrrolidone (NMP), and dioxane; the base includes, but is not limited to, one of sodium hydride, and lithium bistrimethylsilylamide, or both.

The above steps f-A), f-B) and f-C) are parallel steps, that is, the compound represented by formula (I) can be prepared by the compound represented by formula (VIII) through one of steps f-A), f-B) and f-C), that is, the compound represented by formula (I) can be prepared by the compound represented by formula (VIII) through step f-A), or the compound represented by formula (I) can be prepared by the compound represented by formula (VIII) through step f-B), or the compound represented by formula (I) can be prepared by the compound represented by formula (VIII) through step f-C).

Preparation route II of the compound represented by formula (I), wherein, $R^1, R^2, R^8, R^9, R^{10}, R^{11}, R^{12}, X, L_1$ and $T_1$ are as defined above.

morpholine, 4-dimethylaminopyridine, sodium carbonate, potassium carbonate and cesium carbonate.

Reaction step b): 10-((1H-benzo[d][1,2,3]triazol-1-yl)oxy)-3,4-dihydro-2H-[1,4]oxazino[2,3-f]quinazoline represented by formula (VI) and $R^1XH$ are fully contacted in an organic solvent to afford the compound represented by formula (VIII);

alternatively, the organic solvent is selected from any one or the combination of two or more of the following: methanol, ethanol, isopropanol, tetrahydrofuran, N,N-dimethylformamide (DMF), N,N-dimethylacetamide (DMA), N-methylpyrrolidone (NMP), dioxane, and dichloroethane;

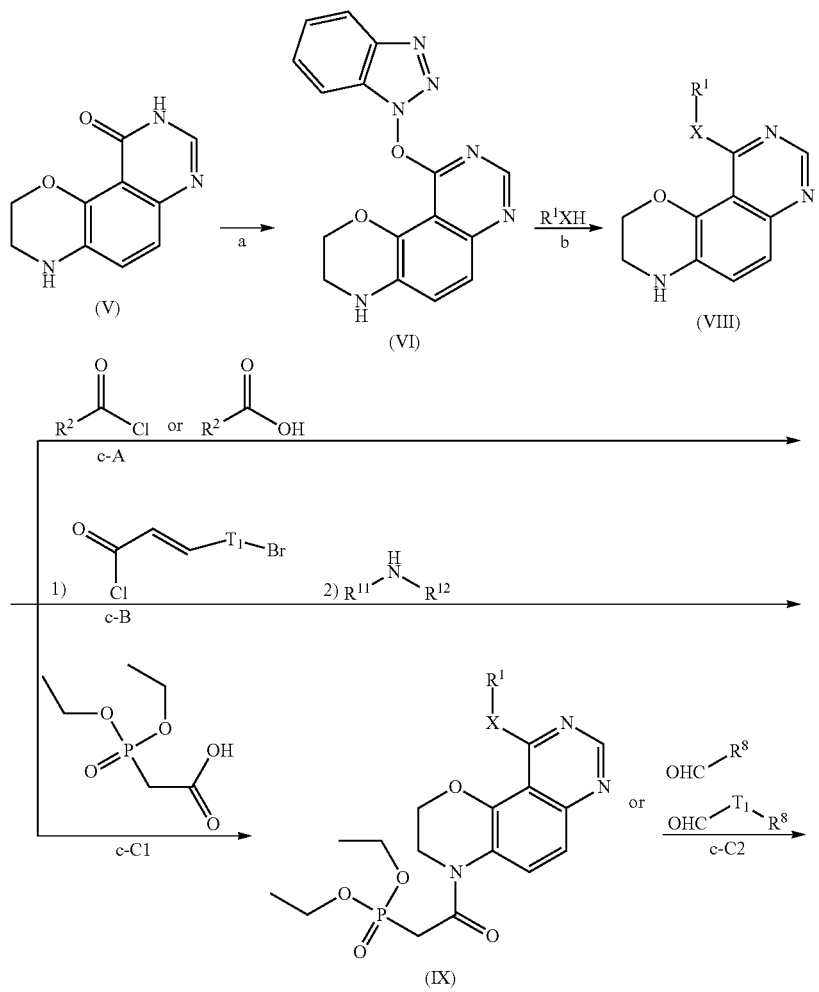

Reaction step a): 2,3,4,9-tetrahydro-10H-[1,4]oxazino[2,3-f]quinazolin-10-one represented by formula (V) is fully contacted with Castros reagent to afford the compound represented by formula (VI);

alternatively, Castros reagent is selected from any one of (benzotriazol-1-yloxy)tris(dimethylamino)phosphonium hexafluorophosphate (BOP) or (benzotriazol-1-yloxy)tripyrrolidinophosphonium hexafluorophosphate (PyBOP), or both;

alternatively, the above reaction can be carried out under basic conditions, the base includes, but is not limited to, any one or the combination of two or more of the following: triethylamine, diisopropylethylamine, triethylenediamine, 1,8-diazabicycloundec-7-ene (DBU), pyridine, N-methylalternatively, the reaction can be carried out under base-catalyzed conditions, the base includes, but is not limited to, any one or the combination of two or more of the following: triethylamine, diisopropylethylamine, pyridine, 4-dimethylaminopyridine, 1,8-diazabicycloundec-7-ene, N-methylmorpholine, sodium carbonate, potassium carbonate, cesium carbonate, and sodium hydride;

alternatively, the reaction can be carried out under acid-catalyzed conditions, the acid includes, but is not limited to, any one or the combination of two or more of the following: methanesulfonic acid, p-toluenesulfonic acid, benzenesulfonic acid, trifluoroacetic acid, and hydrochloric acid.

Reaction step c-A): the compound represented by formula (VIII) is subjected to a condensation reaction with $R^2C(O)Cl$ or the product of R²COOH and chlorinating agent to afford the compound represented by formula (I);

the chlorinating agent is selected from any one or the combination of two or more of phosphorus oxychloride, thionyl chloride, oxalyl chloride, phosphorus trichloride and phosphorus pentachloride;

alternatively, the above reaction can be carried out under basic conditions, and the base includes, but is not limited to, any one or the combination of two or more of the following: triethylamine, diisopropylethylamine, pyridine, 4-dimethylaminopyridine, 1,8-diazabicycloundec-7-ene, N-methylmorpholine, sodium carbonate, potassium carbonate, and cesium carbonate.

Reaction step c-B): or, when R² is

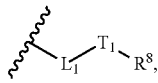

and R is HNR¹¹R¹², and L₁ is

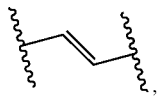

the compound represented by formula (VIII) is reacted with

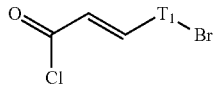

followed by adding amine having R¹¹ and R¹²

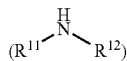

to afford the compound represented by formula (I).

Alternatively, the above reaction can be carried out in an organic solvent, which includes, but is not limited to, any one or the combination of two or more of the following: tetrahydrofuran (THF), N,N-dimethylformamide (DMF), N,N-dimethylacetamide (DMA), N-methylpyrrolidone (NMP), dioxane and dichloroethane;

Reaction step c-C): or, when R² is

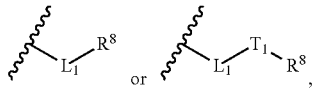

and L₁ is

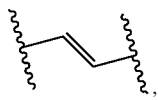

the compound of formula (IX) is prepared by the compound of formula (VIII) and 2-(diethoxyphosphoryl)acetic acid through the reaction in step c-C1 under the action of a condensing agent, the compound represented by formula (IX) is further reacted with

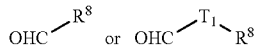

through the reaction in step c-C2 to afford the compound represented by formula (I).

Alternatively, the condensing agent includes, but is not limited to, any one or more of the following: carbodiimide type condensing agent, onium salt-based condensing agent, organophosphorus condensing agent and other types of condensing agent, alternatively, one or the combination of two or more of the following: N,N'-carbonyldiimidazole (CDI), N,N'-dicyclohexylcarbodiimide (DCC), N,N'-diisopropylcarbodiimide (DIC), 1-hydroxybenzotriazole (HOBt), N,N-diisopropylethylamine (DIEA), 1-hydroxy-7-azabenzotriazole (HOAt), O-(benzotriazol-1-yl)-N,N,N',N'-tetramethyluronium tetrafluoroborate (TBTU), (benzotriazol-1-yloxy)tris(dimethylamino)phosphonium hexafluorophosphate (BOP), O-(benzotriazol-1-yl)-N,N,N',N'-tetramethyluronium hexafluorophosphate (HBTU), O-(6-chlorobenzotriazol-1-yl)-1,1,3,3-tetramethyluronium hexafluorophosphate (HCTU), O-(7-azabenzotriazol-1-yl)-N,N,N',N'-tetramethyluronium hexafluorophosphate (HATU), propylphosphonic anhydride (T3P), 1-(3-dimethylaminopropyl)-3-ethylcarbodiimide hydrochloride (EDCI), 1-ethyl-3-(3-dimethylaminopropyl)carbodiimide hydrochloride (EDC), (benzotriazol-1-yloxy)tripyrrolidinophosphonium hexafluorophosphate (PyBOP), and (3H-1,2,3-triazolo[4,5-b]pyridin-3-yloxy)tripyrrolidinophosphonium hexafluorophosphate (PyAOP).

Alternatively, this step can be carried out in an organic base, the organic base includes, but is not limited to, any one or the combination of two or more of the following: triethylamine, diisopropylethylamine (DIEA), pyridine, 4-dimethylaminopyridine (DMAP), 2,6-dimethylpyridine (Lutidine), 1,8-diazabicycloundec-7-ene (DBU) and N-methylmorpholine.

Alternatively, step c-C2 can be carried out in an aprotic solvent under the action of a base. The aprotic solvent includes, but is not limited to, any one or the combination of two or more of the following: tetrahydrofuran (THF), N,N-dimethylformamide (DMF), N,N-dimethylacetamide (DMA), N-methylpyrrolidone (NMP), and dioxane; the alkali includes, but is not limited to, any one of sodium hydride, and lithium bistrimethylsilylamide, or both.

The above steps c-A), c-B) and c-C) are parallel steps, that is, the compound represented by formula (I) can be prepared by the compound represented by formula (VIII) through one of steps c-A), c-B) and c-C), that is, the compound represented by formula (I) can be prepared by the compound represented by formula (VIII) through step c-A), or the compound represented by formula (I) can be prepared by the compound represented by formula (VIII) through step c-B), or the compound represented by formula (I) can be prepared by the compound represented by formula (VIII) through step c-C).

Preparation route III of the compound represented by formula (I), wherein, R¹, R², R⁸, R⁹, R¹⁰, R¹¹, R¹², X, L₁ and T₁ are as defined above.

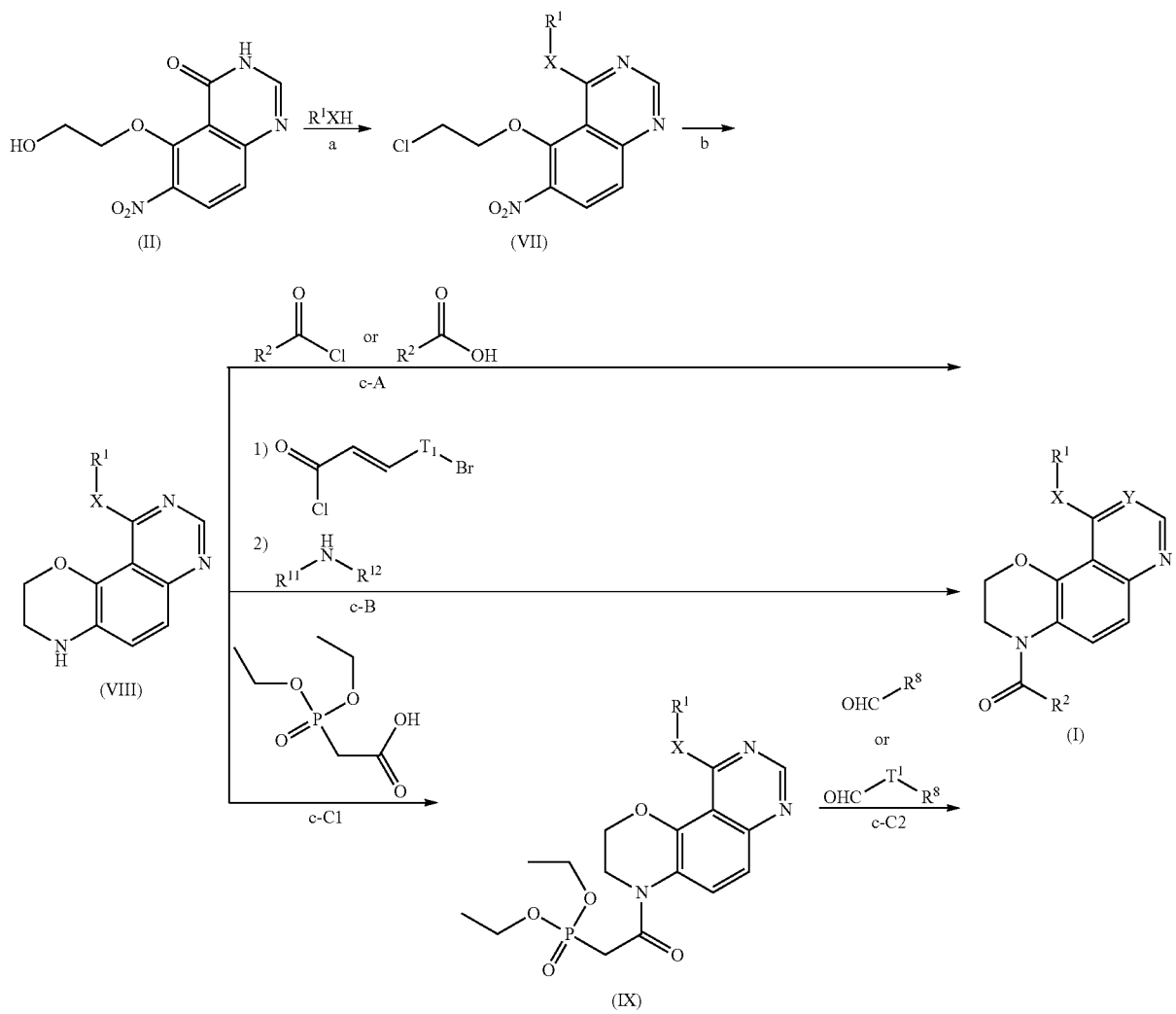

Reaction step a): the compound represented by formula (II), 5-(2-hydroxyethoxy)-6-nitroquinazolin-4(3H)-one, is reacted with a chlorinating reagent followed by contacting with $R^1XH$ to afford quinazoline compounds represented by formula (VII);

alternatively, the chlorinating reagent include, but are not limited to, any one or the combination of two or more of the following: phosphorus oxychloride, thionyl chloride, phosphorus trichloride, phosphorus pentachloride and chlorine gas;

Reaction step b): the quinazoline compounds represented by formula (VII) are subjected to reducing conditions to afford oxazino-quinazoline compounds represented by formula (VIII), the reduction conditions include, but are not limited to, hydrogen and raney nickel, hydrogen and palladium on carbon, iron powder, zinc powder, and stannous chloride.

Reaction step c-A): the compound represented by formula (VIII) is subjected to a condensation reaction with $R^2C(O)Cl$ or the product of $R^2COOH$ and a chlorinating reagent to obtain a compound represented by formula (I);

the chlorinating agent is selected from any one or a combination of two or more of the following: phosphorus oxychloride, thionyl chloride, oxalyl chloride, phosphorus trichloride, and phosphorus pentachloride; alternatively, the above reaction can be carried out under basic conditions, the base includes, but is not limited to, triethylamine, diisopropylethylamine, pyridine, 4-dimethylaminopyridine, 1,8-diazabicycloundec-7-ene, N-methylmorpholine, sodium carbonate, potassium carbonate and cesium carbonate Reaction step c-B): or, when $R^2$ is

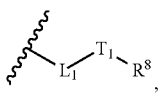, and $R^8$ is $HNR^{11}R^{12}$, and $L_1$ is

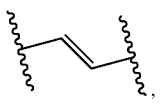, the compound represented by formula (VIII) is reacted with

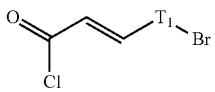

followed by adding amine having $R^{11}$ and $R^{12}$

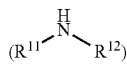

to afford the compound represented by formula (I).

Alternatively, the above reaction can be carried out in an organic solvent, the organic solvent includes, but is not limited to, any one or a combination of two or more of the following: tetrahydrofuran (THF), N,N-dimethylformamide (DMF), N,N-dimethylacetamide (DMA), N-methylpyrrolidone (NMP), dioxane, and dichloroethane;

Reaction step c-C): or, when $R^2$ is

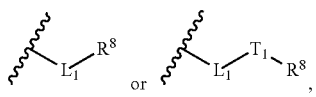

and $L_1$ is

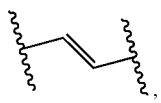

the compound of formula (IX) is prepared by the compound of formula (VIII) and 2-(diethoxyphosphoryl)acetic acid through the reaction in step c-C1 under the action of a condensing agent, the compound represented by formula (IX) is further reacted with

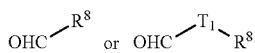

through reaction of step c-C2 to afford the compound represented by formula (I);

alternatively, the condensing agent includes, but is not limited to, any one or more of the following: carbodiimide type condensing agent, onium salt-based condensing agent, organophosphorus condensing agent and other types of condensing agent, alternatively, one or the combination of two or more of the following: N,N'-carbonyldiimidazole (CDI), N,N'-dicyclohexylcarbodiimide (DCC), N,N'-diisopropylcarbodiimide (DIC), 1-hydroxybenzotriazole (HOBt), N,N-diisopropylethylamine (DIEA), 1-hydroxy-7-azabenzotriazole (HOAt), O-(benzotriazol-1-yl)-N,N,N',N'-tetramethyluronium tetrafluoroborate (TBTU), (benzotriazol-1-yloxy)tris(dimethylamino)phosphonium hexafluorophosphate (BOP), O-(benzotriazol-1-yl)-N,N,N',N'-tetramethyluronium hexafluorophosphate (HBTU), O-(6-chlorobenzotriazol-1-yl)-1,1,3,3-tetramethyluronium hexafluorophosphate (HCTU), O-(7-azabenzotriazol-1-yl)-N,N,N',N'-tetramethyluronium hexafluorophosphate (HATU), propylphosphonic anhydride (T3P), 1-(3-dimethylaminopropyl)-3-ethylcarbodiimide hydrochloride (EDCI), 1-ethyl-3-(3-dimethylaminopropyl)carbodiimide hydrochloride (EDC), (benzotriazol-1-yloxy)tripyrrolidinophosphonium hexafluorophosphate (PyBOP), and (3H-1,2,3-triazolo[4,5-b]pyridin-3-yloxy)tripyrrolidinophosphonium hexafluorophosphate (PyAOP);

alternatively, this step can be carried out in an organic base, the organic base includes, but is not limited to, any one or the combination of two or more of the following: triethylamine, diisopropylethylamine (DIEA), pyridine, 4-dimethylaminopyridine (DMAP), 2,6-dimethylpyridine (Lutidine), 1,8-diazabicycloundec-7-ene (DBU) and N-methylmorpholine.

Alternatively, step c-C2 can be carried out in an aprotic solvent under the action of a base. The aprotic solvent includes, but is not limited to, any one or the combination of two or more of the following: tetrahydrofuran (THF), N,N-dimethylformamide (DMF), N,N-dimethylacetamide (DMA), N-methylpyrrolidone (NMP), and dioxane; the alkali includes, but is not limited to, any one of sodium hydride, and lithium bistrimethylsilylamide, or both.

The above steps c-A), c-B) and c-C) are parallel selection steps, that is, the compound represented by formula (I) can be prepared by the compound represented by formula (VIII) through one of steps c-A), c-B) and c-C), that is, the compound represented by formula (I) can be prepared by the compound represented by formula (VIII) through step c-A), or the compound represented by formula (I) can be prepared by the compound represented by formula (VIII) through step c-B), or the compound represented by formula (I) can be prepared by the compound represented by formula (VIII) through step c-C).

It is apparent that the compounds of Formula (I), the isomers, crystalline forms or prodrugs, and pharmaceutically acceptable salts thereof, may exist in both solvated and unsolvated forms. For example, the solvated form can be a hydrate form. The disclosure includes both solvated and unsolvated forms.

The compounds of the present disclosure may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound, separating the diastereomers and converting (e.g., hydrolyzing) the individual diastereomers to the corresponding pure enantiomers. All such isomers, including diastereomer mixtures and pure enantiomers are considered as part of the disclosure.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into a compound of Formula (I) of the present disclosure in vivo. Such transformation is affected by hydrolysis of the prodrug in the blood or enzymatic conversion to the parent compound in the blood or tissue.

Pharmaceutical compositions of this disclosure comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, anti-inflammatory agent, antifungal agent, antibiotic, or an anti-vascular hyper proliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid drench. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, including a method for administering to the subject a therapeutically effective amount of a composition containing the compound of the present disclosure.

The present disclosure also includes the use of the compounds of the present disclosure or pharmaceutically acceptable derivatives thereof in the manufacture of drugs for the treatment of cancer and autoimmune diseases associated with tyrosine kinases EGFR, HER2, HER3 and HER4, wherein the diseases include, but are not limited to, cancer (including non-solid tumors, solid tumors, primary or metastatic cancer, as indicated elsewhere herein and including one or more of other therapies to which the cancer is resistant or refractory), as well as other diseases (including, but not limited to, ocular fundus diseases, psoriasis, atheroma, pulmonary fibrosis, liver fibrosis, myelofibrosis, and the like). The cancer includes, but is not limited to any one of non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, and cholangiocarcinoma.

The present disclosure is better illustrated by referring to the examples provided below, wherein all temperatures are in degrees Celsius unless otherwise stated.

DETAILED EMBODIMENTS

Synthesis of the Compound Represented by Formula VIII (Intermediate of Compounds of the Present Disclosure)

Preparation of N-(4-phenoxyphenyl)-3,4-dihydro-2H-[1,4]oxazino[2,3-f]quinazolin-10-amine (Intermediate No. VIII-1)

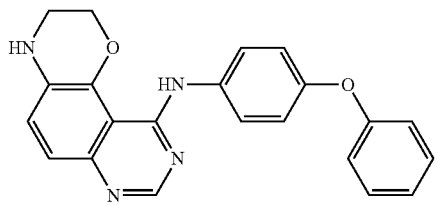 [SMILES: c1ccc(Oc2ccc(Nc3ncnc4ccc5c(c34)OCCN5)cc2)cc1]

Step 1) Preparation of 5-(2-hydroxyethoxy)-6-nitroquinazolin-4(3H)-one (II)

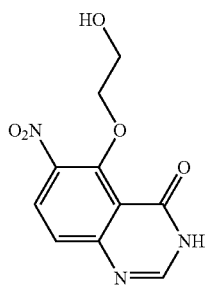 [SMILES: O=c1[nH]cnc2ccc([N+](=O)[O-])c(OCCO)c12]

Ethylene glycol (352.7 g, 5.7 mol) was dissolved in 1 L of DMF, cooled in an ice bath, to which sodium hydride was added (68.2 g, 2.8 mol), and stirred for 0.5 h. 5-chloro-6-nitroquinazolin-4(3H)-one (128 g, 0.57 mol) was added, and the reaction was slowly warmed to room temperature and stirred until the reaction was completed. Ethyl acetate was added until a large amount of solid was precipitated out, which was filtered with suction, and the resulting solid was slurried with water. The slurry was adjusted to weak acidic with hydrochloric acid and filtered with suction to afford 129.7 g of a white solid with a yield of 91%. $^1$H NMR (DMSO-$d_6$, 400 MHz) δ 12.55 (1H, s), 8.13-8.28 (2H, m), 7.52 (1H, d, J=8.9 Hz), 4.76 (1H, brs), 4.04-4.32 (2H, m), 3.60-3.84 (2H, m); MS: 252[M+H]+.

Step 2) Preparation of 5-(2-chloroethoxy)-6-nitro-N-(4-phenoxyphenyl)quinazolin-4-amine (VII-1)

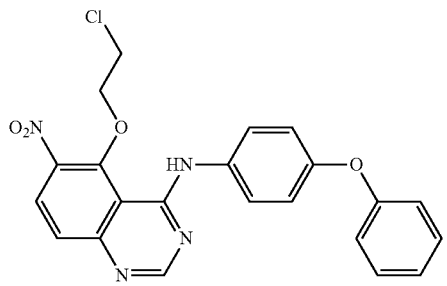 [SMILES: O=[N+]([O-])c1ccc2ncnc(Nc3ccc(Oc4ccccc4)cc3)c2c1OCCCl]

5-(2-hydroxyethoxy)-6-nitroquinazolin-4(3H)-one (3 g, 11.94 mmol) was added to a round-bottomed flask, to which thionyl chloride was added and stirred to dissolve it, catalytic amount of dimethylformamide was added dropwise, the reaction solution was heated to reflux until the raw materials were completely reacted, the reaction solution was evaporated to dryness under reduced pressure to afford a yellow solid, which was directly dissolved in dichloromethane, then 4-phenoxyaniline (2.2 g, 11.94 mmol) in ethanol was added and stirred until the reaction was completed. N-hexane was added and stirred until a large amount of solid was precipitated out, which was filtered with suction, washed with petroleum ether, and dried in air to afford 3.9 g of yellow solid with a yield of 88%. MS: 437[M+H]+.

Step 3) Preparation of N-(4-phenoxyphenyl)-3,4-dihydro-2H-[1,4]oxazino[2,3-f]quinazolin-10-amine (Intermediate No. VIII-1)

5-(2-chloroethoxy)-6-nitro-N-(4-phenoxyphenyl)quinazolin-4-amine (VII-1) (3.9 g, 8.7 mmol) was added to a round-bottomed flask, to which a mixed solvent of ethanol and water was added. Then iron powder (1.3 g, 22.7 mmol) and acetic acid (1.85 mL, 32.27 mmol) were added in sequence, and the reaction solution was heated and stirred until the reaction was completed. The solvent was distilled off, and extracted with ethyl acetate, concentrated, and subjected to column chromatography to afford 2.2 g of yellow solid with a yield of 65%. $^1$H NMR (300 MHz, DMSO-$d_6$) δ 9.92 (s, 1H), 8.47 (s, 1H), 7.79 (d, J=8.9 Hz, 2H), 7.44-7.37 (m, 3H), 7.35-7.28 (m, 1H), 7.16-7.13 (m, 1H), 7.09-7.06 (m, 2H), 7.04-7.00 (m, 2H), 6.82-6.74 (m, 1H), 4.71-4.66 (m, 2H), 4.13-4.08 (m, 2H); MS: 371[M+H]+.

Preparation of Intermediate N-(4-(3-methylphenoxy)phenyl)-3,4-dihydro-2H-[1,4]oxazino[2,3-f]quinazolin-10-amine (Intermediate No. VIII-2)

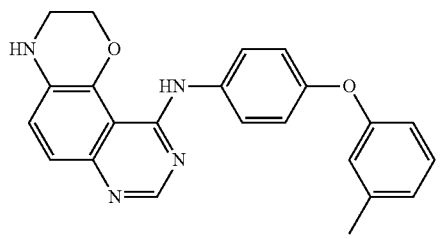 [SMILES: Cc1cccc(Oc2ccc(Nc3ncnc4ccc5c(c34)OCCN5)cc2)c1]

Step 1) is the same as the step 1) of the synthetic route of Intermediate No. VIII-1.

Step 2) Preparation of 5-(2-chloroethoxy)-6-nitroquinazolin-4(3H)-one (III)

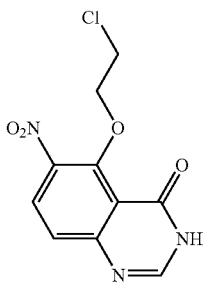 [SMILES: O=c1[nH]cnc2ccc([N+](=O)[O-])c(OCCCl)c12]

5-(2-hydroxyethoxy)-6-nitroquinazolin-4(3H)-one (129.7 g, 0.52 mol) was placed in a flask, to which 200 ml of phosphorus oxychloride was added and heated to reflux until the reaction was completed. Phosphorus oxychloride was evaporated off, and slurried with water until a large amount of solid was precipitated out, which was filtered with suction to afford 120.8 g of white solid with a yield of 87%. $^1$H NMR (400 MHz, DMSO-$d_6$) δ 12.55 (s, 1H), 8.24-8.21 (m, 2H), 7.56 (d, J=9.0 Hz, 1H), 4.41 (t, J=5.4 Hz, 2H), 3.96 (t, J=5.4 Hz, 2H); MS: 270[M+H]$^+$.

Step 3) Preparation of 5-(2-chloroethoxy)-6-amino-quinazolin-4(3H)-one (IV)

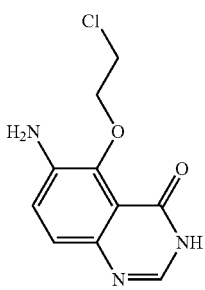

5-(2-chloroethoxy)-6-nitroquinazolin-4(3H)-one (120.8 g, 0.45 mol) was dissolved in a mixed solvent of methanol and tetrahydrofuran, to which 40 g raney nickel was added, and stirred at room temperature under hydrogen atmosphere until the reaction was completed. The reaction was filtered with suction, and concentrated to afford 107.4 g of a yellow solid with a yield of 100%. $^1$H NMR (400 MHz, DMSO-$d_6$) 11.76 (s, 1H), 7.74 (s, 1H), 7.24 (d, J=2.2 Hz, 2H), 5.32 (s, 2H), 4.15 (t, J=5.6 Hz, 2H), 3.97 (t, J=5.6 Hz, 2H); MS: 240[M+H]$^+$.

Step 4) Preparation of 2,3,4,9-tetrahydro-10H-[1,4]oxazino[2,3-f]quinazolin-10-one (V)

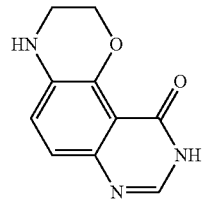

5-(2-chloroethoxy)-6-aminoquinazolin-4(3H)-one (107.4 g, 0.45 mol) was dissolved in 1 L of DMF, to which triethylamine (94 mL, 0.68 mol) was added, heated until the reaction was completed, and then DMF was distilled off. Dichloromethane was added and stirred until a large amount of solid was precipitated out, which was filtered with suction to afford 80 g of a white solid with a yield of 88%. $^1$H NMR (DMSO-d6, 300 MHz) δ 11.66 (1H, s), 7.67 (1H, s), 6.96-7.03 (2H, m), 6.11 (1H, s), 4.13-4.21 (2H, m), 3.25-3.33 (2H, m); MS: 204[M+H]$^+$.

Step 5) Preparation of N-(4-(3-methylphenoxy)phenyl)-3,4-dihydro-2H-[1,4]oxazino[2,3-f]quinazolin-10-amine (Intermediate No. VIII-2)

2,3,4,9-tetrahydro-10H-[1,4]oxazino[2,3-f]quinazolin-10-one (0.5 g, 2.46 mmol), 4-(m-tolyloxy)aniline (979 mg, 4.92 mmol), (benzotriazol-1-oxy)tris(dimethylamino)phosphonium hexafluorphosphate (BOP)(1.4 g, 3.20 mmol) were placed in a round-bottomed flask, to which 5 ml of acetonitrile was added, and 1,8-diazabicycloundec-7-ene (DBU) (0.56 g, 3.69 mmol) was added after stirring well, and then was stirred under room temperature until the reaction was completed. The solvent was distilled off, and the resulting mixture was purified using silica gel column chromatography to afford 710 mg of brown solid with a yield of 75%. MS: 385[M+H]$^+$.

Preparation of Intermediate N-(3-trifluoromethyl-4-(3-fluorobenzyloxy)phenyl)-3,4-dihydro-2H-[1,4]oxazino[2,3-f]quinazolin-10-amine (Intermediate No. VIII-3)

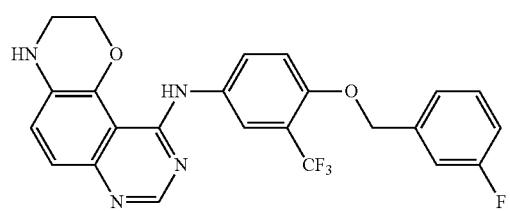 [SMILES: Fc1cccc(COc2ccc(Nc3ncnc4ccc5c(c34)OCCN5)cc2C(F)(F)F)c1]

Step 1) to Step 4) are the same as Step 1) to Step 4) in the preparation method of Intermediate No. VIII-2.

Step 5) Preparation of 10-((1H-benzo[d][1,2,3]triazol-1-yl)oxy)-3,4-dihydro-2H-[1,4]oxazino[2,3-f]quinazoline (VI)

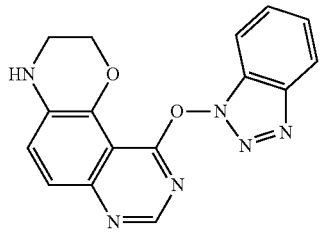 [SMILES: c1ccc2c(c1)nnn2Oc1ncnc2ccc3c(c12)OCCN3]

2,3,4,9-tetrahydro-10H-[1,4]oxazino[2,3-f]quinazolin-10-one (20.3 g, 100 mmol) and (benzotriazol-1-yloxy)tris(dimethylamino)phosphonium hexafluorphosphate (BOP) (44.2 g, 100 mmol) were placed in a round-bottomed flask, to which acetonitrile was added and stirred well, and 1,8-diazabicycloundec-7-ene (DBU)(15.2 g, 100 mmol) was then added, and stirred at room temperature until the reaction was completed. Water was added and stirred until a large amount of solid was precipitated out, which was filtered with suction to afford 28 g of yellow solid with a yield of 87%. $^1$H NMR (400 MHz, DMSO-$d_6$) δ 8.26 (s, 1H), 8.19 (d, J=8.4 Hz, 1H), 7.78 (d, J=8.3 Hz, 1H), 7.69-7.58 (m, 1H), 7.58-7.47 (m, 3H), 6.70 (s, 1H), 4.41 (t, J=4.2 Hz, 2H), 3.58-3.47 (m, 2H); MS: 321[M+H]$^+$.

Step 6) Preparation of N-(3-trifluoromethyl-4-(3-fluorobenzyloxy)phenyl)-3,4-dihydro-2H-[1,4]oxazino[2,3-f]quinazolin-10-amine (Intermediate No. VIII-3)

10-((1H-benzo[d][1,2,3]triazol-1-yl)oxy)-3,4-dihydro-2H-[1,4]oxazino[2,3-f]quinazoline (320 mg, 1 mmol) and 4-((3-fluorobenzyl)oxy)-3-(trifluoromethyl)aniline (285 mg, 1 mmol), p-toluenesulfonic acid monohydrate (17 mg, 0.1 mmol) were dissolved in isopropanol, and stirred at room temperature until the reaction was completed. Water was added and stirred, and filtered with suction to afford 424 mg of yellow solid product with a yield of 90%. MS: 471[M+H]$^+$.

Preparation of Intermediate No. VIII-4 to Intermediate No. VIII-63

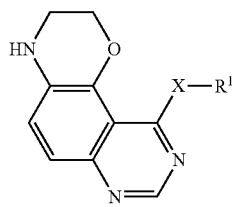

X = NH/O

Step 1) to Step 4) are the same as Step 1) to Step 4) in the synthetic method of Intermediate No. VIII-2.

Step 5): See Step 5) in the synthetic route of Intermediate No. VIII-2, wherein the same operation was used, and the method was carried out using 2,3,4,9-tetrahydro-1H-[1,4]oxazino[2,3-f]quinazolin-10-one (V) as the starting material, and replacing 4-m-tolyloxyaniline with an equal molar equivalent of R$^1$XH in the table below. Specific compounds are as follows:

| Intermediate No. | R$^1$X | Compound name | LCMS m/z = (M + H)$^+$ |
|---|---|---|---|
| VIII-4 | | N-(3-chloro-4-(3-fluorobenzyloxy)phenyl)-3,4-dihydro-2H-[1,4]oxazino[2,3-f]quinazolin-10-amine | 437 |
| VIII-5 | | N-(3-chloro-4-(pyridin-2-ylmethoxy)phenyl)-3,4-dihydro-2H-[1,4]oxazino[2,3-f]quinazolin-10-amine | 420 |

-continued

| Intermediate No. | R¹X | Compound name | LCMS m/z = (M + H)⁺ |
|---|---|---|---|
| VIII-6 | 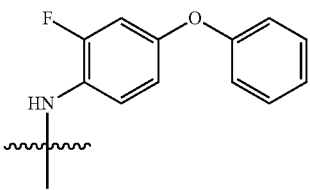 [SMILES: *Nc1ccc(Oc2ccccc2)cc1F] | N-(2-fluoro-4-phenoxyphenyl)-3,4-dihydro-2H-[1,4]oxazino[2,3-f]quinazolin-10-amine | 389 |
| VIII-7 | 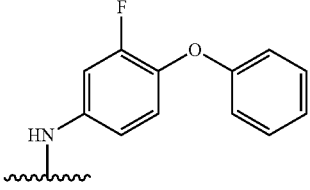 [SMILES: *Nc1ccc(Oc2ccccc2)c(F)c1] | N-(3-fluoro-4-phenoxyphenyl)-3,4-dihydro-2H-[1,4]oxazino[2,3-f]quinazolin-10-amine | 389 |
| VIII-8 | 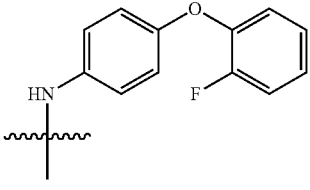 [SMILES: *Nc1ccc(Oc2ccccc2F)cc1] | N-(4-(2-fluorophenoxy)phenyl)-3,4-dihydro-2H-[1,4]oxazino[2,3-f]quinazolin-10-amine | 389 |
| VIII-9 | 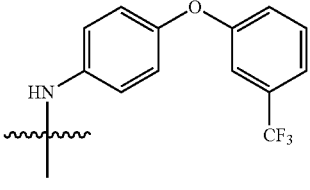 | N-(4-(3-trifluoromethylphenoxy)phenyl)-3,4-dihydro-2H-[1,4]oxazino[2,3-f]quinazolin-10-amine | 439 |
| VIII-10 | 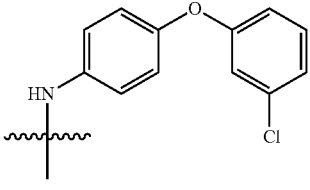 [SMILES: *Nc1ccc(Oc2cccc(Cl)c2)cc1] | N-(4-(3-chlorophenoxy)phenyl)-3,4-dihydro-2H-[1,4]oxazino[2,3-f]quinazolin-10-amine | 405 |
| VIII-11 | 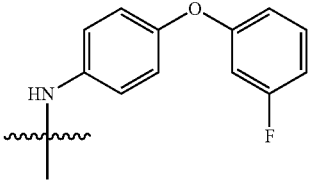 [SMILES: *Nc1ccc(Oc2cccc(F)c2)cc1] | N-(4-(3-fluorophenoxy)phenyl)-3,4-dihydro-2H-[1,4]oxazino[2,3-f]quinazolin-10-amine | 389 |
| VIII-12 | 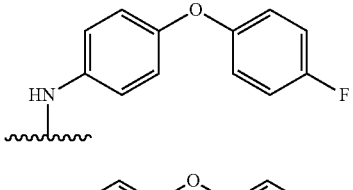 | N-(4-(4-fluorophenoxy)phenyl)-3,4-dihydro-2H-[1,4]oxazino[2,3-f]quinazolin-10-amine | 389 |
| VIII-13 | 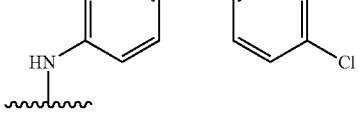 | N-(4-(4-chlorophenoxy)phenyl)-3,4-dihydro-2H-[1,4]oxazino[2,3-f]quinazolin-10-amine | 405 |

-continued

| Intermediate No. | R¹X | Compound name | LCMS m/z = (M + H)⁺ |
|---|---|---|---|
| VIII-14 | 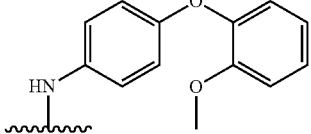 | N-(4-(2-methoxyphenoxy)phenyl)-3,4-dihydro-2H-[1,4]oxazino[2,3-f]quinazolin-10-amine | 401 |
| VIII-15 | 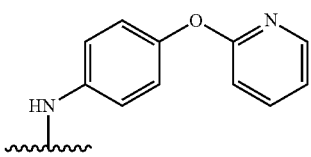 [SMILES: *Nc1ccc(Oc2ccccn2)cc1] | N-(4-(2-pyridyloxy)phenyl)-3,4-dihydro-2H-[1,4]oxazino[2,3-f]quinazolin-10-amine | 372 |
| VIII-16 | 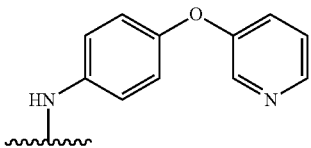 [SMILES: *Nc1ccc(Oc2cccnc2)cc1] | N-(4-(3-pyridyloxy)phenyl)-3,4-dihydro-2H-[1,4]oxazino[2,3-f]quinazolin-10-amine | 372 |
| VIII-17 | 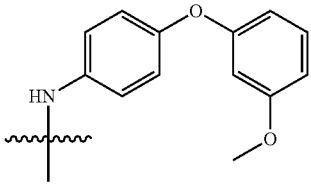 [SMILES: *Nc1ccc(Oc2cccc(OC)c2)cc1] | N-(4-(3-methoxyphenoxy)phenyl)-3,4-dihydro-2H-[1,4]oxazino[2,3-f]quinazolin-10-amine | 401 |
| VIII-18 | 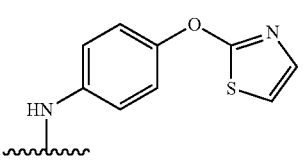 [SMILES: *Nc1ccc(Oc2nccs2)cc1] | N-(4-(thiazol-2-yloxy)phenyl)-3,4-dihydro-2H-[1,4]oxazino[2,3-f]quinazolin-10-amine | 378 |
| VIII-19 | 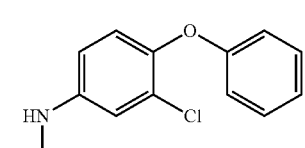 | N-(3-chloro-4-phenoxyphenyl)-3,4-dihydro-2H-[1,4]oxazino[2,3-f]quinazolin-10-amine | 405 |
| VIII-20 | 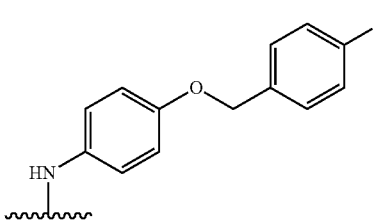 | N-(4-(4-fluorobenzyloxy)phenyl)-3,4-dihydro-2H-[1,4]oxazino[2,3-f]quinazolin-10-amine | 403 |
| VIII-21 | 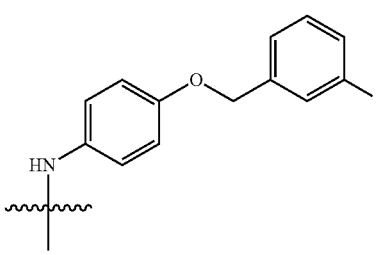 | N-(4-(3-fluorobenzyloxy)phenyl)-3,4-dihydro-2H-[1,4]oxazino[2,3-f]quinazolin-10-amine | 403 |

-continued

| Intermediate No. | R¹X | Compound name | LCMS m/z = (M + H)⁺ |
|---|---|---|---|
| VIII-22 | | N-(4-(3-trifluoromethylbenzyloxy)phenyl)-3,4-dihydro-2H-[1,4]oxazino[2,3-f]quinazolin-10-amine | 453 |
| VIII-23 | | N-(4-(pyridin-2-ylmethoxy)phenyl)-3,4-dihydro-2H-[1,4]oxazino[2,3-f]quinazolin-10-amine | 386 |
| VIII-24 | | N-(4-(thiophen-2-ylmethoxy)phenyl)-3,4-dihydro-2H-[1,4]oxazino[2,3-f]quinazolin-10-amine | 391 |
| VIII-25 | | N-(4-(thiazol-2-ylmethoxy)phenyl)-3,4-dihydro-2H-[1,4]oxazino[2,3-f]quinazolin-10-amine | 392 |
| VIII-26 | | N-(4-(benzylthio)phenyl)-3,4-dihydro-2H-[1,4]oxazino[2,3-f]quinazolin-10-amine | 401 |
| VIII-27 | | N-(3-methoxy-4-(3-fluorobenzyloxy)phenyl)-3,4-dihydro-2H-[1,4]oxazino[2,3-f]quinazolin-10-amine | 433 |

-continued

| Intermediate No. | R¹X | Compound name | LCMS m/z = (M + H)⁺ |
|---|---|---|---|
| VIII-28 | (3-fluoro-4-(3-fluorobenzyloxy)phenyl-NH-) | N-(3-fluoro-4-(3-fluorobenzyloxy)phenyl)-3,4-dihydro-2H-[1,4]oxazino[2,3-f]quinazolin-10-amine | 421 |
| VIII-29 | (4-(4-fluorophenyl)thio)phenyl-NH-) | N-(4-(4-fluorophenyl)thio)phenyl)-3,4-dihydro-2H-[1,4]oxazino[2,3-f]quinazolin-10-amine | 405 |
| VIII-30 | (4-(2-fluoro-5-methylphenoxy)phenyl-NH-) | N-(4-(2-fluoro-5-methylphenoxy)phenyl)-3,4-dihydro-2H-[1,4]oxazino[2,3-f]quinazolin-10-amine | 403 |
| VIII-31 | (4-(2-fluoro-5-chlorophenoxy)phenyl-NH-) | N-(4-(2-fluoro-5-chlorophenoxy)phenyl)-3,4-dihydro-2H-[1,4]oxazino[2,3-f]quinazolin-10-amine | 423 |
| VIII-32 | (4-(2,5-difluorophenoxy)phenyl-NH-) | N-(4-(2,5-difluorophenoxy)phenyl)-3,4-dihydro-2H-[1,4]oxazino[2,3-f]quinazolin-10-amine | 407 |

-continued

| Intermediate No. | R¹X | Compound name | LCMS m/z = (M + H)⁺ |
|---|---|---|---|
| VIII-33 | (4-(1-(3-fluorophenyl)ethoxy)phenyl-HN- structure) | N-(4-(1-(3-fluorophenyl)ethoxy)phenyl)-3,4-dihydro-2H-[1,4]oxazino[2,3-f]quinazolin-10-amine | 417 |
| VIII-34 | (4-(1-(pyridin-2-yl)ethoxy)phenyl-HN- structure) | N-(4-(1-(pyridin-2-yl)-ethoxy)phenyl)-3,4-dihydro-2H-[1,4]oxazino[2,3-f]quinazolin-10-amine | 400 |
| VIII-35 | (4-(pyridin-3-ylmethoxy)phenyl-HN- structure) | N-(4-(pyridin-3-ylmethoxy)phenyl)-3,4-dihydro-2H-[1,4]oxazino[2,3-f]quinazolin-10-amine | 386 |
| VIII-36 | (4-(pyridin-4-ylmethoxy)phenyl-HN- structure) | N-(4-(pyridin-4-ylmethoxy)phenyl)-3,4-dihydro-2H-[1,4]oxazino[2,3-f]quinazolin-10-amine | 386 |

-continued

| Intermediate No. | R¹X | Compound name | LCMS m/z = (M + H)⁺ |
|---|---|---|---|
| VIII-37 | | N-(4-(2-(2-(dimethylamino)ethoxy)phenoxy)phenyl)-3,4-dihydro-2H-[1,4]oxazino[2,3-f]quinazolin-10-amine | 458 |
| VIII-38 | | N-(4-(2-(3-(dimethylamino)propoxy)phenoxy)phenyl)-3,4-dihydro-2H-[1,4]oxazino[2,3-f]quinazolin-10-amine | 472 |
| VIII-39 | | N-(4-(2-(2-methoxyethoxy)phenoxy)phenyl)-3,4-dihydro-2H-[1,4]oxazino[2,3-f]quinazolin-10-amine | 445 |
| VIII-40 | | N-(4-phenoxyphenyl)-3,4-dihydro-2H-[1,4]oxazino[2,3-f]quinazolin-10-amine | 371 |
| VIII-41 | | N-(4-(benzyloxy)phenyl)-3,4-dihydro-2H-[1,4]oxazino[2,3-f]quinazolin-10-amine | 385 |

-continued

| Intermediate No. | R¹X | Compound name | LCMS m/z = (M + H)⁺ |
|---|---|---|---|
| VIII-42 | (4-(2-fluorobenzyloxy)phenyl)-NH– | N-(4-(2-fluorobenzyloxy)phenyl)-3,4-dihydro-2H-[1,4]oxazino[2,3-f]quinazolin-10-amine | 403 |
| VIII-43 | (4-(2-chlorobenzyloxy)phenyl)-NH– | N-(4-(2-chlorobenzyloxy)phenyl)-3,4-dihydro-2H-[1,4]oxazino[2,3-f]quinazolin-10-amine | 419 |
| VIII-44 | (4-(2-methylbenzyloxy)phenyl)-NH– | N-(4-(2-methylbenzyloxy)phenyl)-3,4-dihydro-2H-[1,4]oxazino[2,3-f]quinazolin-10-amine | 399 |
| VIII-45 | (4-(2-methoxybenzyloxy)phenyl)-NH– | N-(4-(2-methoxybenzyloxy)phenyl)-3,4-dihydro-2H-[1,4]oxazino[2,3-f]quinazolin-10-amine | 415 |
| VIII-46 | (4-(3-chlorobenzyloxy)phenyl)-NH– | N-(4-(3-chlorobenzyloxy)phenyl)-3,4-dihydro-2H-[1,4]oxazino[2,3-f]quinazolin-10-amine | 419 |

-continued

| Intermediate No. | R¹X | Compound name | LCMS m/z = (M + H)⁺ |
|---|---|---|---|
| VIII-47 | 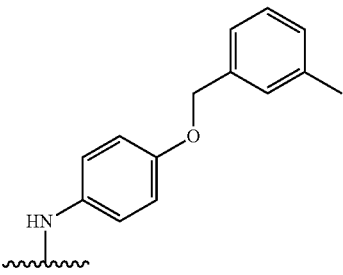 [SMILES: *Nc1ccc(OCc2cccc(C)c2)cc1] | N-(4-(3-methylbenzyloxy)phenyl)-3,4-dihydro-2H-[1,4]oxazino[2,3-f]quinazolin-10-amine | 399 |
| VIII-48 | 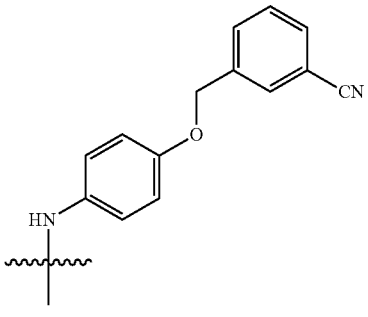 [SMILES: *Nc1ccc(OCc2cccc(C#N)c2)cc1] | N-(4-(3-cyanobenzyloxy)phenyl)-3,4-dihydro-2H-[1,4]oxazino[2,3-f]quinazolin-10-amine | 410 |
| VIII-49 | 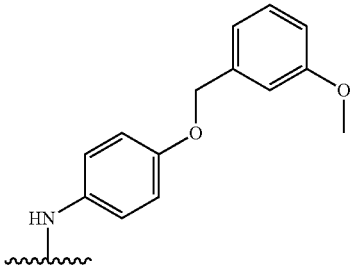 [SMILES: *Nc1ccc(OCc2cccc(OC)c2)cc1] | N-(4-(3-methoxybenzyloxy)phenyl)-3,4-dihydro-2H-[1,4]oxazino[2,3-f]quinazolin-10-amine | 415 |
| VIII-50 | 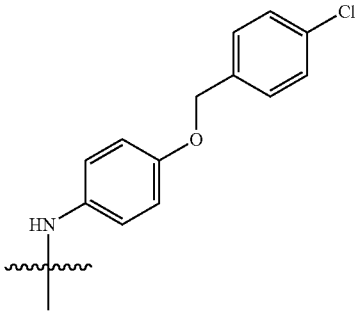 [SMILES: *Nc1ccc(OCc2ccc(Cl)cc2)cc1] | N-(4-(4-chlorobenzyloxy)phenyl)-3,4-dihydro-2H-[1,4]oxazino[2,3-f]quinazolin-10-amine | 419 |
| VIII-51 | 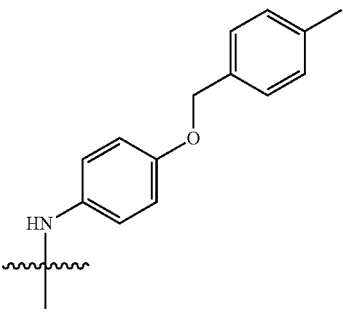 [SMILES: *Nc1ccc(OCc2ccc(C)cc2)cc1] | N-(4-(4-methylbenzyloxy)phenyl)-3,4-dihydro-2H-[1,4]oxazino[2,3-f]quinazolin-10-amine | 399 |

-continued

| Intermediate No. | R¹X | Compound name | LCMS m/z = (M + H)⁺ |
|---|---|---|---|
| VIII-52 | (2,5-difluorobenzyloxy-phenyl-HN- group) | N-(4-(2,5-difluorobenzyloxy)phenyl)-3,4-dihydro-2H-[1,4]oxazino[2,3-f]quinazolin-10-amine | 421 |
| VIII-53 | (2-chloro-5-fluorobenzyloxy-phenyl-HN- group) | N-(4-(2-chloro-5-fluorobenzyloxy)phenyl)-3,4-dihydro-2H-[1,4]oxazino[2,3-f]quinazolin-10-amine | 437 |
| VIII-54 | (3-chloro-4-(pyridin-2-ylmethoxy)phenoxy group) | 10-(3-chloro-4-(pyridin-2-ylmethoxy)phenoxy)-3,4-dihydro-2H-[1,4]oxazino[2,3-f]quinazoline | 421 |
| VIII-55 | (3-chloro-4-(3-fluorobenzyloxy)phenoxy group) | 10-(3-chloro-4-(3-fluorobenzyloxy)phenoxy)-3,4-dihydro-2H-[1,4]oxazino[2,3-f]quinazoline | 438 |
| VIII-56 | (4-phenoxyphenoxy group) | 10-(4-phenoxyphenoxy)-3,4-dihydro-2H-[1,4]oxazino[2,3-f]quinazoline | 372 |

-continued

| Intermediate No. | R¹X | Compound name | LCMS m/z = (M + H)⁺ |
|---|---|---|---|
| VIII-57 | 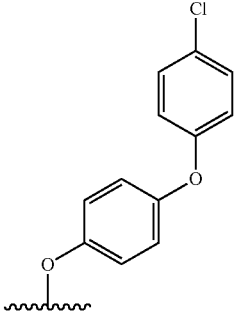 [SMILES: *Oc1ccc(Oc2ccc(Cl)cc2)cc1] | 10-(4-(4-chlorophenoxy)phenoxy)-3,4-dihydro-2H-[1,4]oxazino[2,3-f]quinazoline | 406 |
| VIII-58 | 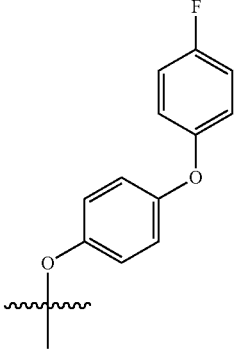 [SMILES: *Oc1ccc(Oc2ccc(F)cc2)cc1] | 10-(4-(4-fluorophenoxy)phenoxy)-3,4-dihydro-2H-[1,4]oxazino[2,3-f]quinazoline | 390 |
| VIII-59 | 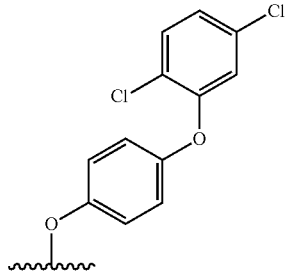 [SMILES: *Oc1ccc(Oc2cc(Cl)ccc2Cl)cc1] | 10-(4-(2,5-dichlorophenoxy)phenoxy)-3,4-dihydro-2H-[1,4]oxazino[2,3-f]quinazoline | 440 |
| VIII-60 | 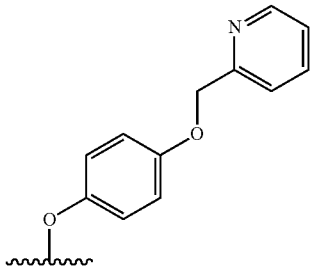 [SMILES: *Oc1ccc(OCc2ccccn2)cc1] | 10-(4-(pyridin-2-ylmethoxy)phenoxy)-3,4-dihydro-2H-[1,4]oxazino[2,3-f]quinazoline | 387 |
| VIII-61 | 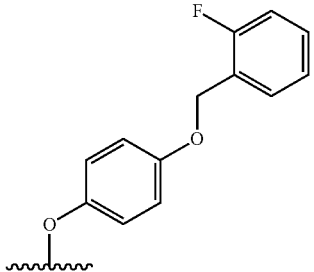 [SMILES: *Oc1ccc(OCc2ccccc2F)cc1] | 10-(4-(2-fluorobenzyloxy)phenoxy)-3,4-dihydro-2H-[1,4]oxazino[2,3-f]quinazoline | 404 |

-continued

| Intermediate No. | R¹X | Compound name | LCMS m/z = (M + H)⁺ |
|---|---|---|---|
| VIII-62 | 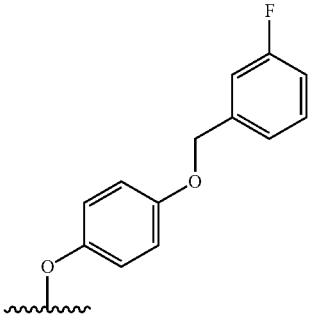 [SMILES: *Oc1ccc(OCc2cccc(F)c2)cc1] | 10-(4-(3-fluorobenzyloxy)phenoxy)-3,4-dihydro-2H-[1,4]oxazino[2,3-f]quinazoline | 404 |
| VIII-63 | 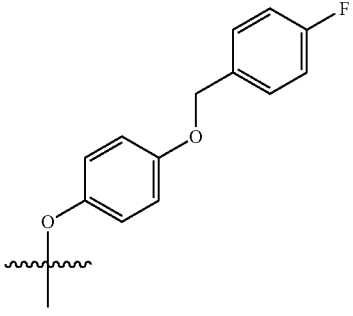 [SMILES: *Oc1ccc(OCc2ccc(F)cc2)cc1] | 10-(4-(4-fluorobenzyloxy)phenoxy)-3,4-dihydro-2H-[1,4]oxazino[2,3-f]quinazoline | 404 |

PREPARATION OF EXAMPLE COMPOUNDS

Example 1

Preparation of 1-(10-((4-(3-(trifluoromethyl)phenoxy)phenyl)amino)-2,3-dihydro-4H-[1,4]oxazino[2,3-f]quinazolin-4-yl)prop-2-en-1-one

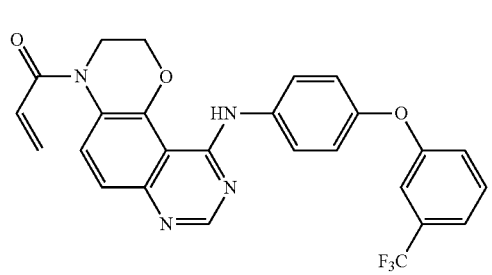 [SMILES: C=CC(=O)N1CCOc2c1ccc1ncnc(Nc3ccc(Oc4cccc(C(F)(F)F)c4)cc3)c21]

N-(4-(3-trifluoromethylphenoxy)phenyl)-3,4-dihydro-2H-[1,4]oxazino[2,3-f]quinazolin-10-amine (Intermediate No. VIII-9)(219 mg, 0.5 mmol) was dissolved in tetrahydrofuran, to which acryloyl chloride (45.3 mg, 0.5 mmol) was added, and stirred at room temperature until the reaction was completed. The reaction was quenched by adding potassium carbonate aqueous solution, extracted with ethyl acetate, and the organic phase was concentrated and purified by silica gel column chromatography to afford 196 mg of an off-white solid, with a yield of 80%. ¹H NMR (DMSO-d₆, 300 MHz) δ 9.92 (s, 1H), 8.47 (s, 1H), 8.03-7.71 (m, 3H), 7.69-7.58 (m, 1H), 7.48 (d, J=7.8 Hz, 1H), 7.38-7.23 (m, 3H), 7.24-7.03 (m, 2H), 6.92-6.69 (m, 1H), 6.43-6.18 (m, 1H), 6.00-5.76 (m, 1H), 4.68 (t, J=4.5 Hz, 2H), 4.07 (t, J=4.5 Hz, 2H); ¹³CNMR (101 MHz, DMSO-d₆) δ 158.57, 157.66, 154.56, 151.72, 149.22, 144.48, 142.80, 135.76, 131.85, 130.33, 125.24, 123.57, 122.09, 121.93, 120.45, 119.89, 119.85, 119.21, 114.25, 114.21, 106.39, 68.71, 60.34, 45.62; MS: 493[M+H]⁺.

Examples 2-42

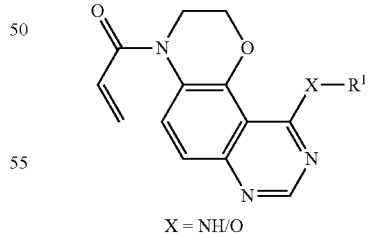

X = NH/O

With reference to the preparation method of Example 1, wherein exactly the same operations were used, and N-(4-(3-trifluoromethylphenoxy)phenyl)-3,4-dihydro-2H-[1,4]oxazino[2,3-f]quinazolin-10-amine was replaced with the same molar equivalent of intermediate represented by formula (VIII) wherein R¹X is the substituent in the table below. The specific example compounds are shown in the table below:

| Example No. | Starting Intermediate No. | R¹X | Example compounds Name | LCMS m/z = (M + H)⁺ | HNMR |
|---|---|---|---|---|---|
| 2 | VIII-1 | (4-phenoxyphenyl)amine substituent | 1-(10-((4-phenoxyphenyl)amino)-2,3-dihydro-4H-[1,4]oxazino[2,3-f]quinazolin-4-yl)prop-2-en-1-one | 425 | (400 M, DMSO-d₆) δ 9.88(s, 1H), 8.46(s, 1H), 7.81-7.79(m, 3H), 7.42-7.38(m, 2H), 7.32-7.30(m, 1H), 7.15-7.07(m, 5H), 7.03-7.01(m, 1H), 6.35-6.30(m, 1H), 5.90-5.87(m, 1H), 4.68(m, 2H), 4.07(m, 2H). |
| 3 | VIII-4 | 3-chloro-4-((3-fluorobenzyl)oxy)phenyl | 1-(10-((3-chloro-4-((3-fluorobenzyl)oxy)phenyl)amino)-2,3-dihydro-4H-[1,4]oxazino[2,3-f]quinazolin-4-yl)prop-2-en-1-one | 491 | (400 M, DMSO-d₆) δ 9.83(s, 1H), 8.47(s, 1H), 7.99(s, 1H), 7.68-7.66(m, 1H), 7.48-7.45(m, 1H), 7.34-7.25(m, 6H), 7.21-7.17(m, 1H), 6.75-6.70(m, 1H), 5.80-5.76(m, 1H), 5.28(s, 2H), 4.74-4.66(m, 2H), 4.06-3.96(m, 2H). |
| 4 | VIII-5 | 3-chloro-4-(pyridin-2-ylmethoxy)phenyl | 1-(10-((3-chloro-4-(pyridin-2-ylmethoxy)phenyl)amino)-2,3-dihydro-4H-[1,4]oxazino[2,3-f]quinazolin-4-yl)prop-2-en-1-one | 474 | (400 M, DMSO-d₆) δ 9.82(s, 1H), 8.61(s, 1H), 8.46(s, 1H), 8.01(s, 1H), 7.89-7.86(m, 1H), 7.68-7.57(m, 2H), 7.39-7.36(m, 1H), 7.32-7.25(m, 2H), 7.21-7.17(m, 1H), 6.81-6.75(m, 1H), 6.34-6.30(m, 1H), 5.90-5.87(m, 1H), 5.31(s, 2H), 4.74-4.66(m, 2H), 4.06-3.96(m, 2H). |
| 5 | VIII-2 | 4-(m-tolyloxy)phenyl | 1-(10-((4-(m-tolyloxy)phenyl)amino)-2,3-dihydro-4H-[1,4]oxazino[2,3-f]quinazolin-4-yl)prop-2-en-1-one | 439 | (300 MHz, DMSO-d₆) δ 9.87 (s, 1H), 8.45 (s, 1H), 7.82-7.70 (m, 3H), 7.39-7.20 (m, 2H), 7.06 (d, J = 8.9 Hz, 2H), 6.94 (d, J = 7.5 Hz, 1H), 6.87-6.65 (m, 3H), 6.39-6.22 (m, 1H), 6.05-5.69 (m, 1H), 4.67 (t, J = 4.6 Hz, 2H), 4.07 (t, J = 4.6 Hz, 2H), 2.29 (s, 3H). |
| 6 | VIII-10 | 4-(3-chlorophenoxy)phenyl | 1-(10-((4-(3-chlorophenoxy)phenyl)amino)-2,3-dihydro-4H-[1,4]oxazino[2,3-f]quinazolin-4-yl)prop-2-en-1-one | 459 | (300 MHz, DMSO-d₆) δ 9.90 (s, 1H), 8.46 (s, 1H), 8.04-7.68 (m, 3H), 7.49-7.37 (m, 1H), 7.32 (d, J = 9.0 Hz, 1H), 7.24-7.10 (m, 3H), 7.09-6.93 (m, 2H), 6.88-6.62 (m, 1H), 6.49-6.14 (m, 1H), 5.96-5.75 (m, 1H), 4.68 (t, J = 4.6 Hz, 2H), 4.07 (t, J = 4.5 Hz, 2H). |
| 7 | VIII-11 | 4-(3-fluorophenoxy)phenyl | 1-(10-((4-(3-fluorophenoxy)phenyl)amino)-2,3-dihydro-4H-[1,4]oxazino[2,3-f]quinazolin-4-yl)prop-2-en-1-one | 443 | (300 MHz, DMSO-d₆) δ 9.90 (s, 1H), 8.47 (s, 1H), 7.94-7.74 (m, 3H), 7.51-7.38 (m, 1H), 7.32 (d, J = 9.0 Hz, 1H), 7.15 (d, J = 8.8 Hz, 2H), 7.04-6.90 (m, 1H), 6.90-6.71 (m, 3H), 6.38-6.24 (m, 1H), 6.01-5.73 (m, 1H), 4.75-4.60 (m, 2H), 4.14-4.00 (m, 2H). |

-continued

| Example No. | Starting Intermediate No. | R¹X | Example compounds Name | LCMS m/z = (M + H)⁺ | HNMR |
|---|---|---|---|---|---|
| 8 | VIII-8 | 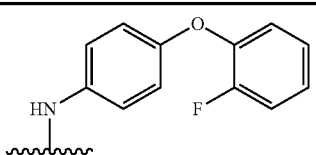 | 1-(10-((4-(2-fluorophenoxy)phenyl)amino)-2,3-dihydro-4H-[1,4]oxazino[2,3-f]quinazolin-4-yl)prop-2-en-1-one | 443 | (300 MHz, DMSO-$d_6$) δ 9.85 (s, 1H), 8.43 (s, 1H), 7.91-7.70 (m, 3H), 7.40 (s, 1H), 7.30 (d, J = 9.0 Hz, 1H), 7.27-7.11 (m, 3H), 7.04 (d, J = 8.8 Hz, 2H), 6.87-6.69 (m, 1H), 6.40-6.25 (m, 1H), 5.93-5.82 (m, 1H), 4.66 (t, J = 4.6 Hz, 2H), 4.06 (t, J = 4.6 Hz, 2H). |
| 9 | VIII-12 | 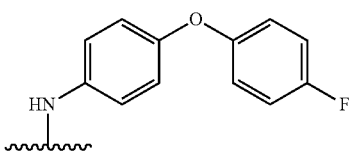 [SMILES: *Nc1ccc(Oc2ccc(F)cc2)cc1] | 1-(10-((4-(4-fluorophenoxy)phenyl)amino)-2,3-dihydro-4H-[1,4]oxazino[2,3-f]quinazolin-4-yl)prop-2-en-1-one | 443 | (300 MHz, DMSO-$d_6$) δ 9.85 (s, 1H), 8.44 (s, 1H), 7.82-7.73 (m, 3H), 7.35-7.16 (m, 3H), 7.14-7.00 (m, 4H), 6.86-6.71 (m, 1H), 6.38-6.25 (m, 1H), 5.93-5.82 (m, 1H), 4.67 (t, J = 4.6 Hz, 2H), 4.06 (t, J = 4.6 Hz, 2H). |
| 10 | VIII-13 | 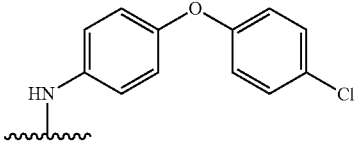 [SMILES: *Nc1ccc(Oc2ccc(Cl)cc2)cc1] | 1-(10-((4-(4-chlorophenoxy)phenyl)amino)-2,3-dihydro-4H-[1,4]oxazino[2,3-f]quinazolin-4-yl)prop-2-en-1-one | 459 | (300 MHz, DMSO-$d_6$) δ 9.89 (s, 1H), 8.56-8.36 (m, 1H), 8.03-7.62 (m, 3H), 7.44 (d, J = 8.4 Hz, 2H), 7.31 (d, J = 8.8 Hz, 1H), 7.16-6.97 (m, 4H), 6.78 (s, 1H), 6.32 (d, J = 16.7 Hz, 1H), 5.88 (d, J = 10.4 Hz, 1H), 4.77-4.57 (m, 2H), 4.17-3.95 (m, 2H). |
| 11 | VIII-14 | 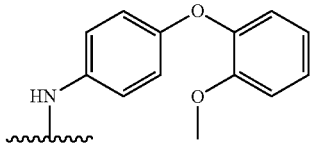 [SMILES: *Nc1ccc(Oc2ccccc2OC)cc1] | 1-(10-((4-(2-methoxyphenoxy)phenyl)amino)-2,3-dihydro-4H-[1,4]oxazino[2,3-f]quinazolin-4-yl)prop-2-en-1-one | 455 | (400 MHz, DMSO-$d_6$) δ 9.79 (s, 1H), 8.41 (s, 1H), 7.82 (s, 1H), 7.73-7.61 (m, 2H), 7.29 (d, J = 9.0 Hz, 1H), 7.24-7.16 (m, 2H), 7.10-6.97 (m, 2H), 6.93-6.87 (m, 2H), 6.86-6.71 (m, 1H), 6.39-6.27 (m, 1H), 5.96-5.83 (m, 1H), 4.66 (t, J = 4.6 Hz, 2H), 4.06 (t, J = 4.6 Hz, 2H), 3.77 (s, 3H). |
| 12 | VIII-15 | 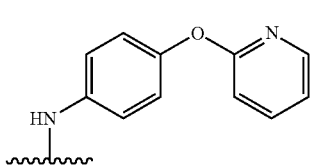 [SMILES: *Nc1ccc(Oc2ccccn2)cc1] | 1-(10-((4-(pyridin-2-yloxy)phenyl)amino)-2,3-dihydro-4H-[1,4]oxazino[2,3-f]quinazolin-4-yl)prop-2-en-1-one | 426 | (300 MHz, DMSO-$d_6$) δ 9.89 (s, 1H), 8.49-8.32 (m, 3H), 7.89-7.79 (m, 3H), 7.47-7.36 (m, 2H), 7.32 (d, J = 9.0 Hz, 1H), 7.15 (d, J = 8.8 Hz, 2H), 6.87-6.71 (m, 1H), 6.38-6.26 (m, 1H), 5.93-5.83 (m, 1H), 4.68 (t, J = 4.6 Hz, 2H), 4.07 (t, J = 4.5 Hz, 2H). |
| 13 | VIII-16 | 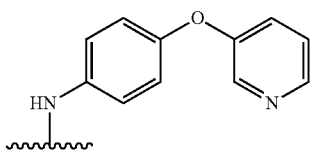 [SMILES: *Nc1ccc(Oc2cccnc2)cc1] | 1-(10-((4-(pyridin-3-yloxy)phenyl)amino)-2,3-dihydro-4H-[1,4]oxazino[2,3-f]quinazolin-4-yl)prop-2-en-1-one | 426 | (300 MHz, DMSO-$d_6$) δ 9.89 (s, 1H), 8.46 (s, 1H), 8.16 (d, J = 4.6 Hz, 1H), 7.94-7.71 (m, 4H), 7.32 (d, J = 9.1 Hz, 1H), 7.22-7.10 (m, 3H), 7.04 (d, J = 8.3 Hz, 1H), 6.91-6.62 (1H, m), 6.41-6.26 (m, 1H), 5.94-5.82 (m, 1H), 4.74-4.61 (m, 2H), 4.13-4.01 (m, 2H). |

-continued

| Example No. | Starting Intermediate No. | R¹X | Name | LCMS m/z = (M + H)⁺ | HNMR |
|---|---|---|---|---|---|
| 14 | VIII-17 | (4-methoxyphenoxy phenyl structure) | 1-(10-((4-(3-methoxyphenoxy)phenyl)amino)-2,3-dihydro-4H-[1,4]oxazino[2,3-f]quinazolin-4-yl)prop-2-en-1-one | 455 | (300 MHz, DMSO-d₆) δ 9.88 (s, 1H), 8.45 (s, 1H), 7.99-7.69 (m, 3H), 7.41-7.19 (m, 2H), 7.09 (d, J = 8.8 Hz, 2H), 6.89-6.67 (m, 2H), 6.65-6.49 (m, 2H), 6.39-6.23 (m, 1H), 5.99-5.83 (m, 1H), 4.76-4.61 (m, 2H), 4.14-3.98 (m, 2H), 3.75-3.72 (m, 3H). |
| 15 | VIII-18 | (4-(thiazol-2-yloxy)phenyl structure) | 1-(10-((4-(thiazol-2-yloxy)phenyl)amino)-2,3-dihydro-4H-[1,4]oxazino[2,3-f]quinazolin-4-yl)prop-2-en-1-one | 432 | (300 MHz, DMSO-d₆) δ 9.95 (s, 1H), 8.49 (s, 1H), 8.03-7.72 (m, 3H), 7.47-7.28 (m, 4H), 7.22 (d, J = 3.8 Hz, 1H), 6.91-6.65 (m, 1H), 6.40-6.21 (m, 1H), 5.97-5.81 (m, 1H), 4.69 (t, J = 4.6 Hz, 2H), 4.07 (t, J = 4.6 Hz, 2H). |
| 16 | VIII-7 | (3-fluoro-4-phenoxyphenyl structure) | 1-(10-((3-fluoro-4-phenoxyphenyl)amino)-2,3-dihydro-4H-[1,4]oxazino[2,3-f]quinazolin-4-yl)prop-2-en-1-one | 443 | (400 MHz, DMSO-d₆) δ 9.99 (s, 1H), 8.55 (s, 1H), 8.27-8.03 (m, 1H), 7.88 (s, 1H), 7.69-7.56 (m, 1H), 7.52-7.30 (m, 3H), 7.30-7.19 (m, 1H), 7.17-7.07 (m, 1H), 7.04-6.91 (m, 2H), 6.87-6.68 (m, 1H), 6.50-6.24 (m, 1H), 6.02-5.81 (m, 1H), 4.75-4.57 (m, 2H), 4.08 (t, J = 4.7 Hz, 2H). |
| 17 | VIII-19 | (3-chloro-4-phenoxyphenyl structure) | 1-(10-((3-chloro-4-phenoxyphenyl)amino)-2,3-dihydro-4H-[1,4]oxazino[2,3-f]quinazolin-4-yl)prop-2-en-1-one | 459 | (300 MHz, DMSO-d₆) δ 9.96 (s, 1H), 8.50 (s, 1H), 8.06-7.69 (m, 3H), 7.51-7.31 (m, 5H), 7.29-7.18 (m, 2H), 6.78 (s, 1H), 6.32 (d, J = 16.8 Hz, 1H), 5.88 (d, J = 10.7 Hz, 1H), 4.77-4.59 (m, 2H), 4.18-4.00 (m, 2H). |
| 18 | VIII-20 | (4-((4-fluorobenzyl)oxy)phenyl structure) | 1-(10-((4-((4-fluorobenzyl)oxy)phenyl)amino)-2,3-dihydro-4H-[1,4]oxazino[2,3-f]quinazolin-4-yl)prop-2-en-1-one | 457 | (300 MHz, DMSO-d₆) δ 9.76 (s, 1H), 8.40 (s, 1H), 7.80 (s, 1H), 7.72-7.61 (m, 2H), 7.59-7.46 (m, 2H), 7.36-7.15 (m, 3H), 7.04 (d, J = 8.8 Hz, 2H), 6.88-6.69 (m, 1H), 6.41-6.24 (m, 1H), 5.98-5.77 (m, 1H), 5.11 (s, 2H), 4.66 (t, J = 4.7 Hz, 2H), 4.06 (t, J = 4.6 Hz, 2H). |
| 19 | VIII-21 | (4-((3-fluorobenzyl)oxy)phenyl structure) | 1-(10-((4-((3-fluorobenzyl)oxy)phenyl)amino)-2,3-dihydro-4H-[1,4]oxazino[2,3-f]quinazolin-4-yl)prop-2-en-1-one | 457 | (300 MHz, DMSO-d₆) δ 9.78 (s, 1H), 8.40 (s, 1H), 7.81 (s, 1H), 7.65 (d, J = 8.8 Hz, 2H), 7.55-7.40 (m, 1H), 7.38-7.24 (m, 3H), 7.20-7.11 (m, 1H), 7.05 (d, J = 8.9 Hz, 2H), 6.78 (s, 1H), 6.41-6.23 (m, 1H), 5.95-5.80 (m, 1H), 5.17 (s, 2H), 4.74-4.60 (m, 2H), 4.17-4.00 (m, 2H). |

| Example No. | Starting Intermediate No. | R¹X | Example compounds Name | LCMS m/z = (M + H)⁺ | HNMR |
|---|---|---|---|---|---|
| 20 | VIII-22 | (4-((3-trifluoromethylbenzyl)oxy)phenyl with HN- attachment and CF₃ group) | 1-(10-((4-((3-trifluoromethyl benzyl)oxy) phenyl)amino)-2,3-dihydro-4H-[1,4]oxazino[2,3-f]quinazolin-4-yl)prop-2-en-1-one | 507 | (300 MHz, DMSO-d₆) δ 9.77 (s, 1H), 8.40 (s, 1H), 7.87-7.59 (m, 7H), 7.28 (d, J = 9.0 Hz, 1H), 7.07 (d, J = 8.8 Hz, 2H), 6.86-6.70 (m, 1H), 6.38-6.25 (m, 1H), 5.93-5.82 (m, 1H), 5.25 (s, 2H), 4.66 (t, J = 4.6 Hz, 2H), 4.06 (t, J = 4.7 Hz, 2H). |
| 21 | VIII-23 | (4-(pyridin-2-ylmethoxy)phenyl) | 1-(10-((4-(pyridin-2-ylmethoxy)phenyl)amino)-2,3-dihydro-4H-[1,4]oxazino[2,3-f]quinazolin-4-yl)prop-2-en-1-one | 440 | (300 MHz, DMSO-d₆) δ 9.78 (s, 1H), 8.59 (s, 1H), 7.91-7.79 (m, 2H), 7.65 (d, J = 9.9 Hz, 2H), 7.58-7.44 (m, 2H), 7.37-7.25 (m, 2H), 7.08-7.01 (m, 2H), 6.77 (s, 1H), 6.40-6.22 (m, 1H), 5.96-5.80 (m, 1H), 5.21 (s, 2H), 4.79-4.61 (m, 2H), 4.15-3.96 (m, 2H). |
| 22 | VIII-24 | (4-(thiophen-2-ylmethoxy)phenyl) | 1-(10-((4-(thiophen-2-ylmethoxy)phenyl)amino)-2,3-dihydro-4H-[1,4]oxazino[2,3-f]quinazolin-4-yl)prop-2-en-1-one | 445 | (300 MHz, DMSO-d₆) δ 9.77 (s, 1H), 8.40 (s, 1H), 7.80 (s, 1H), 7.66 (d, J = 8.8 Hz, 2H), 7.56 (d, J = 5.2 Hz, 1H), 7.36-7.18 (m, 2H), 7.13-6.98 (m, 3H), 6.88-6.69 (m, 1H), 6.41-6.26 (m, 1H), 5.97-5.82 (m, 1H), 5.32 (s, 2H), 4.70-4.61 (m, 2H), 4.12-3.97 (m, 2H). |
| 23 | VIII-25 | (4-(thiazol-2-ylmethoxy)phenyl) | 1-(10-((4-(thiazol-2-ylmethoxy)phenyl)amino)-2,3-dihydro-4H-[1,4]oxazino[2,3-f]quinazolin-4-yl)prop-2-en-1-one | 446 | (400 MHz, DMSO-d₆) δ 9.78 (s, 1H), 8.41 (s, 1H), 7.87-7.79 (m, 3H), 7.73-7.65 (m, 2H), 7.29 (d, J = 9.0 Hz, 1H), 7.14-7.07 (m, 2H), 6.85-6.73 (m, 1H), 6.38-6.27 (m, 1H), 5.92-5.83 (m, 1H), 5.47 (s, 2H), 4.67 (t, J = 4.6 Hz, 2H), 4.06 (t, J = 4.7 Hz, 2H). |
| 24 | VIII-26 | (4-(benzylthio)phenyl) | 1-(10-((4-(benzylthio)phenyl)amino)-2,3-dihydro-4H-[1,4]oxazino[2,3-f]quinazolin-4-yl)prop-2-en-1-one | 455 | (300 MHz, DMSO-d₆) δ 9.89 (s, 1H), 8.48 (s, 1H), 7.87-7.74 (m, 3H), 7.37 (d, J = 2.7 Hz, 1H), 7.39-7.17 (m, 7H), 6.86-6.70 (m, 1H), 6.38-6.25 (m, 1H), 5.93-5.82 (m, 1H), 4.67 (t, J = 4.6 Hz, 2H), 4.22 (s, 2H), 4.06 (t, J = 4.7 Hz, 2H). |
| 25 | VIII-3 | (4-((3-fluorobenzyl)oxy)-3-(trifluoromethyl)phenyl) | 1-(10-((4-((3-fluorobenzyl)oxy)-3-(trifluoromethyl)phenyl)amino)-2,3-dihydro-4H-[1,4]oxazino[2,3-f]quinazolin-4-yl)prop-2-en-1-one | 525 | (300 MHz, DMSO-d₆) δ 9.87 (s, 1H), 8.44 (s, 1H), 8.07 (d, J = 2.6 Hz, 1H), 8.02-7.91 (m, 1H), 7.84 (s, 1H), 7.55-7.41 (m, 1H), 7.37 (d, J = 9.1 Hz, 1H), 7.34-7.23 (m, 3H), 7.23-7.14 (m, 1H), 6.86-6.71 (m, 1H), 6.39-6.26 (m, 1H), 5.94-5.84 (m, 1H), 5.34 (s, 2H), 4.66 (t, J = 4.5 Hz, 2H), 4.06 (t, J = 4.5 Hz, 2H). |

| Example No. | Starting Intermediate No. | R¹X | Name | LCMS m/z = (M + H)⁺ | HNMR |
|---|---|---|---|---|---|
| 26 | VIII-27 | | 1-(10-((4-((3-fluorobenzyl)oxy)-3-(methoxy)phenyl)amino)-2,3-dihydro-4H-[1,4]oxazino[2,3-f]quinazolin-4-yl)prop-2-en-1-one | 487 | (300 MHz, DMSO-d$_6$) δ 9.76 (s, 1H), 8.43 (s, 1H), 7.81-7.79 (m, 1H), 7.59-7.37 (m, 2H), 7.36-7.25 (m, 4H), 7.16 (s, 1H), 7.04 (d, J = 8.0 Hz, 1H), 6.78-6.75 (m, 1H), 6.32 (d, J = 16.7 Hz, 1H), 5.88 (d, J = 10.2 Hz, 1H), 5.14 (s, 2H), 4.74-4.59 (m, 2H), 4.11-3.99 (m, 2H), 3.82 (s, 3H). |
| 27 | VIII-28 | | 1-(10-((4-((3-fluorobenzyl)oxy)-3-fluorophenyl)amino)-2,3-dihydro-4H-[1,4]oxazino[2,3-f]quinazolin-4-yl)prop-2-en-1-one | 475 | (300 MHz, DMSO-d$_6$) δ 9.87 (s, 1H), 8.45 (s, 1H), 7.88-7.73 (m, 2H), 7.46-7.40 (m, 2H), 7.30-7.26 (m, 4H), 7.16-7.00 (m, 1H), 6.79-6.77 (m, 1H), 6.35-6.31 (m, 1H), 5.88-5.86 (m, 1H), 5.23 (s, 2H), 4.71-4.58 (m, 2H), 4.08-4.01 (m, 2H). |
| 28 | VIII-29 | | 1-(10-((4-((4-fluorophenyl)thio)phenyl)amino)-2,3-dihydro-4H-[1,4]oxazino[2,3-f]quinazolin-4-yl)prop-2-en-1-one | 459 | (300 MHz, DMSO-d$_6$) δ 9.96 (s, 1H), 8.53 (s, 1H), 8.21 (d, J = 2.6 Hz, 1H), 7.96-7.77 (m, 2H), 7.45-7.30 (m, 3H), 7.20 (d, J = 8.8 Hz, 1H), 7.16-7.09 (m, 1H), 7.01-6.91 (m, 2H), 6.87-6.70 (m, 1H), 6.33 (d, J = 16.4 Hz, 1H), 5.89 (d, J = 10.7 Hz, 1H), 4.72-4.64 (m, 2H), 4.13-4.03 (m, 2H). |
| 29 | VIII-6 | | 1-(10-((2-fluoro-4-phenoxyphenyl)amino)-2,3-dihydro-4H-[1,4]oxazino[2,3-f]quinazolin-4-yl)prop-2-en-1-one | 443 | (400 MHz, DMSO-d$_6$) δ 10.34 (s, 1H), 8.86-8.71 (m, 1H), 8.60 (s, 1H), 7.88 (s, 1H), 7.52-7.44 (m, 2H), 7.39 (d, J = 9.1 Hz, 1H), 7.28-7.16 (m, 4H), 7.00-6.93 (m, 1H), 6.84-6.72 (m, 1H), 6.40-6.28 (m, 1H), 5.95-5.87 (m, 1H), 4.43 (t, J = 4.7 Hz, 2H), 4.04 (t, J = 4.7 Hz, 2H). |
| 30 | VIII-37 | | 1-(10-((4-(2-(2-(dimethylamino)ethoxy)phenoxy)phenyl)amino)-2,3-dihydro-4H-[1,4]oxazino[2,3-f]quinazolin-4-yl)prop-2-en-1-one | 512 | (400 MHz, Methanol-d$_4$) δ 8.44-8.22 (m, 1H), 7.98-7.49 (m, 3H), 7.48-7.21 (m, 2H), 7.19-6.97 (m, 4H), 6.92-6.65 (m, 2H), 6.47-6.31 (m, 1H), 5.95-5.77 (m, 1H), 5.06-5.00 (m, 2H), 4.13-4.02 (m, 2H), 3.30 (s, 6H), 2.35-2.19 (m, 4H). |

-continued

| Example No. | Starting Intermediate No. | R¹X | Example compounds Name | LCMS m/z = (M + H)⁺ | HNMR |
|---|---|---|---|---|---|
| 31 | VIII-38 | | 1-(10-((4-(2-(3-(dimethylamino)propoxy)phenoxy)phenyl)amino)-2,3-dihydro-4H-[1,4]oxazino[2,3-f]quinazolin-4-yl)prop-2-en-1-one | 526 | (400 MHz, Methanol-$d_4$) δ 8.44-8.28 (m, 1H), 7.89-7.57 (m, 3H), 7.27 (d, J = 9.1 Hz, 1H), 7.23-7.11 (m, 2H), 7.08-7.01 (m, 2H), 6.96 (d, J = 7.7 Hz, 1H), 6.90-6.80 (m, 2H), 6.79-6.69 (m, 1H), 6.46-6.30 (m, 1H), 5.98-5.78 (m, 1H), 4.15-4.06 (m, 2H), 4.03-3.91 (m, 2H), 3.31 (s, 6H), 2.55-2.45 (m, 2H), 2.36-2.28 (m, 4H). |
| 32 | VIII-39 | | 1-(10-((4-(2-(2-methoxyethoxy)phenoxy)phenyl)amino)-2,3-dihydro-4H-[1,4]oxazino[2,3-f]quinazolin-4-yl)prop-2-en-1-one | 499 | (400 MHz, DMSO-$d_6$) δ 9.90-9.77 (m, 1H), 8.55-8.31 (m, 1H), 7.86-7.64 (m, 3H), 7.40-7.24 (m, 2H), 7.17 (d, J = 6.6 Hz, 2H), 7.03-6.95 (m, 2H), 6.93 (d, J = 8.5 Hz, 1H), 6.78 (s, 1H), 6.32 (d, J = 16.8 Hz, 1H), 5.88 (d, J = 10.8 Hz, 1H), 4.66 (t, J = 4.8 Hz, 2H), 4.12 (t, J = 4.8 Hz, 2H), 4.06 (t, J = 4.5 Hz, 2H), 3.56 (t, J = 4.7 Hz, 2H), 3.23 (s, 3H). |
| 33 | VIII-56 | | 1-(10-(4-phenoxyphenoxy)-2,3-dihydro-4H-[1,4]oxazino[2,3-f]quinazolin-4-yl)prop-2-en-1-one | 426 | (300 MHz, DMSO-$d_6$) δ 8.60 (s, 1H), 8.03 (s, 1H), 7.53-7.39 (m, 3H), 7.28 (d, J = 8.6 Hz, 2H), 7.20-7.04 (m, 5H), 6.80 (s, 1H), 6.33 (d, J = 17.0 Hz, 1H), 5.89 (d, J = 10.7 Hz, 1H), 4.64-4.51 (m, 2H), 4.14-3.98 (m, 2H). |
| 34 | VIII-54 | | 1-(10-(3-chloro-4-(pyridin-2-ylmethoxy)phenoxy)-2,3-dihydro-4H-[1,4]oxazino[2,3-f]quinazolin-4-yl)prop-2-en-1-one | 475 | (400 MHz, DMSO-$d_6$) δ 8.68-8.53 (m, 2H), 8.13-7.95 (m, 1H), 7.94-7.85 (m, 1H), 7.61 (d, J = 7.8 Hz, 1H), 7.57-7.45 (m, 2H), 7.43-7.35 (m, 1H), 7.32 (d, J = 8.9 Hz, 1H), 7.26-7.19 (m, 1H), 6.87-6.74 (m, 1H), 6.39-6.28 (m, 1H), 5.93-5.86 (m, 1H), 5.33 (s, 2H), 4.54 (t, J = 4.5 Hz, 2H), 4.05 (t, J = 4.5 Hz, 2H). |

-continued

| Example No. | Starting Intermediate No. | R¹X | Name | LCMS m/z = (M + H)⁺ | HNMR |
|---|---|---|---|---|---|
| 35 | VIII-55 | 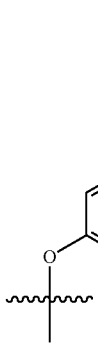 | 1-(10-(3-chloro-4-((3-fluorobenzyl)oxy)phenoxy)-2,3-dihydro-4H-[1,4]oxazino[2,3-f]quinazolin-4-yl)prop-2-en-1-one | 492 | (400 MHz, DMSO-d₆) δ 8.58 (s, 1H), 8.02 (s, 1H), 7.56-7.43 (m, 3H), 7.41-7.27 (m, 3H), 7.27-7.14 (m, 2H), 6.84-6.73 (m, 1H), 6.39-6.24 (m, 1H), 5.97-5.80 (m, 1H), 5.29 (s, 2H), 4.53 (t, J = 4.6 Hz, 2H), 4.05 (t, J = 4.6 Hz, 2H). |
| 36 | VIII-57 | 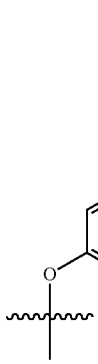 | 1-(10-(4-(4-chlorophenoxy)phenoxy)-2,3-dihydro-4H-[1,4]oxazino[2,3-f]quinazolin-4-yl)prop-2-en-1-one | 460 | (400 MHz, DMSO-d₆) δ 8.59 (s, 1H), 8.02 (s, 1H), 7.51-7.45 (m, 3H), 7.32-7.27 (m, 2H), 7.17-7.12 (m, 2H), 7.11-7.07 (m, 2H), 6.85-6.74 (m, 1H), 6.37-6.29 (m, 1H), 5.92-5.88 (m, 1H), 4.54 (t, J = 4.4 Hz, 2H), 4.05 (t, J = 4.4 Hz, 2H). |
| 37 | VIII-58 | 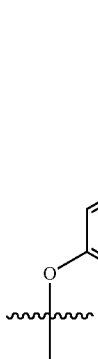 | 1-(10-(4-(4-fluorophenoxy)phenoxy)-2,3-dihydro-4H-[1,4]oxazino[2,3-f]quinazolin-4-yl)prop-2-en-1-one | 444 | (400 MHz, DMSO-d₆) δ 8.59 (s, 1H), 8.02 (s, 1H), 7.49 (d, J = 9.1 Hz, 1H), 7.43-7.19 (m, 4H), 7.19-7.01 (m, 4H), 6.85-6.76 (m, 1H), 6.41-6.26 (m, 1H), 5.95-5.81 (m, 1H), 4.54 (t, J = 4.6 Hz, 2H), 4.05 (t, J = 4.7 Hz, 2H). |
| 38 | VIII-59 | 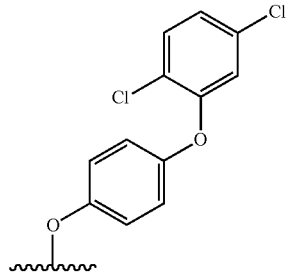 [SMILES: *Oc1ccc(Oc2cc(Cl)ccc2Cl)cc1] | 1-(10-(4-(2,5-dichlorophenoxy)phenoxy)-2,3-dihydro-4H-[1,4]oxazino[2,3-f]quinazolin-4-yl)prop-2-en-1-one | 494 | (400 MHz, DMSO-d₆) δ 8.59 (s, 1H), 8.01 (s, 1H), 7.82-7.78 (m, 1H), 7.51-7.46 (m, 2H), 7.31-7.27 (m, 2H), 7.20-7.16 (m, 1H), 7.11-7.07 (m, 2H), 6.84-6.75 (m, 1H), 6.36-6.29 (m, 1H), 5.92-5.86 (m, 1H), 4.54 (t, J = 4.4 Hz, 2H), 4.05 (t, J = 4.4 Hz, 2H). |

-continued

| Example No. | Starting Intermediate No. | R¹X | Example compounds | | |
|---|---|---|---|---|---|
| | | | Name | LCMS m/z = (M + H)⁺ | HNMR |
| 39 | VIII-60 | 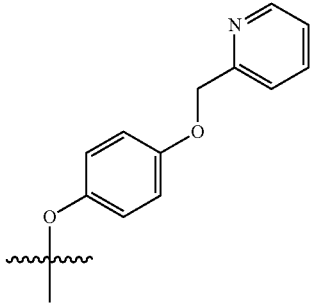 [SMILES: *Oc1ccc(OCc2ccccn2)cc1] | 1-(10-(4-(pyridin-2-ylmethoxy)phenoxy)-2,3-dihydro-4H-[1,4]oxazino[2,3-f]quinazolin-4-yl)prop-2-en-1-one | 441 | (400 MHz, DMSO-d$_6$) δ 8.61-8.59 (m, 1H), 8.55 (s, 1H), 8.08-7.93 (m, 1H), 7.89-7.84 (m, 1H), 7.58-7.54 (m, 1H), 7.50-7.46 (m, 1H), 7.39-7.34 (m, 1H), 7.19-7.16 (m, 2H), 7.13-7.08 (m, 2H), 6.85-6.74 (m, 1H), 6.33 (d, J = 16.4 Hz, 1H), 5.91-5.86 (m, 1H), 5.22 (s, 2H), 4.53 (t, J = 4.8 Hz, 2H), 4.05 (t, J = 4.8 Hz, 2H). |
| 40 | VIII-61 | 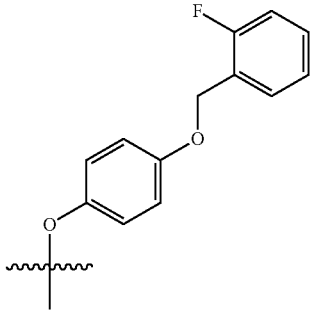 [SMILES: *Oc1ccc(OCc2ccccc2F)cc1] | 1-(10-(4-((2-fluorobenzyl)oxy)phenoxy)-2,3-dihydro-4H-[1,4]oxazino[2,3-f]quinazolin-4-yl)prop-2-en-1-one | 458 | (400 MHz, DMSO-d$_6$) δ 8.56 (s, 1H), 8.01 (s, 1H), 7.63-7.57 (m, 1H), 7.50-7.46 (m, 1H), 7.46-7.41 (m, 1H), 7.31-7.24 (m, 2H), 7.21-7.17 (m, 2H), 7.14-7.09 (m, 2H), 6.86-6.74 (m, 1H), 6.38-6.29 (m, 1H), 5.92-5.86 (m, 1H), 5.18 (s, 2H), 4.58-4.51 (m, 2H), 4.09-4.01 (m, 2H). |
| 41 | VIII-62 | 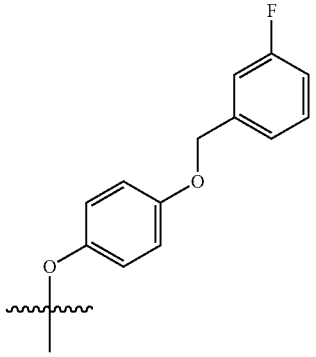 [SMILES: *Oc1ccc(OCc2cccc(F)c2)cc1] | 1-(10-(4-((3-fluorobenzyl)oxy)phenoxy)-2,3-dihydro-4H-[1,4]oxazino[2,3-f]quinazolin-4-yl)prop-2-en-1-one | 458 | (400 MHz, DMSO-d$_6$) δ 8.55 (s, 1H), 7.99 (s, 1H), 7.50-7.42 (m, 2H), 7.35-7.29 (m, 2H), 7.20-7.14 (m, 3H), 7.11-7.07 (m, 2H), 6.86-6.71 (m, 1H), 6.37-6.27 (m, 1H), 5.92-5.84 (m, 1H), 5.18 (s, 2H), 4.56-4.49 (m, 2H), 4.08-4.00 (m, 2H). |
| 42 | VIII-63 | 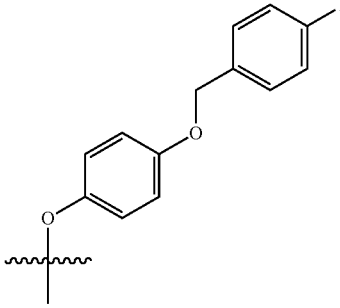 | 1-(10-(4-((4-fluorobenzyl)oxy)phenoxy)-2,3-dihydro-4H-[1,4]oxazino[2,3-f]quinazolin-4-yl)prop-2-en-1-one | 458 | (400 MHz, DMSO-d$_6$) δ 8.55 (s, 1H), 8.00 (s, 1H), 7.56-7.51 (m, 2H), 7.50-7.45 (m, 1H), 7.27-7.20 (m, 2H), 7.19-7.14 (m, 2H), 7.11-7.05 (m, 2H), 6.85-6.72 (m, 1H), 6.36-6.27 (m, 1H), 5.93-5.84 (m, 1H), 5.13 (s, 2H), 4.53 (t, J = 4.4 Hz, 2H), 4.05 (t, J = 4.4 Hz, 2H). |

Example 43

Preparation of (E)-4-(dimethylamino)-1-(10-((4-(3-(trifluoromethyl)phenoxy)phenyl)amino)-2,3-dihydro-4H-[1,4]oxazino[2,3-f]quinazolin-4-yl)but-2-en-1-one

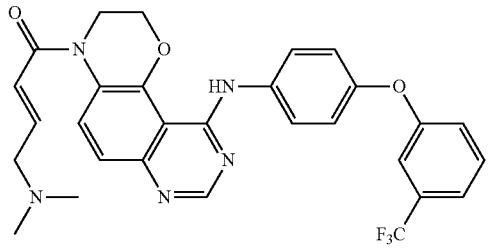 [SMILES: CN(C)C/C=C/C(=O)N1CCOc2c1ccc1ncnc(Nc3ccc(Oc4cccc(C(F)(F)F)c4)cc3)c21]

N-(4-(3-trifluoromethylphenoxy)phenyl)-3,4-dihydro-2H-[1,4]oxazino[2,3-f]quinazolin-10-amine (VIII-9) (219 mg, 0.5 mmol) was dissolved in a mixed solvent of tetrahydrofuran and dimethylformamide, and trans-4-dimethylaminocrotonic acid hydrochloride (92 mg, 0.5 mmol) was added, and stirred at room temperature until the reaction was completed. The reaction was quenched by adding potassium carbonate aqueous solution, extracted with ethyl acetate, the organic phase was concentrated and purified by silica gel column chromatography to afford 208 mg of an off-white solid with a yield of 76%. $^1$H NMR (400 MHz, DMSO-$d_6$) δ 9.92 (s, 1H), 8.48 (s, 1H), 7.93-7.84 (m, 3H), 7.66-7.58 (m, 1H), 7.48 (d, J=7.8 Hz, 1H), 7.35-7.25 (m, 3H), 7.23-7.14 (m, 2H), 6.88-6.76 (m, 1H), 6.58 (d, J=15.2 Hz, 1H), 4.68 (t, J=4.6 Hz, 2H), 4.06 (t, J=4.6 Hz, 2H), 3.12-3.05 (m, 2H), 2.18 (s, 6H); $^{13}$CNMR (101 MHz, DMSO-d6) δ 158.57, 157.66, 154.56, 151.72, 149.22, 144.48, 142.80, 135.76, 131.85, 130.33, 125.24, 123.57, 122.09, 121.93, 120.45, 119.89, 119.85, 119.21, 114.25, 114.21, 106.39, 68.71, 60.34, 45.62; MS: 550[M+H]$^+$.

Examples 44-90

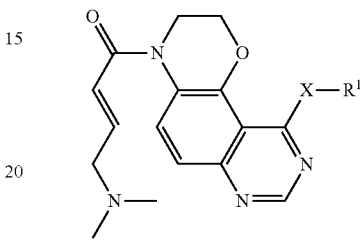

With reference to the preparation method of Example 43, wherein exactly the same operations were used, and N-(4-(3-trifluoromethylphenoxy)phenyl)-3,4-dihydro-2H-[1,4]oxazino[2,3-f]quinazolin-10-amine (VIII-9) was replaced with the same molar equivalent of intermediate represented by formula (VIII) wherein R$^1$X is the substituent in the table below. The specific example compounds are shown in the table below:

| | | | Example compounds | | |
|---|---|---|---|---|---|
| Example No. | Starting Intermediate No. | R$^1$X | Name | LCMS m/z = (M + H)$^+$ | HNMR |
| 44 | VIII-1 | ![structure] | (E)-4-(dimethylamino)-1-(10-((4-phenoxyphenyl)amino)-2,3-dihydro-4H-[1,4]oxazino[2,3-f]quinazolin-4-yl)but-2-en-1-one | 482 | (400 M, CDCl$_3$) δ9.56(s, 1H), 8.62(s, 1H), 7.71-7.68(m, 2H), 7.61(brs, 1H), 7.47-7.45(m, 1H), 7.38-7.34(m, 2H), 7.14-7.05(m, 6H), 6.72-6.64(m, 1H), 4.72-4.66(m, 2H), 4.24-4.18(m, 2H), 3.38-3.31(m, 2H), 2.46(s, 6H) |
| 45 | VIII-4 | ![structure] | (E)-1-(10-((3-chloro-4-((3-fluorobenzyl)oxy)phenyl)amino)-2,3-dihydro-4H-[1,4]oxazino[2,3-f]quinazolin-4-yl)-4-(dimethylamino)but-2-en-1-one | 548 | (400 MHz, DMSO-d$_6$) δ 9.82 (s, 1H), 8.46 (s, 1H), 8.01 (d, J = 2.5 Hz, 1H), 7.83 (s, 1H), 7.71-7.63 (m, 1H), 7.53-7.43 (m, 1H), 7.37-7.22 (m, 4H), 7.21-7.12 (m, 1H), 6.89-6.74 (m, 1H), 6.58 (d, J = 15.3 Hz, 1H), 5.27 (s, 2H), 4.66 (t, J = 4.6 Hz, 2H), 4.05 (t, J = 4.6 Hz, 2H), 3.10 (d, J = 5.8 Hz, 2H), 2.19 (s, 6H). |

-continued

| Example No. | Starting Intermediate No. | R¹X | Example compounds Name | LCMS m/z = (M + H)⁺ | HNMR |
|---|---|---|---|---|---|
| 46 | VIII-5 | (structure: 3-chloro-4-(pyridin-2-ylmethoxy)phenyl amine) | (E)-1-(10-((3-chloro-4-(pyridin-2-ylmethoxy)phenyl)amino)-2,3-dihydro-4H-[1,4]oxazino[2,3-f]quinazolin-4-yl)-4-(dimethylamino)but-2-en-1-one | 531 | (400 MHz, DMSO-$d_6$) δ 9.81 (s, 1H), 8.64-8.58 (m, 1H), 8.46 (s, 1H), 8.01 (d, J = 2.6 Hz, 1H), 7.92-7.75 (m, 2H), 7.71-7.63 (m, 1H), 7.58 (d, J = 7.9 Hz, 1H), 7.42-7.34 (m, 1H), 7.34-7.22 (m, 2H), 6.87-6.76 (m, 1H), 6.58 (d, J = 15.2 Hz, 1H), 5.31 (s, 2H), 4.66 (t, J = 4.6 Hz, 2H), 4.05 (t, J = 4.6 Hz, 2H), 3.09 (d, J = 5.8 Hz, 2H), 2.19 (s, 6H). |
| 47 | VIII-2 | (structure: 4-(m-tolyloxy)phenyl amine) | (E)-4-(dimethylamino)-1-(10-((4-(m-tolyloxy)phenyl)amino)-2,3-dihydro-4H-[1,4]oxazino[2,3-f]quinazolin-4-yl)but-2-en-1-one | 496 | (400 MHz, DMSO-$d_6$) δ 9.87 (s, 1H), 8.45 (s, 1H), 7.89-7.76 (m, 3H), 7.34-7.23 (m, 2H), 7.11-7.04 (m, 2H), 6.98-6.92 (m, 1H), 6.86-6.77 (m, 3H), 6.58 (d, J = 15.4 Hz, 1H), 4.72-4.66 (m, 2H), 4.12-4.02 (m, 2H), 3.12-3.04 (m, 2H), 2.30 (s, 3H), 2.18 (s, 6H). |
| 48 | VIII-10 | (structure: 4-(3-chlorophenoxy)phenyl amine) | (E)-4-(dimethylamino)-1-(10-((4-(3-chlorophenoxy)phenyl)amino)-2,3-dihydro-4H-[1,4]oxazino[2,3-f]quinazolin-4-yl)but-2-en-1-one | 516 | (400 MHz, DMSO-$d_6$) δ 9.90 (s, 1H), 8.47 (s, 1H), 7.90-7.82 (m, 3H), 7.42 (t, J = 8.1 Hz, 1H), 7.31 (d, J = 9.0 Hz, 1H), 7.22-7.11 (m, 3H), 7.07-6.94 (m, 2H), 6.88-6.76 (m, 1H), 6.59 (d, J = 15.3 Hz, 1H), 4.67 (t, J = 4.6 Hz, 2H), 4.06 (t, J = 4.6 Hz, 2H), 3.11 (d, J = 5.7 Hz, 2H), 2.20 (s, 6H). |
| 49 | VIII-11 | (structure: 4-(3-fluorophenoxy)phenyl amine) | (E)-4-(dimethylamino)-1-(10-((4-(3-fluorophenoxy)phenyl)amino)-2,3-dihydro-4H-[1,4]oxazino[2,3-f]quinazolin-4-yl)but-2-en-1-one | 500 | (400 MHz, DMSO-$d_6$) δ 9.90 (s, 1H), 8.47 (s, 1H), 7.93-7.74 (m, 3H), 7.46-7.38 (m, 1H), 7.31 (d, J = 9.0 Hz, 1H), 7.18-7.12 (m, 2H), 6.99-6.93 (m, 1H), 6.89-6.77 (m, 3H), 6.59 (d, J = 15.3 Hz, 1H), 4.72-4.64 (m, 2H), 4.06 (t, J = 4.7 Hz, 2H), 3.13-3.05 (m, 2H), 2.18 (s, 6H). |

| Example No. | Starting Intermediate No. | R¹X | Name | LCMS m/z = (M + H)⁺ | HNMR |
|---|---|---|---|---|---|
| 50 | VIII-8 | (4-(2-fluorophenoxy)phenyl with HN linker) | (E)-4-(dimethylamino)-1-(10-((4-(2-fluorophenoxy)phenyl)amino)-2,3-dihydro-4H-[1,4]oxazino[2,3-f]quinazolin-4-yl)but-2-en-1-one | 500 | (400 MHz, DMSO-d₆) δ 9.85 (s, 1H), 8.44 (s, 1H), 7.77 (d, J = 8.9 Hz, 3H), 7.46-7.36 (m, 1H), 7.30 (d, J = 9.0 Hz, 1H), 7.27-7.21 (m, 2H), 7.20-7.13 (m, 1H), 7.04 (d, J = 8.8 Hz, 2H), 6.87-6.77 (m, 1H), 6.58 (d, J = 15.3 Hz, 1H), 4.66 (t, J = 4.6 Hz, 2H), 4.05 (t, J = 4.6 Hz, 2H), 3.10-3.04 (m, 2H), 2.17 (s, 6H). |
| 51 | VIII-12 | (4-(4-fluorophenoxy)phenyl with HN linker) | (E)-4-(dimethylamino)-1-(10-((4-(4-fluorophenoxy)phenyl)amino)-2,3-dihydro-4H-[1,4]oxazino[2,3-f]quinazolin-4-yl)but-2-en-1-one | 500 | (400 MHz, DMSO-d₆) δ 9.86 (s, 1H), 8.45 (s, 1H), 7.89-7.76 (m, 3H), 7.30 (d, J = 9.0 Hz, 1H), 7.28-7.19 (m, 2H), 7.13-7.01 (m, 4H), 6.89-6.77 (m, 1H), 6.58 (d, J = 15.3 Hz, 1H), 4.67 (t, J = 4.6 Hz, 2H), 4.05 (t, J = 4.6 Hz, 2H), 3.08 (d, J = 5.8 Hz, 2H), 2.18 (s, 6H). |
| 52 | VIII-13 | (4-(4-chlorophenoxy)phenyl with HN linker) | (E)-4-(dimethylamino)-1-(10-((4-(4-chlorophenoxy)phenyl)amino)-2,3-dihydro-4H-[1,4]oxazino[2,3-f]quinazolin-4-yl)but-2-en-1-one | 516 | (400 MHz, DMSO-d₆) δ 9.88 (s, 1H), 8.46 (s, 1H), 7.89-7.77 (m, 3H), 7.48-7.40 (m, 2H), 7.31 (d, J = 9.0 Hz, 1H), 7.15-7.08 (m, 2H), 7.08-7.01 (m, 2H), 6.86-6.77 (m, 1H), 6.58 (d, J = 15.2 Hz, 1H), 4.67 (t, J = 4.6 Hz, 2H), 4.06 (t, J = 4.7 Hz, 2H), 3.12-3.04 (m, 2H), 2.18 (s, 6H). |
| 53 | VIII-14 | (4-(2-methoxyphenoxy)phenyl with HN linker) | (E)-4-(dimethylamino)-1-(10-((4-(2-methoxyphenoxy)phenyl)amino)-2,3-dihydro-4H-[1,4]oxazino[2,3-f]quinazolin-4-yl)but-2-en-1-one | 512 | (400 MHz, DMSO-d₆) δ 9.79 (s, 1H), 8.41 (s, 1H), 7.83 (s, 1H), 7.72-7.63 (m, 2H), 7.29 (d, J = 9.0 Hz, 1H), 7.25-7.16 (m, 2H), 7.08-7.03 (m, 1H), 7.03-6.95 (m, 1H), 6.95-6.87 (m, 2H), 6.87-6.76 (m, 1H), 6.57 (d, J = 15.3 Hz, 1H), 4.69-4.61 (m, 2H), 4.05 (t, J = 4.7 Hz, 2H), 3.77 (s, 3H), 3.11-3.04 (m, 2H), 2.17 (s, 6H). |

-continued

| Example No. | Starting Intermediate No. | R¹X | Example compounds Name | LCMS m/z = (M + H)⁺ | HNMR |
|---|---|---|---|---|---|
| 54 | VIII-15 | HN—(4-phenyl)—O—(pyridin-2-yl) | (E)-4-(dimethylamino)-1-(10-((4-(pyridin-2-yloxy)phenyl)amino)-2,3-dihydro-4H-[1,4]oxazino[2,3-f]quinazolin-4-yl)but-2-en-1-one | 483 | (400 MHz, DMSO-d₆) δ 9.90 (s, 1H), 8.47 (s, 1H), 8.45 (t, J = 1.8 Hz, 1H), 8.36 (t, J = 3.0 Hz, 1H), 7.85 (d, J = 8.8 Hz, 3H), 7.43 (t, J = 2.3 Hz, 2H), 7.31 (d, J = 9.0 Hz, 1H), 7.15 (d, J = 8.8 Hz, 2H), 6.88-6.76 (m, 1H), 6.58 (d, J = 15.3 Hz, 1H), 4.67 (t, J = 4.7 Hz, 2H), 4.06 (t, J = 4.7 Hz, 2H), 3.08 (d, J = 5.9 Hz, 2H), 2.18 (s, 6H). |
| 55 | VIII-16 | HN—(4-phenyl)—O—(pyridin-3-yl) | (E)-4-(dimethylamino)-1-(10-((4-(pyridin-3-yloxy)phenyl)amino)-2,3-dihydro-4H-[1,4]oxazino[2,3-f]quinazolin-4-yl)but-2-en-1-one | 483 | (400 MHz, DMSO-d₆) δ 9.89 (s, 1H), 8.47 (s, 1H), 8.19-8.13 (m, 1H), 7.90-7.83 (m, 2H), 7.83-7.78 (m, 2H), 7.31 (d, J = 9.0 Hz, 1H), 7.19-7.15 (m, 2H), 7.15-7.11 (m, 1H), 7.04 (d, J = 8.3 Hz, 1H), 6.86-6.78 (m, 1H), 6.58 (d, J = 15.3 Hz, 1H), 4.68 (t, J = 4.6 Hz, 2H), 4.06 (t, J = 4.6 Hz, 2H), 3.08 (d, J = 5.8 Hz, 2H), 2.18 (s, 6H). |
| 56 | VIII-17 | HN—(4-phenyl)—O—(3-methoxyphenyl) | (E)-4-(dimethylamino)-1-(10-((4-(3-methoxyphenoxy)phenyl)amino)-2,3-dihydro-4H-[1,4]oxazino[2,3-f]quinazolin-4-yl)but-2-en-1-one | 512 | (400 MHz, DMSO-d₆) δ 9.87 (s, 1H), 8.46 (s, 1H), 7.96-7.74 (m, 3H), 7.35-7.24 (m, 2H), 7.15-7.03 (m, 2H), 6.89-6.75 (m, 1H), 6.74-6.69 (m, 1H), 6.63-6.52 (m, 3H), 4.72-4.66 (m, 2H), 4.06 (t, J = 4.6 Hz, 2H), 3.75 (s, 3H), 3.12-3.04 (m, 2H), 2.18 (s, 6H). |
| 57 | VIII-18 | HN—(4-phenyl)—O—(thiazol-2-yl) | (E)-4-(dimethylamino)-1-(10-((4-(thiazol-2-yloxy)phenyl)amino)-2,3-dihydro-4H-[1,4]oxazino[2,3-f]quinazolin-4-yl)but-2-en-1-one | 489 | (400 MHz, DMSO-d₆) δ 9.95 (s, 1H), 8.49 (s, 1H), 7.96-7.82 (m, 3H), 7.40 (d, J = 8.9 Hz, 2H), 7.36-7.28 (m, 2H), 7.23 (d, J = 3.8 Hz, 1H), 6.88-6.76 (m, 1H), 6.64-6.54 (m, 1H), 4.68 (t, J = 4.6 Hz, 2H), 4.06 (t, J = 4.6 Hz, 2H), 3.08 (d, J = 5.8 Hz, 2H), 2.18 (s, 6H). |

-continued

| Example No. | Starting Intermediate No. | R¹X | Name | LCMS m/z = (M + H)⁺ | HNMR |
|---|---|---|---|---|---|
| 58 | VIII-7 | (structure: HN-phenyl-F-O-phenyl) | (E)-4-(dimethylamino)-1-(10-((3-fluoro-4-phenoxyphenyl)amino)-2,3-dihydro-4H-[1,4]oxazino[2,3-f]quinazolin-4-yl)but-2-en-1-one | 500 | (400 MHz, Methanol-$d_4$) δ 8.51 (s, 1H), 8.32 (s, 1H), 8.05-8.01 (m, 1H), 7.88-7.82 (m, 1H), 7.75-7.72 (m, 1H), 7.51-7.45 (m, 1H), 7.27-7.21 (m, 2H), 7.18-7.14 (m, 2H), 6.94-6.87 (m, 2H), 6.70-6.64 (m, 1H), 4.74 (d, J = 4.8 Hz, 2H), 4.17 (t, J = 4.8 Hz, 2H), 3.23-3.19 (m, 2H), 2.33 (s, 6H). |
| 59 | VIII-19 | (structure: HN-phenyl-Cl-O-phenyl) | (E)-4-(dimethylamino)-1-(10-((3-chloro-4-phenoxyphenyl)amino)-2,3-dihydro-4H-[1,4]oxazino[2,3-f]quinazolin-4-yl)but-2-en-1-one | 516 | (400 MHz, DMSO-$d_6$) δ 9.95 (s, 1H), 8.53 (s, 1H), 8.21 (d, J = 2.6 Hz, 1H), 7.94-7.76 (m, 2H), 7.45-7.36 (m, 2H), 7.33 (d, J = 9.0 Hz, 1H), 7.20 (d, J = 8.8 Hz, 1H), 7.12 (t, J = 7.4 Hz, 1H), 7.00-6.91 (m, 2H), 6.86-6.80 (m, 1H), 6.62-6.56 (m, 1H), 4.68 (t, J = 4.5 Hz, 2H), 4.06 (t, J = 4.6 Hz, 2H), 3.14-3.06 (m, 2H), 2.18 (s, 6H). |
| 60 | VIII-20 | (structure: HN-phenyl-O-CH2-phenyl-F) | (E)-4-(dimethylamino)-1-(10-((4-((4-fluorobenzyl)oxy)phenyl)amino)-2,3-dihydro-4H-[1,4]oxazino[2,3-f]quinazolin-4-yl)but-2-en-1-one | 514 | (400 MHz, DMSO-$d_6$) δ 9.76 (s, 1H), 8.41 (s, 1H), 7.90-7.72 (m, 1H), 7.70-7.62 (m, 2H), 7.57-7.49 (m, 2H), 7.32-7.20 (m, 3H), 7.10-7.02 (m, 2H), 6.87-6.76 (m, 1H), 6.57 (d, J = 15.3 Hz, 1H), 5.12 (s, 2H), 4.66 (t, J = 4.7 Hz, 2H), 4.05 (t, J = 4.6 Hz, 2H), 3.11-3.04 (m, 2H), 2.18 (s, 6H). |
| 61 | VIII-21 | (structure: HN-phenyl-O-CH2-phenyl-F) | (E)-4-(dimethylamino)-1-(10-((4-((3-fluorobenzyl)oxy)phenyl)amino)-2,3-dihydro-4H-[1,4]oxazino[2,3-f]quinazolin-4-yl)but-2-en-1-one | 514 | (400 MHz, DMSO-$d_6$) δ 9.76 (s, 1H), 8.40 (s, 1H), 7.80 (s, 1H), 7.70-7.63 (m, 2H), 7.51-7.40 (m, 1H), 7.35-7.24 (m, 3H), 7.22-7.12 (m, 1H), 7.06 (d, J = 8.9 Hz, 2H), 6.87-6.75 (m, 1H), 6.57 (d, J = 15.2 Hz, 1H), 5.17 (s, 2H), 4.65 |

-continued

| Example No. | Starting Intermediate No. | R¹X | Example compounds Name | LCMS m/z = (M + H)⁺ | HNMR |
|---|---|---|---|---|---|
| | | | | | (t, J = 4.6 Hz, 2H), 4.04 (t, J = 4.6 Hz, 2H), 3.11-3.04 (m, 2H), 2.17 (s, 6H). |
| 62 | VIII-22 | (4-trifluoromethylbenzyloxy phenyl with CF₃) | (E)-4-(dimethylamino)-1-(10-((4-((3-(trifluoromethylbenzyl)oxy)phenyl)amino)-2,3-dihydro-4H-[1,4]oxazino[2,3-f]quinazolin-4-yl)but-2-en-1-one | 564 | (400 MHz, DMSO-d₆) δ 9.77 (s, 1H), 8.41 (s, 1H), 7.86-7.76 (m, 3H), 7.75-7.61 (m, 4H), 7.28 (d, J = 9.0 Hz, 1H), 7.08 (d, J = 8.9 Hz, 2H), 6.87-6.75 (m, 1H), 6.57 (d, J = 15.3 Hz, 1H), 5.25 (s, 2H), 4.65 (t, J = 4.6 Hz, 2H), 4.05 (t, J = 4.6 Hz, 2H), 3.08 (d, J = 5.8 Hz, 2H), 2.18 (s, 6H). |
| 63 | VIII-23 | (pyridin-2-ylmethoxy phenyl) | (E)-4-(dimethylamino)-1-(10-((4-(pyridin-2-ylmethoxy)phenyl)amino)-2,3-dihydro-4H-[1,4]oxazino[2,3-f]quinazolin-4-yl)but-2-en-1-one | 497 | (400 MHz, DMSO-d₆) δ 9.76 (s, 1H), 8.63-8.56 (m, 1H), 8.40 (s, 1H), 7.90-7.80 (m, 1H), 7.80 (s, 1H), 7.66 (d, J = 8.9 Hz, 2H), 7.54 (d, J = 7.9 Hz, 1H), 7.40-7.32 (m, 1H), 7.28 (d, J = 8.9 Hz, 1H), 7.07 (d, J = 8.9 Hz, 2H), 6.87-6.75 (m, 1H), 6.57 (d, J = 15.3 Hz, 1H), 5.21 (s, 2H), 4.65 (t, J = 4.7 Hz, 2H), 4.04 (t, J = 4.6 Hz, 2H), 3.08 (d, J = 5.8 Hz, 2H), 2.17 (s, 6H). |
| 64 | VIII-24 | (thiophen-2-ylmethoxy phenyl) | (E)-4-(dimethylamino)-1-(10-((4-(thiophen-2-ylmethoxy)phenyl)amino)-2,3-dihydro-4H-[1,4]oxazino[2,3-f]quinazolin-4-yl)but-2-en-1-one | 502 | (400 MHz, DMSO-d₆) δ 9.77 (s, 1H), 8.41 (s, 1H), 7.80 (s, 1H), 7.72-7.64 (m, 2H), 7.59-7.53 (m, 1H), 7.28 (d, J = 9.0 Hz, 1H), 7.26-7.21 (m, 1H), 7.11-7.01 (m, 3H), 6.86-6.76 (m, 1H), 6.57 (d, J = 15.1 Hz, 1H), 5.32 (s, 2H), 4.69-4.62 (m, 2H), 4.09-4.02 (m, 2H), 3.11-3.04 (m, 2H), 2.17 (s, 6H). |

-continued

| Example No. | Starting Intermediate No. | R¹X | Example compounds Name | LCMS m/z = (M + H)⁺ | HNMR |
|---|---|---|---|---|---|
| 65 | VIII-25 | (4-(thiazol-2-ylmethoxy)phenyl)amino structure | (E)-4-(dimethylamino)-1-(10-((4-(thiazol-2-ylmethoxy)phenyl)amino)-2,3-dihydro-4H-[1,4]oxazino[2,3-f]quinazolin-4-yl)but-2-en-1-one | 503 | (400 MHz, DMSO-d₆) δ 9.78 (s, 1H), 8.41 (s, 1H), 7.86-7.79 (m, 3H), 7.74-7.65 (m, 2H), 7.28 (d, J = 9.0 Hz, 1H), 7.14-7.07 (m, 2H), 6.87-6.75 (m, 1H), 6.57 (d, J = 15.3 Hz, 1H), 5.47 (s, 2H), 4.66 (t, J = 4.7 Hz, 2H), 4.05 (t, J = 4.7 Hz, 2H), 3.07 (d, J = 5.5 Hz, 2H), 2.17 (s, 6H). |
| 66 | VIII-26 | (4-(benzylthio)phenyl)amino structure | (E)-4-(dimethylamino)-1-(10-((4-(benzylthio)phenyl)amino)-2,3-dihydro-4H-[1,4]oxazino[2,3-f]quinazolin-4-yl)but-2-en-1-one | 512 | (400 MHz, DMSO-d₆) δ 9.89 (s, 1H), 8.48 (s, 1H), 7.91-7.76 (m, 3H), 7.42-7.20 (m, 8H), 6.89-6.75 (m, 1H), 6.58 (d, J = 15.3 Hz, 1H), 4.67 (t, J = 4.6 Hz, 2H), 4.23 (s, 2H), 4.05 (t, J = 4.6 Hz, 2H), 3.12-3.00 (m, 2H), 2.18 (s, 6H). |
| 67 | VIII-3 | (4-((3-fluorobenzyl)oxy)-3-(trifluoromethyl)phenyl)amino structure | (E)-4-(dimethylamino)-1-(10-((4-((3-fluorobenzyl)oxy-3-(trifluoromethyl)phenyl)amino)-2,3-dihydro-4H-[1,4]oxazino[2,3-f]quinazolin-4-yl)but-2-en-1-one | 582 | (400 MHz, DMSO-d₆) δ 9.87 (s, 1H), 8.44 (s, 1H), 8.08 (d, J = 2.6 Hz, 1H), 7.99-7.93 (m, 1H), 7.84 (s, 1H), 7.54-7.45 (m, 1H), 7.37 (d, J = 9.1 Hz, 1H), 7.34-7.24 (m, 3H), 7.22-7.15 (m, 1H), 6.86-6.78 (m, 1H), 6.58 (d, J = 15.2 Hz, 1H), 5.34 (s, 2H), 4.69-4.62 (m, 2H), 4.09-4.02 (m, 2H), 3.13-3.04 (m, 2H), 2.18 (s, 6H). |
| 68 | VIII-27 | (4-((3-fluorobenzyl)oxy)-3-methoxyphenyl)amino structure | (E)-4-(dimethylamino)-1-(10-((4-((3-fluorobenzyl)oxy)-3-methoxyphenyl)amino)-2,3-dihydro-4H-[1,4]oxazino[2,3-f]quinazolin-4-yl)but-2-en-1-one | 544 | (400 MHz, DMSO-d₆) δ 9.76 (s, 1H), 8.43 (s, 1H), 7.81 (s, 1H), 7.50-7.40 (m, 2H), 7.35-7.25 (m, 4H), 7.21-7.11 (m, 1H), 7.04 (d, J = 8.8 Hz, 1H), 6.87-6.77 (m, 1H), 6.58 (d, J = 15.3 Hz, 1H), 5.14 (s, 2H), 4.67 (t, J = 4.5 Hz, 2H), 4.09-4.02 (m, 2H), 3.83 (s, 3H), 3.15-3.03 (m, 2H), 2.18 (s, 6H). |

-continued

| Example No. | Starting Intermediate No. | R¹X | Example compounds | | |
|---|---|---|---|---|---|
| | | | Name | LCMS m/z = (M + H)⁺ | HNMR |
| 69 | VIII-28 | (structure: 3-fluoro-4-((3-fluorobenzyl)oxy)aniline fragment) | (E)-4-(dimethylamino)-1-(10-((4-((3-fluorobenzyl)oxy)-3-fluorophenyl)amino)-2,3-dihydro-4H-[1,4]oxazino[2,3-f]quinazolin-4-yl)but-2-en-1-one | 532 | (400 MHz, DMSO-d₆) δ 9.83 (s, 1H), 8.48 (s, 1H), 7.96-7.77 (m, 2H), 7.54-7.40 (m, 2H), 7.37-7.15 (m, 5H), 6.89-6.77 (m, 1H), 6.58 (d, J = 15.4 Hz, 1H), 5.23 (s, 2H), 4.73-4.61 (m, 2H), 4.10-4.00 (m, 2H), 3.14-3.00 (m, 2H), 2.17 (s, 6H). |
| 70 | VIII-29 | (structure: 4-((4-fluorophenyl)thio)aniline fragment) | (E)-4-(dimethylamino)-1-(10-((4-((4-fluorophenyl)thio)phenyl)amino)-2,3-dihydro-4H-[1,4]oxazino[2,3-f]quinazolin-4-yl)but-2-en-1-one | 516 | (400 MHz, DMSO-d₆) δ 9.97 (s, 1H), 8.51 (s, 1H), 7.96-7.82 (m, 3H), 7.43-7.32 (m, 5H), 7.27-7.20 (m, 2H), 6.86-6.78 (m, 1H), 6.58 (d, J = 15.2 Hz, 1H), 4.71-4.64 (m, 2H), 4.09-4.04 (m, 2H), 3.12-3.06 (m, 2H), 2.18 (s, 6H). |
| 71 | VIII-30 | (structure: 4-(2-fluoro-5-methylphenoxy)aniline fragment) | (E)-4-(dimethylamino)-1-(10-((4-(2-fluoro-5-methylphenoxy)phenyl)amino)-2,3-dihydro-4H-[1,4]oxazino[2,3-f]quinazolin-4-yl)but-2-en-1-one | 514 | (400 MHz, DMSO-d₆) δ 9.96-9.72 (m, 1H), 8.43 (s, 1H), 7.98-7.63 (m, 3H), 7.37-7.15 (m, 2H), 7.10-6.92 (m, 4H), 6.88-6.70 (m, 1H), 6.67-6.47 (m, 1H), 4.83-4.47 (m, 2H), 4.14-3.87 (m, 2H), 3.15-2.94 (m, 2H), 2.35-2.24 (m, 3H), 2.22-2.00 (s, 6H). |
| 72 | VIII-31 | (structure: 4-(5-chloro-2-fluorophenoxy)aniline fragment) | (E)-4-(dimethylamino)-1-(10-((4-(5-chloro-2-fluorophenoxy)phenyl)amino)-2,3-dihydro-4H-[1,4]oxazino[2,3-f]quinazolin-4-yl)but-2-en-1-one | 534 | (400 MHz, DMSO-d₆) δ 9.88 (s, 1H), 8.45 (s, 1H), 7.96-7.67 (m, 3H), 7.47 (dd, J = 10.8, 8.8 Hz, 1H), 7.33-7.24 (m, 2H), 7.22-7.05 (m, 3H), 6.87-6.73 (m, 1H), 6.58 (d, J = 15.2 Hz, 1H), 4.66 (t, J = 4.6 Hz, 2H), 4.05 (t, J = 4.9 Hz, 2H), 3.07 (d, J = 5.8 Hz, 2H), 2.17 (s, 6H). |

-continued

| Example No. | Starting Intermediate No. | R¹X | Example compounds Name | LCMS m/z = (M + H)⁺ | HNMR |
|---|---|---|---|---|---|
| 73 | VIII-32 | (structure: 2,5-difluorophenoxy-phenyl-NH-) | (E)-4-(dimethylamino)-1-(10-((4-(2,5-difluorophenoxy)phenyl)amino)-2,3-dihydro-4H-[1,4]oxazino[2,3-f]quinazolin-4-yl)but-2-en-1-one | 518 | (400 MHz, DMSO-d₆) δ 9.83 (s, 1H), 8.43 (s, 1H), 8.02-7.61 (m, 3H), 7.57-7.41 (m, 1H), 7.38-7.21 (m, 2H), 7.18-7.08 (m, 1H), 7.02 (d, J = 8.6 Hz, 2H), 6.87-6.72 (m, 1H), 6.57 (d, J = 15.4 Hz, 1H), 4.65 (t, J = 4.6 Hz, 2H), 4.04 (t, J = 4.7 Hz, 2H), 3.07 (d, J = 5.8 Hz, 2H), 2.17 (s, 6H). |
| 74 | VIII-33 | (structure: 1-(3-fluorophenyl)ethoxy-phenyl-NH-) | (E)-4-(dimethylamino)-1-(10-((4-(1-(3-fluorophenyl)ethoxy)phenyl)amino)-2,3-dihydro-4H-[1,4]oxazino[2,3-f]quinazolin-4-yl)but-2-en-1-one | 528 | (400 MHz, DMSO-d₆) δ 9.70 (s, 1H), 8.37 (s, 1H), 7.77 (s, 1H), 7.55 (d, J = 8.6 Hz, 2H), 7.47-7.34 (m, 1H), 7.30-7.14 (m, 3H), 7.14-7.00 (m, 1H), 6.94 (d, J = 8.6 Hz, 2H), 6.85-6.71 (m, 1H), 6.56 (d, J = 15.4 Hz, 1H), 5.61-5.39 (m, 1H), 4.62 (t, J = 4.7 Hz, 2H), 4.02 (t, J = 4.7 Hz, 2H), 3.07 (d, J = 5.8 Hz, 2H), 2.16 (s, 6H), 1.56 (d, J = 6.3 Hz, 3H). |
| 75 | VIII-34 | (structure: 1-(pyridin-2-yl)ethoxy-phenyl-NH-) | (E)-4-(dimethylamino)-1-(10-((4-(1-(pyridin-2-yl)ethoxy)phenyl)amino)-2,3-dihydro-4H-[1,4]oxazino[2,3-f]quinazolin-4-yl)but-2-en-1-one | 511 | (400 MHz, DMSO-d₆) δ 9.73 (d, J = 19.8 Hz, 1H), 8.66-8.51 (m, 1H), 8.44-8.29 (m, 1H), 7.88-7.74 (m, 2H), 7.63-7.51 (m, 2H), 7.45 (d, J = 7.4 Hz, 1H), 7.40-7.22 (m, 2H), 7.01-6.88 (m, 2H), 6.88-6.70 (m, 1H), 6.55 (d, J = 18.1 Hz, 1H), 5.62-5.35 (m, 1H), 4.73-4.54 (m, 2H), 4.11-3.92 (m, 2H), 3.41-3.33 (m, 3H), 3.06 (d, J = 5.8 Hz, 2H), 2.16 (s, 6H). |

-continued

| Example No. | Starting Intermediate No. | R¹X | Example compounds Name | LCMS m/z = (M + H)⁺ | HNMR |
|---|---|---|---|---|---|
| 76 | VIII-35 | (4-(pyridin-3-ylmethoxy)phenyl)amino structure | (E)-4-(dimethylamino)-1-(10-((4-(pyridin-3-ylmethoxy)phenyl)amino)-2,3-dihydro-4H-[1,4]oxazino[2,3-f]quinazolin-4-yl)but-2-en-1-one | 497 | (400 MHz, DMSO-$d_6$) δ 9.76 (s, 1H), 8.69 (d, J = 2.5 Hz, 1H), 8.59-8.51 (m, 1H), 8.40 (s, 1H), 7.93-7.86 (m, 1H), 7.84-7.70 (m, 1H), 7.70-7.60 (m, 2H), 7.47-7.38 (m, 1H), 7.32-7.22 (m, 1H), 7.10-7.00 (m, 2H), 6.84-6.74 (m, 1H), 6.57 (d, J = 15.2 Hz, 1H), 5.18 (s, 2H), 4.90-4.42 (m, 2H), 4.04 (t, J = 4.7 Hz, 2H), 3.09 (d, J = 5.8 Hz, 2H), 2.23-2.02 (s, 6H). |
| 77 | VIII-36 | (4-(pyridin-4-ylmethoxy)phenyl)amino structure | (E)-4-(dimethylamino)-1-(10-((4-(pyridin-4-ylmethoxy)phenyl)amino)-2,3-dihydro-4H-[1,4]oxazino[2,3-f]quinazolin-4-yl)but-2-en-1-one | 497 | (400 MHz, DMSO-$d_6$) δ 9.76 (s, 1H), 8.59 (d, J = 5.1 Hz, 2H), 8.40 (s, 1H), 7.80 (s, 1H), 7.67 (d, J = 8.6 Hz, 2H), 7.46 (d, J = 5.0 Hz, 2H), 7.27 (d, J = 9.0 Hz, 1H), 7.06 (d, J = 8.6 Hz, 2H), 6.90-6.73 (m, 1H), 6.57 (d, J = 15.3 Hz, 1H), 5.22 (s, 2H), 4.65 (t, J = 4.6 Hz, 2H), 4.04 (t, J = 4.6 Hz, 2H), 3.08 (d, J = 6.1 Hz, 2H), 2.17 (s, 6H). |
| 78 | VIII-41 | (4-(benzyloxy)phenyl)amino structure | (E)-1-(10-((4-(benzyloxy)phenyl)amino)-2,3-dihydro-4H-[1,4]oxazino[2,3-f]quinazolin-4-yl)-4-(dimethylamino)but-2-en-1-one | 496 | (400 MHz, DMSO-$d_6$) δ 9.75 (s, 1H), 8.40 (s, 1H), 7.80 (s, 1H), 7.67-7.63 (m, 2H), 7.49-7.45 (m, 2H), 7.43-7.38 (m, 2H), 7.36-7.33 (m, 1H), 7.27 (d, J = 9.2 Hz, 1H), 7.07-7.03 (m, 2H), 6.84-6.77 (m, 1H), 6.62-6.53 (m, 1H), 5.13 (s, 2H), 4.65 (t, J = 4.4 Hz, 2H), 4.04 (t, J = 4.4 Hz, 2H), 3.09 (d, J = 5.6 Hz, 2H), 2.18 (s, 6H). |

-continued

| Example No. | Starting Intermediate No. | R¹X | Example compounds Name | LCMS m/z = (M + H)⁺ | HNMR |
|---|---|---|---|---|---|
| 79 | VIII-42 | 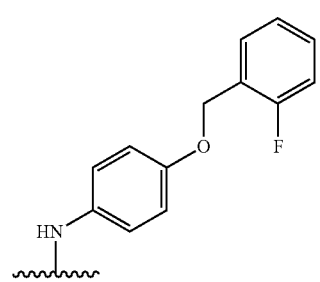 [SMILES: *Nc1ccc(OCc2ccccc2F)cc1] | (E)-4-(dimethylamino)-1-(10-((4-((2-fluorobenzyl)oxy)phenyl)amino)-2,3-dihydro-4H-[1,4]oxazino[2,3-f]quinazolin-4-yl)but-2-en-1-one | 514 | (400 MHz, DMSO-d₆) δ 9.77 (s, 1H), 8.40 (s, 1H), 7.80 (s, 1H), 7.69-7.65 (m, 2H), 7.60-7.56 (m, 1H), 7.46-7.40 (m, 1H), 7.29-7.26 (m, 2H), 7.25-7.23 (m, 1H), 7.08-7.05 (m, 2H), 6.85-6.77 (m, 1H), 6.60-6.53 (m, 1H), 5.17 (s, 2H), 4.65 (t, J = 4.4 Hz, 2H), 4.04 (t, J = 4.4 Hz, 2H), 3.07 (dd, J = 6.0, 1.6 Hz, 2H), 2.17 (s, 6H). |
| 80 | VIII-43 | 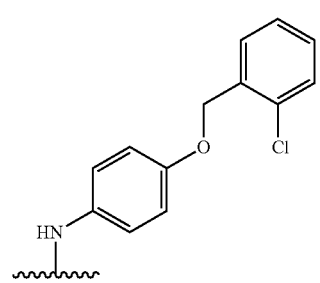 [SMILES: *Nc1ccc(OCc2ccccc2Cl)cc1] | (E)-4-(dimethylamino)-1-(10-((4-((2-chlorobenzyl)oxy)phenyl)amino)-2,3-dihydro-4H-[1,4]oxazino[2,3-f]quinazolin-4-yl)but-2-en-1-one | 530 | (400 MHz, DMSO-d₆) δ 9.77 (s, 1H), 8.40 (s, 1H), 7.80 (s, 1H), 7.68-7.66 (m, 2H), 7.64-7.60 (m, 1H), 7.54-7.51 (m, 1H), 7.42-7.39 (m, 2H), 7.28 (d, J = 9.0 Hz, 1H), 7.08-7.05 (m, 2H), 6.85-6.77 (m, 1H), 6.57 (d, J = 15.2 Hz, 1H), 5.19 (s, 2H), 4.65 (t, J = 4.6 Hz, 2H), 4.04 (t, J = 4.6 Hz, 2H), 3.07 (dd, J = 6.0, 1.6 Hz, 2H), 2.17 (s, 6H). |
| 81 | VIII-44 | 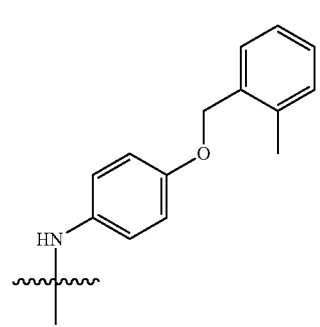 [SMILES: *Nc1ccc(OCc2ccccc2C)cc1] | (E)-4-(dimethylamino)-1-(10-((4-((2-methylbenzyl)oxy)phenyl)amino)-2,3-dihydro-4H-[1,4]oxazino[2,3-f]quinazolin-4-yl)but-2-en-1-one | 510 | (400 MHz, DMSO-d₆) δ 9.76 (s, 1H), 8.40 (s, 1H), 7.79 (s, 1H), 7.67-7.63 (m, 2H), 7.43 (d, J = 7.2 Hz, 1H), 7.29-7.21 (m, 4H), 7.09-7.05 (m, 2H), 6.84-6.77 (m, 1H), 6.57 (d, J = 15.2 Hz, 1H), 5.11 (s, 2H), 4.65 (t, J = 4.4 Hz, 2H), 4.04 (t, J = 4.4 Hz, 2H), 3.07 (dd, J = 6.0, 1.6 Hz, 2H), 2.35 (s, 3H), 2.17 (s, 6H). |

-continued

| Example No. | Starting Intermediate No. | R¹X | Name | LCMS m/z = (M + H)⁺ | HNMR |
|---|---|---|---|---|---|
| 82 | VIII-45 | | (E)-4-(dimethylamino)-1-(10-((4-((2-methoxybenzyl)oxy)phenyl)amino)-2,3-dihydro-4H-[1,4]oxazino[2,3-f]quinazolin-4-yl)but-2-en-1-one | 526 | (400 MHz, DMSO-d₆) δ 9.76 (s, 1H), 8.40 (s, 1H), 7.80 (s, 1H), 7.66-7.63 (m, 2H), 7.41 (dd, J = 7.2, 1.6 Hz, 1H), 7.37-7.32 (m, 1H), 7.27 (d, J = 9.0 Hz, 1H), 7.08-7.05 (m, 1H), 7.04-7.01 (m, 2H), 7.00-6.95 (m, 1H), 6.85-6.77 (m, 1H), 6.57 (d, J = 15.2 Hz, 1H), 5.08 (s, 2H), 4.65 (t, J = 4.6 Hz, 2H), 4.04 (t, J = 4.6 Hz, 2H), 3.84 (s, 3H), 3.07 (dd, J = 6.0, 1.6 Hz, 2H), 2.17 (s, 6H). |
| 83 | VIII-46 | | (E)-1-(10-((4-((3-chlorobenzyl)oxy)phenyl)amino)-2,3-dihydro-4H-[1,4]oxazino[2,3-f]quinazolin-4-yl)-4-(dimethylamino)but-2-en-1-one | 530 | (400 MHz, DMSO-d₆) δ 9.76 (s, 1H), 8.40 (s, 1H), 7.79 (s, 1H), 7.66 (d, J = 9.0 Hz, 2H), 7.57-7.48 (m, 1H), 7.48-7.34 (m, 3H), 7.27 (d, J = 9.0 Hz, 1H), 7.07-6.99 (m, 2H), 6.88-6.70 (m, 1H), 6.57 (d, J = 15.2 Hz, 1H), 5.16 (s, 2H), 4.65 (t, J = 4.7 Hz, 2H), 4.04 (t, J = 4.6 Hz, 2H), 3.14-2.97 (m, 2H), 2.17 (s, 6H). |
| 84 | VIII-47 | | (E)-4-(dimethylamino)-1-(10-((4-((3-methylbenzyl)oxy)phenyl)amino)-2,3-dihydro-4H-[1,4]oxazino[2,3-f]quinazolin-4-yl)but-2-en-1-one | 510 | (400 MHz, DMSO-d₆) δ 9.75 (s, 1H), 8.40 (s, 1H), 7.80 (s, 1H), 7.66-7.63 (m, 2H), 7.29-7.25 (m, 4H), 7.16-7.13 (m, 1H), 7.05-7.02 (m, 2H), 6.84-6.77 (m, 1H), 6.57 (d, J = 15.2 Hz, 1H), 5.09 (s, 2H), 4.65 (t, J = 4.4 Hz, 2H), 4.04 (t, J = 4.4 Hz, 2H), 3.07 (dd, J = 6.0, 1.6 Hz, 2H), 2.33 (s, 3H), 2.17 (s, 6H). |

-continued

| Example No. | Starting Intermediate No. | R¹X | Example compounds Name | LCMS m/z = (M + H)⁺ | HNMR |
|---|---|---|---|---|---|
| 85 | VIII-48 | (structure: 4-[(3-cyanobenzyl)oxy]phenyl-NH-) | (E)-4-(dimethylamino)-1-(10-((4-((3-cyanobenzyl)oxy)phenyl)amino)-2,3-dihydro-4H-[1,4]oxazino[2,3-f]quinazolin-4-yl)but-2-en-1-one | 521 | (400 MHz, DMSO-d₆) δ 9.76 (s, 1H), 8.40 (s, 1H), 7.94-7.92 (m, 1H), 7.86-7.78 (m, 3H), 7.68-7.65 (m, 2H), 7.65-7.61 (m, 1H), 7.28 (d, J = 9.0 Hz, 1H), 7.08-7.05 (m, 2H), 6.85-6.78 (m, 1H), 6.57 (d, J = 15.2 Hz, 1H), 5.20 (s, 2H), 4.65 (t, J = 4.6 Hz, 2H), 4.04 (t, J = 4.6 Hz, 2H), 3.07 (dd, J = 6.0, 1.6 Hz, 2H), 2.17 (s, 6H). |
| 86 | VIII-49 | (structure: 4-[(3-methoxybenzyl)oxy]phenyl-NH-) | (E)-4-(dimethylamino)-1-(10-((4-((3-methoxybenzyl)oxy)phenyl)amino)-2,3-dihydro-4H-[1,4]oxazino[2,3-f]quinazolin-4-yl)but-2-en-1-one | 526 | (400 MHz, DMSO-d₆) δ 9.75 (s, 1H), 8.40 (s, 1H), 7.79 (s, 1H), 7.67-7.57 (m, 2H), 7.38-7.19 (m, 2H), 7.10-6.95 (m, 4H), 6.94-6.74 (m, 2H), 6.57 (d, J = 15.3 Hz, 1H), 5.11 (s, 2H), 4.68-4.57 (m, 2H), 4.04 (t, J = 4.7 Hz, 2H), 3.77 (s, 3H), 3.10-2.99 (m, 2H), 2.17 (s, 6H). |
| 87 | VIII-50 | (structure: 4-[(4-chlorobenzyl)oxy]phenyl-NH-) | (E)-4-(dimethylamino)-1-(10-((4-((4-chlorobenzyl)oxy)phenyl)amino)-2,3-dihydro-4H-[1,4]oxazino[2,3-f]quinazolin-4-yl)but-2-en-1-one | 530 | (400 MHz, DMSO-d₆) δ 9.76 (s, 1H), 8.40 (s, 1H), 7.80 (s, 1H), 7.67-7.64 (m, 2H), 7.51-7.49 (m, 2H), 7.47-7.45 (m, 2H), 7.27 (d, J = 9.0 Hz, 1H), 7.06-7.02 (m, 2H), 6.84-6.77 (m, 1H), 6.57 (d, J = 15.2 Hz, 1H), 5.14 (s, 2H), 4.65 (t, J = 4.6 Hz, 2H), 4.04 (t, J = 4.6 Hz, 2H), 3.07 (dd, J = 6.0, 1.6 Hz, 2H), 2.17 (s, 6H). |
| 88 | VIII-51 | (structure: 4-[(4-methylbenzyl)oxy]phenyl-NH-) | (E)-4-(dimethylamino)-1-(10-((4-((4-methylbenzyl)oxy)phenyl)amino)-2,3-dihydro-4H-[1,4]oxazino[2,3-f]quinazolin-4-yl)but-2-en-1-one | 510 | (400 MHz, DMSO-d₆) δ 9.75 (s, 1H), 8.39 (s, 1H), 7.79 (s, 1H), 7.65-7.62 (m, 2H), 7.35 (d, J = 7.6 Hz, 2H), 7.27 (d, J = 9.2 Hz, 1H), 7.20 (d, J = 7.6 Hz, 2H), 7.04-7.01 (m, 2H), 6.84-6.77 (m, 1H), 6.57 (d, J = 15.2 Hz, 1H), 5.08 (s, 2H), 4.65 (t, J = 4.4 Hz, 2H), 4.04 (t, J = |

| Example No. | Starting Intermediate No. | R¹X | Example compounds Name | LCMS m/z = (M + H)⁺ | HNMR |
|---|---|---|---|---|---|
| | | | | | 4.4 Hz, 2H), 3.07 (dd, J = 6.0, 1.6 Hz, 2H), 2.31 (s, 3H), 2.17 (s, 6H). |
| 89 | VIII-52 | ![structure] | (E)-1-(10-((4-((2,5-difluorobenzyl)oxy)phenyl)amino)-2,3-dihydro-4H-[1,4]oxazino[2,3-f]quinazolin-4-yl)-4-(dimethylamino)but-2-en-1-one | 532 | (400 MHz, DMSO-d₆) δ 9.78 (s, 1H), 8.41 (s, 1H), 7.80 (s, 1H), 7.72-7.64 (m, 2H), 7.47-7.37 (m, 1H), 7.38-7.20 (m, 3H), 7.12-7.02 (m, 2H), 6.88-6.75 (m, 1H), 6.57 (d, J = 15.3 Hz, 1H), 5.16 (s, 2H), 4.65 (t, J = 4.7 Hz, 2H), 4.04 (t, J = 4.7 Hz, 2H), 3.13-3.02 (m, 2H), 2.17 (s, 6H). |
| 90 | VIII-53 | ![structure] | (E)-1-(10-((4-((2-chloro-5-fluorobenzyl)oxy)phenyl)amino)-2,3-dihydro-4H-[1,4]oxazino[2,3-f]quinazolin-4-yl)-4-(dimethylamino)but-2-en-1-one | 548 | (400 MHz, DMSO-d₆) δ 9.78 (s, 1H), 8.41 (s, 1H), 7.80 (s, 1H), 7.73-7.62 (m, 2H), 7.63-7.53 (m, 1H), 7.53-7.41 (m, 1H), 7.36-7.17 (m, 2H), 7.14-7.02 (m, 2H), 6.88-6.73 (m, 1H), 6.57 (d, J = 15.3 Hz, 1H), 5.18 (s, 2H), 4.65 (t, J = 4.7 Hz, 2H), 4.04 (t, J = 4.7 Hz, 2H), 3.13-3.00 (m, 2H), 2.18 (s, 6H). |

Example 91: Preparation of (E)-1-(10-((4-phenoxyphenyl)amino)-2,3-dihydro-4H-[1,4]oxazino[2,3-f]quinazolin-4-yl)-4-(pyrrolidin-1-yl)but-2-en-1-one

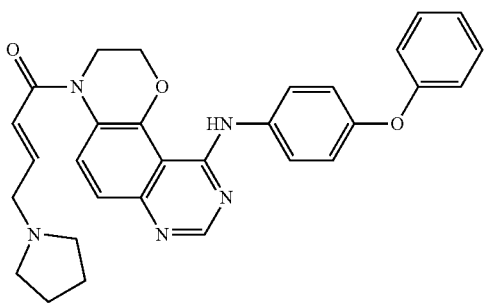 [SMILES: O=C(/C=C/CN1CCCC1)N1CCOc2c1ccc1ncnc(Nc3ccc(Oc4ccccc4)cc3)c21]

N-(4-phenoxyphenyl)-3,4-dihydro-2H-[1,4]oxazino[2,3-f]quinazolin-10-amine (VIII-1) (185 mg, 0.5 mmol) was dissolved in a mixed solvent of dichloromethane and dimethylformamide, to which 4-bromocrotonyl chloride (91 mg, 0.5 mmol) was added, and stirred at room temperature until the reaction was completed. The reaction was quenched with water, extracted with ethyl acetate, the organic phase was concentrated and directly dissolved in acetonitrile, to which diisopropylethylamine (129 mg, 1 mmol) and pyrrolidine (67 mg, 1 mmol) were added, and stirred at room temperature until the reaction was completed. The reaction was quenched by adding water, extracted with ethyl acetate, and the organic phase was concentrated and purified by silica gel column chromatography to afford 63 mg of a off-white solid with a yield of 25%. ¹H NMR (400 MHz, DMSO-d₆) δ 9.87 (s, 1H), 8.46 (s, 1H), 7.84-7.78 (m, 3H), 7.44-7.37 (m, 2H), 7.32-7.28 (m, 1H), 7.16-7.11 (m, 1H), 7.10-7.06 (m, 2H), 7.05-7.00 (m, 2H), 6.90-6.82 (m, 1H), 6.62-6.55 (m, 1H), 4.67 (t, J=4.4 Hz, 2H), 4.05 (t, J=4.4 Hz, 2H), 3.27-3.23 (m, 2H), 2.49-2.45 (m, 4H), 1.72-1.67 (m, 4H); MS: 508[M+H]⁺.

Examples 92-111

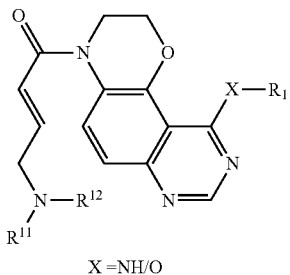

X =NH/O

With reference to the preparation method of Example 91, wherein exactly the same operations were used, and N-(4-phenoxyphenyl)-3,4-dihydro-2H-[1,4]oxazino[2,3-f]quinazolin-10-amine (VIII-1) was replaced with the same molar equivalent of intermediate represented by formula (VIII) wherein $R^1X$ is the substituent in the table below and pyrrolidine was replaced with equivalent molar equivalent of

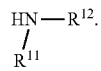

The specific example compounds are shown in the table below:

| Example No. | Starting Intermediate No. | $R^1X$ | $\begin{array}{c}\text{\textasciitilde}\\N-R^{12}\\/\\R^{11}\end{array}$ | Example compound Name | LCMS m/z = (M + H)+ | HNMR |
|---|---|---|---|---|---|---|
| 92 | VIII-1 | HN-C6H4-O-C6H5 | N(Et)2 | (E)-4-(diethylamino)-1-(10-((4-phenoxyphenyl)amino)-2,3-dihydro-4H-[1,4]oxazino[2,3-f]quinazolin-4-yl)but-2-en-1-one | 510 | (400 M, CDCl3) δ 9.55 (s, 1H), 8.62 (s, 1H), 7.70-7.68 (m, 2H), 7.61 (brs, 1H), 7.47-7.45 (m, 1H), 7.38-7.35 (m, 2H), 7.15-7.05 (m, 6H), 6.72-6.64 (m, 1H), 4.70 (s, 2H), 4.22 (s, 2H), 3.64 (br, 2H), 3.02-2.98 (m, 2H), 1.66 (br, 2H), 1.31-1.27 (m, 6H) |
| 93 | VIII-1 | HN-C6H4-O-C6H5 | piperidinyl | (E)-1-(10-((4-phenoxyphenyl)amino)-2,3-dihydro-4H-[1,4]oxazino[2,3-f]quinazolin-4-yl)-4-(piperidin-1-yl)but-2-en-1-one | 522 | (400 M, DMSO-d6) δ 9.87 (s, 1H), 8.45 (s, 1H), 7.81-7.79 (m, 3H), 7.42-7.38 (m, 2H), 7.30-7.28 (m, 1H), 7.15-7.01 (m, 5H), 6.84-6.80 (m, 1H), 6.60-6.56 (m, 1H), 4.69-4.63 (m, 2H), 4.09-4.03 (m, 2H), 3.14-3.08 (m, 2H), 2.39-2.33 (m, 4H), 1.49-1.47 (m, 4H), 1.42-1.36 (m, 2H) |
| 94 | VIII-1 | HN-C6H4-O-C6H5 | morpholino | (E)-4-morpholino-1-(10-((4-phenoxyphenyl)amino)-2,3-dihydro-4H-[1,4]oxazino[2,3-f]quinazolin-4-yl)but-2-en-1-one | 524 | (300 MHz, DMSO-d6) δ 9.87 (s, 1H), 8.45 (s, 1H), 7.88-7.73 (m, 3H), 7.44-7.36 (m, 2H), 7.30 (d, J = 9.0 Hz, 1H), 7.16-7.00 (m, 5H), 6.79 (s, 1H), 6.68-6.53 (m, 1H), 4.71-4.58 (m, 2H), 4.09-4.03 (m, 2H), 3.57 (t, J = 4.6 Hz, 4H), 3.14 (d, J = 5.5 Hz, 2H), 2.43-2.34 (m, 4H). |

-continued

| Example No. | Starting Intermediate No. | R¹X | N-R¹²<br>R¹¹ | Example compound Name | LCMS m/z = (M + H)⁺ | HNMR |
|---|---|---|---|---|---|---|
| 95 | VIII-1 | 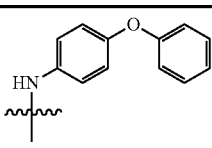 | 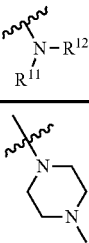 | (E)-4-(4-methylpiperazin-1-yl)-1-(10-((4-phenoxyphenyl)amino)-2,3-dihydro-4H-[1,4]oxazino[2,3-f]quinazolin-4-yl)but-2-en-1-one | 537 | (400 MHz, DMSO-d₆) δ 9.87 (s, 1H), 8.46 (s, 1H), 7.86-7.72 (m, 3H), 7.42-7.38 (m, 2H), 7.30 (d, J = 8.9 Hz, 1H), 7.13 (t, J = 7.4 Hz, 1H), 7.10-7.06 (m, 2H), 7.05-7.00 (m, 2H), 6.85-6.76 (m, 1H), 6.59 (d, J = 15.2 Hz, 1H), 4.67 (t, J = 4.6 Hz, 2H), 4.05 (t, J = 4.6 Hz, 2H), 3.14 (d, J = 5.7 Hz, 2H), 2.49-2.22 (m, 8H), 2.17 (s, 3H). |
| 96 | VIII-4 | 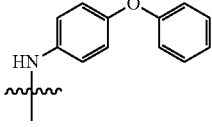 | 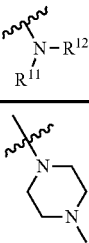 | (E)-1-(10-((3-chloro-4-((3-fluorobenzyl)oxy)phenyl)amino)-2,3-dihydro-4H-[1,4]oxazino[2,3-f]quinazolin-4-yl)-4-morpholinobut-2-en-1-one | 590 | (400 MHz, DMSO-d₆) δ 9.82 (s, 1H), 8.47 (s, 1H), 8.00 (d, J = 2.4 Hz, 1H), 7.90-7.74 (m, 1H), 7.70-7.65 (m, 1H), 7.52-7.44 (m, 1H), 7.35-7.24 (m, 4H), 7.22-7.15 (m, 1H), 6.85-6.77 (m, 1H), 6.66-6.56 (m, 1H), 5.27 (s, 2H), 4.66 (t, J = 4.4 Hz, 2H), 4.04 (t, J = 4.4 Hz, 2H), 3.61-3.55 (m, 4H), 3.17-3.11 (m, 2H), 2.44-2.36 (m, 4H) |
| 97 | VIII-6 | 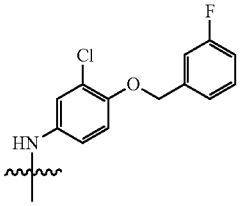 [SMILES: *Nc1ccc(OCc2cccc(F)c2)c(Cl)c1] | 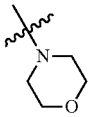 | (E)-1-(10-((2-fluoro-4-phenoxyphenyl)amino)-2,3-dihydro-4H-[1,4]oxazino[2,3-f]quinazolin-4-yl)-4-(piperidin-1-yl)but-2-en-1-one | 540 | (400 MHz, Methanol-d₄) δ 8.77-8.65 (m, 1H), 8.48-8.41 (m, 1H), 7.69-7.47 (m, 1H), 7.38-7.29 (m, 2H), 7.28-7.13 (m, 2H), 7.06-6.95 (m, 2H), 6.94-6.86 (m, 1H), 6.86-6.71 (m, 2H), 6.68-6.61 (m, 1H), 5.39 (s, 2H), 4.38-4.25 (m, 2H), 3.76-3.67 (m, 2H), 3.08-2.91 (m, 4H), 1.64-1.45 (m, 6H). |
| 98 | VIII-7 | 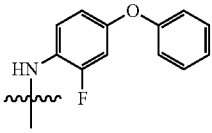 [SMILES: *Nc1ccc(Oc2ccccc2)cc1F] | 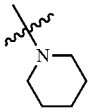 [SMILES: *N1CCCCC1] | (E)-1-(10-((3-fluoro-4-phenoxyphenyl)amino)-2,3-dihydro-4H-[1,4]oxazino[2,3-f]quinazolin-4-yl)-4-(piperidin-1- | 540 | (400 MHz, Methanol-d₄) δ 8.51 (s, 1H), 8.08-7.99 (m, 1H), 7.93-7.79 (m, 1H), 7.51-7.45 (m, 1H), 7.40-7.30 (m, 3H), 7.17-6.97 (m, 4H), 6.94- |

| Example No. | Starting Intermediate No. | R¹X | N–R¹²  / R¹¹ | Example compound Name | LCMS m/z = (M + H)⁺ | HNMR |
|---|---|---|---|---|---|---|
| | | | | yl)but-2-en-1-one | | 6.87 (m, 1H), 6.66 (d, J = 15.2 4.65 (m, 2H), 4.21-4.13 (m, 2H), 3.25-3.19 (m, 2H), 2.58-2.42 (m, 4H), 1.68-1.60 (m, 4H), 1.55-1.47 (m, 2H). |
| 99 | VIII-8 |  | 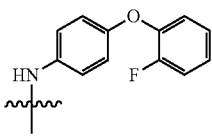 [SMILES: *Nc1ccc(Oc2ccccc2F)cc1] | (E)-1-(10-((4-(2-fluorophenoxy)phenyl)amino)-2,3-dihydro-4H-[1,4]oxazino[2,3-f]quinazolin-4-yl)-4-((4-methoxybutyl)amino)but-2-en-1-one | 558 | (400 MHz, Methanol-d₄) δ 8.45-8.40 (m, 1H), 7.77-7.69 (m, 3H), 7.40-7.34 (m, 2H), 7.30-7.26 (m, 1H), 7.23-7.19 (m, 2H), 7.07-7.02 (m, 2H), 7.02-6.94 (m, 1H), 6.82-6.74 (m, 1H), 4.84-4.69 (m, 2H), 4.19-4.14 (m, 2H), 3.70 (s, 3H), 3.19-3.12 (m, 2H), 2.94-2.83 (m, 2H), 2.32-2.14 (m, 2H), 1.69-1.66 (m, 4H). |
| 100 | VIII-5 |  | 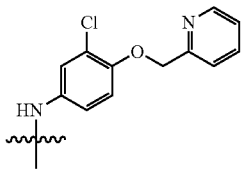 [SMILES: *Nc1ccc(OCc2ccccn2)c(Cl)c1] | (E)-1-(10-((3-chloro-4-(pyridin-2-ylmethoxy)phenyl)amino)-2,3-dihydro-4H-[1,4]oxazino[2,3-f]quinazolin-4-yl)-4-(cyclopropyl(methyl)amino)but-2-en-1-one | 557 | (400 MHz, DMSO-d₆) δ 9.82 (s, 1H), 8.64-8.55 (m, 1H), 8.46 (s, 1H), 8.01 (d, J = 2.6 Hz, 1H), 7.95-7.73 (m, 2H), 7.70-7.62 (m, 1H), 7.58 (d, J = 7.8 Hz, 1H), 7.42-7.34 (m, 1H), 7.32-7.16 (m, 2H), 6.89-6.78 (m, 1H), 6.55 (d, J = 15.2 Hz, 1H), 5.31 (s, 2H), 4.65 (t, J = 4.6 Hz, 2H), 4.04 (t, J = 4.7 Hz, 2H), 3.32-3.29 (m, 2H), 2.27 (s, 3H), 1.78-1.72 (m, 1H), 0.49-0.23 (m, 4H). |
| 101 | VIII-5 |  | 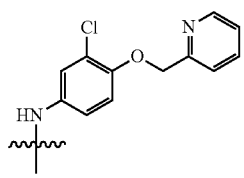 [SMILES: *Nc1ccc(OCc2ccccn2)c(Cl)c1] | (E)-1-(10-((3-chloro-4-(pyridin-2-ylmethoxy)phenyl)amino)-2,3-dihydro-4H-[1,4]oxazino[2,3-f]quinazolin-4-yl)-4-(cyclopropylamino)but-2-en-1-one | 543 | (400 MHz, DMSO-d₆) δ 9.82 (s, 1H), 8.60 (d, J = 4.8 Hz, 1H), 8.46 (s, 1H), 8.01 (d, J = 2.6 Hz, 1H), 7.90-7.87 (m, 1H), 7.66 (d, J = 6.2 Hz, 1H), 7.58 (d, J = 7.8 Hz, 1H), 7.50-7.48 (m, 1H), 7.39-7.36 (m, 1H), 7.31-7.28 (m, 1H), 7.27-7.25 (m, 1H), 7.08 (d, J = 7.8 Hz, 1H), 6.57 (d, J = 14.8 Hz, |

US 11,548,900 B2

-continued

| Example No. | Starting Intermediate No. | R¹X | N-R¹² / R¹¹ | Example compound Name | LCMS m/z = (M + H)⁺ | HNMR |
|---|---|---|---|---|---|---|
| | | | | | | 1H), 5.31 (s, 2H), 4.64 (t, J = 4.6 Hz, 2H), 4.05 (t, J = 4.1 Hz, 2H), 3.51-3.50 (m, 1H), 3.42-3.41 (m, 2H), 2.68-2.66 (m, 1H), 0.41-0.37 (m, 2H), 0.27-0.23 (m, 2H). |
| 102 | VIII-5 | 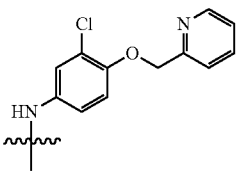 [SMILES: *Nc1ccc(OCc2ccccn2)c(Cl)c1] | 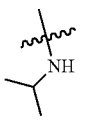 | (E)-1-(10-((3-chloro-4-(pyridin-2-ylmethoxy)phenyl)amino)-2,3-dihydro-4H-[1,4]oxazino[2,3-f]quinazolin-4-yl)-4-(isopropylamino)but-2-en-1-one | 545 | (400 MHz, DMSO-d₆) δ 9.83 (s, 1H), 8.60 (d, J = 4.8 Hz, 1H), 8.47 (s, 1H), 8.01 (d, J = 2.8 Hz, 1H), 7.92-7.80 (m, 2H), 7.67 (dd, J = 8.8, 2.8 Hz, 1H), 7.58 (d, J = 7.8 Hz, 1H), 7.39-7.35 (m, 1H), 7.33-7.25 (m, 2H), 6.89-6.80 (m, 1H), 6.80-6.68 (m, 1H), 5.31 (s, 2H), 4.67 (t, J = 4.6 Hz, 2H), 4.07 (t, J = 4.6 Hz, 2H), 3.68-3.62 (m, 2H), 3.31-3.31 (m, 1H), 2.68-2.66 (m, 1H), 1.14 (d, J = 6.4 Hz, 6H). |
| 103 | VIII-5 | 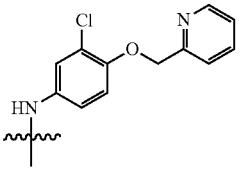 [SMILES: *Nc1ccc(OCc2ccccn2)c(Cl)c1] | 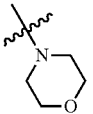 | (E)-1-(10-((3-chloro-4-(pyridin-2-ylmethoxy)phenyl)amino)-2,3-dihydro-4H-[1,4]oxazino[2,3-f]quinazolin-4-yl)-4-morpholinobut-2-en-1-one | 573 | (400 MHz, DMSO-d₆) δ 9.83 (s, 1H), 8.62-8.58 (m, 1H), 8.47 (s, 1H), 8.00 (d, J = 2.6 Hz, 1H), 7.93-7.78 (m, 2H), 7.68-7.63 (m, 1H), 7.61-7.56 (m, 1H), 7.41-7.35 (m, 1H), 7.33-7.24 (m, 2H), 6.86-6.77 (m, 1H), 6.72-6.60 (m, 1H), 5.31 (s, 2H), 4.66 (t, J = 4.6 Hz, 2H), 4.05 (t, J = 4.6 Hz, 2H), 3.70-3.60 (m, 4H), 3.18-3.12 (m, 2H), 2.66-2.51 (m, 4H). |
| 104 | VIII-5 | 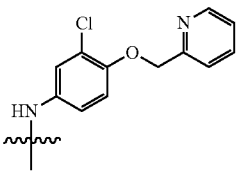 [SMILES: *Nc1ccc(OCc2ccccn2)c(Cl)c1] |  | (E)-1-(10-((3-chloro-4-(pyridin-2-ylmethoxy)phenyl)amino)-2,3-dihydro-4H-[1,4]oxazino[2,3-f]quinazolin-4-yl)-4-(4-methylpiperazin-1-yl)but-2-en-1-one | 586 | (400 MHz, DMSO-d₆) δ 9.82 (s, 1H), 8.64-8.56 (m, 1H), 8.46 (s, 1H), 8.01 (d, J = 2.6 Hz, 1H), 7.93-7.86 (m, 1H), 7.86-7.68 (m, 1H), 7.68-7.63 (m, 1H), 7.58 (d, J = 7.8 Hz, 1H), 7.43-7.33 (m, 1H), 7.33-7.23 (m, 2H), 6.87-6.75 (m, |

-continued

| Example No. | Starting Intermediate No. | R¹X | N-R¹² / R¹¹ | Name | LCMS m/z = (M + H)⁺ | HNMR |
|---|---|---|---|---|---|---|
| | | | | | | 1H), 6.70-6.52 (m, 1H), 5.31 (s, 2H), 4.66 (t, J = 4.5 Hz, 2H), 4.04 (t, J = 4.6 Hz, 2H), 3.14 (d, J = 5.7 Hz, 2H), 2.52-2.30 (m, 8H), 2.22 (s, 3H). |
| 105 | VIII-5 | 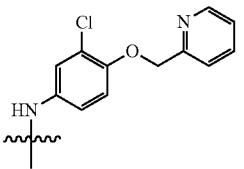 [SMILES: *Nc1ccc(OCc2ccccn2)c(Cl)c1] |  | (E)-1-(10-((3-chloro-4-(pyridin-2-ylmethoxy)phenyl)amino)-2,3-dihydro-4H-[1,4]oxazino[2,3-f]quinazolin-4-yl)-4-(diethylamino)but-2-en-1-one | 559 | (400 MHz, DMSO-d₆) δ 9.84 (s, 1H), 8.63-8.59 (m, 1H), 8.47 (s, 1H), 8.01 (d, J = 2.6 Hz, 1H), 7.93-7.86 (m, 1H), 7.79-7.61 (m, 2H), 7.58 (d, J = 7.8 Hz, 1H), 7.41-7.35 (m, 1H), 7.34-7.24 (m, 2H), 6.90-6.61 (m, 2H), 5.32 (s, 2H), 4.68 (t, J = 4.7 Hz, 2H), 4.06 (t, J = 4.7 Hz, 2H), 3.39-3.31 (m, 6H), 1.18-0.97 (m, 6H). |
| 106 | VIII-5 | 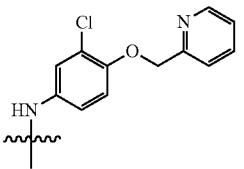 [SMILES: *Nc1ccc(OCc2ccccn2)c(Cl)c1] |  | (E)-1-(10-((3-chloro-4-(pyridin-2-ylmethoxy)phenyl)amino)-2,3-dihydro-4H-[1,4]oxazino[2,3-f]quinazolin-4-yl)-4-(pyrrolidin-1-yl)but-2-en-1-one | 557 | (400 MHz, DMSO-d6) δ 9.83 (s, 1H), 8.61 (d, J = 4.8 Hz, 1H), 8.47 (s, 1H), 8.03-8.00 (m, 1H), 7.92-7.84 (m, 2H), 7.69-7.65 (m, 1H), 7.60-7.57 (m, 1H), 7.39-7.35 (m, 1H), 7.32-7.25 (m, 2H), 6.88-6.82 (m, 1H), 6.61-6.56 (m, 1H), 5.32 (s, 2H), 4.66 (t, J = 4.7 Hz, 2H), 4.05 (t, 2H), 3.36-3.30 (m, 2H), 2.61-2.53 (m, 4H), 1.78-1.68 (m, 4H). |
| 107 | VIII-5 | 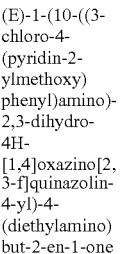 | 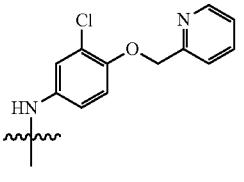 [SMILES: *Nc1ccc(OCc2ccccn2)c(Cl)c1] | (E)-1-(10-((3-chloro-4-(pyridin-2-ylmethoxy)phenyl)amino)-2,3-dihydro-4H-[1,4]oxazino[2,3-f]quinazolin-4-yl)-4-(piperidin-1-yl)but-2-en-1-one | 571 | (400 MHz, DMSO-d₆) δ 9.83 (s, 1H), 8.63-8.56 (m, 1H), 8.47 (s, 1H), 8.01 (d, J = 2.6 Hz, 1H), 7.92-7.71 (m, 2H), 7.72-7.65 (m, 1H), 7.59 (d, J = 7.8 Hz, 1H), 7.42-7.34 (m, 1H), 7.34-7.23 (m, 2H), 6.92-6.61 (m, 2H), 5.31 (s, 2H), 4.68 (t, J = 4.7 Hz, 2H), 4.07 (t, J = 4.6 Hz, 2H), 3.36-3.30 (m, 4H), 1.86-1.30 (m, 8H). |

-continued

| Example No. | Starting Intermediate No. | R¹X | N-R¹² / R¹¹ | Name | LCMS m/z = (M + H)⁺ | HNMR |
|---|---|---|---|---|---|---|
| 108 | VIII-5 | 3-chloro-4-(pyridin-2-ylmethoxy)aniline fragment | 4-acetylpiperazin-1-yl | (E)-4-(4-acetylpiperazin-1-yl)-1-(10-((3-chloro-4-(pyridin-2-ylmethoxy)phenyl)amino)-2,3-dihydro-4H-[1,4]oxazino[2,3-f]quinazolin-4-yl)but-2-en-1-one | 614 | (400 MHz, DMSO-d₆) δ 9.86 (s, 1H), 8.65-8.56 (m, 1H), 8.47 (s, 1H), 8.00 (s, 1H), 7.96-7.72 (m, 2H), 7.71-7.63 (m, 1H), 7.58 (d, J = 7.8 Hz, 1H), 7.41-7.35 (m, 1H), 7.35-7.23 (m, 2H), 6.88-6.77 (m, 1H), 6.75-6.58 (m, 1H), 5.31 (s, 2H), 4.67 (t, J = 4.7 Hz, 2H), 4.05 (t, J = 4.6 Hz, 2H), 3.52-3.35 (m, 6H), 2.79-2.51 (m, 4H), 2.00 (s, 3H). |
| 109 | VIII-5 | 3-chloro-4-(pyridin-2-ylmethoxy)aniline fragment | cyclobutyl-NH | (E)-1-(10-((3-chloro-4-(pyridin-2-ylmethoxy)phenyl)amino)-2,3-dihydro-4H-[1,4]oxazino[2,3-f]quinazolin-4-yl)-4-(cyclobutylamino)but-2-en-1-one | 557 | (400 MHz, DMSO-d₆) δ 9.83 (s, 1H), 8.63-8.59 (m, 1H), 8.50-8.45 (m, 1H), 8.01 (d, J = 2.6 Hz, 1H), 7.93-7.82 (m, 2H), 7.71-7.65 (m, 1H), 7.58 (d, J = 7.8 Hz, 1H), 7.41-7.35 (m, 1H), 7.33-7.24 (m, 2H), 6.91-6.83 (m, 1H), 6.59 (d, J = 13.9 Hz, 1H), 5.32 (s, 2H), 4.65 (t, J = 4.6 Hz, 2H), 4.10-4.00 (m, 2H), 3.35-3.34 (m, 1H), 3.32 (d, J = 6.3 Hz, 2H), 3.24-3.20 (m, 1H), 2.13-2.04 (m, 2H), 1.70 (d, J = 9.1 Hz, 2H), 1.65-1.55 (m, 2H). |
| 110 | VIII-5 | 3-chloro-4-(pyridin-2-ylmethoxy)aniline fragment | N(cyclobutyl)(methyl) | (E)-1-(10-((3-chloro-4-(pyridin-2-ylmethoxy)phenyl)amino)-2,3-dihydro-4H-[1,4]oxazino[2,3-f]quinazolin-4-yl)-4-(cyclobutyl(methyl)amino)but-2-en-1-one | 571 | (400 MHz, DMSO-d₆) δ 9.83 (s, 1H), 8.64-8.59 (m, 1H), 8.46 (s, 1H), 8.01 (d, J = 2.5 Hz, 1H), 7.94-7.77 (m, 2H), 7.70-7.63 (m, 1H), 7.58 (d, J = 7.8 Hz, 1H), 7.41-7.34 (m, 1H), 7.31-7.24 (m, 2H), 6.87-6.77 (m, 1H), 6.62-6.52 (m, 1H), 5.31 (s, 2H), 4.66 (t, J = 4.6 Hz, 2H), 4.04 (t, J = 4.6 Hz, 2H), 3.03 (d, J = 5.9 Hz, 2H), 2.90-2.80 (m, 1H), 2.04 (s, 3H), 2.01-1.92 (m, 2H), 1.82-1.71 (m, 2H), |

-continued

| Example No. | Starting Intermediate No. | R¹X |  R¹¹ | Example compound Name | LCMS m/z = (M + H)⁺ | HNMR |
|---|---|---|---|---|---|---|
| | | | | | | 1.64-1.53 (m, 2H). |
| 111 | VIII-5 |  | 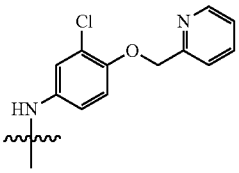 [SMILES: *Nc1ccc(OCc2ccccn2)c(Cl)c1] | (E)-1-(10-((3-chloro-4-(pyridin-2-ylmethoxy)phenyl)amino)-2,3-dihydro-4H-[1,4]oxazino[2,3-f]quinazolin-4-yl)-4-(isopropyl(methyl)amino)but-2-en-1-one | 559 | (400 MHz, DMSO-d₆) δ 9.83 (s, 1H), 8.63-8.58 (m, 1H), 8.46 (s, 1H), 8.01 (d, J = 2.6 Hz, 1H), 7.92-7.86 (m, 1H), 7.80 (s, 1H), 7.69-7.64 (m, 1H), 7.58 (d, J = 7.8 Hz, 1H), 7.41-7.35 (m, 1H), 7.31-7.25 (m, 2H), 6.86-6.77 (m, 1H), 6.64-6.55 (m, 1H), 5.31 (s, 2H), 4.66 (t, J = 4.6 Hz, 2H), 4.04 (t, J = 4.7 Hz, 2H), 3.22-3.18 (m, 2H), 2.87-2.76 (m, 1H), 2.13 (s, 3H), 0.96 (d, J = 6.5 Hz, 6H). |

Example 112

Preparation of (S,E)-1-(10-((3-chloro-4-(pyridin-2-ylmethoxy)phenyl)amino)-2,3-dihydro-4H-[1,4]oxazino[2,3-f]quinazolin-4-yl)-3-(1-methylpyrrolidin-2-yl)prop-2-en-1-one

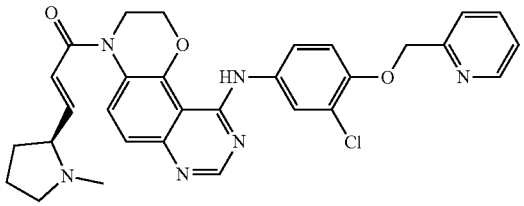 [SMILES: CN1CCC[C@H]1/C=C/C(=O)N1CCOc2c1ccc1ncnc(Nc3ccc(OCc4ccccn4)c(Cl)c3)c21]

Step 1) Preparation of diethyl (2-(10-((3-chloro-4-(pyridin-2-ylmethoxy)phenyl)amino)-2,3-dihydro-4H-[1,4]oxazino[2,3-f]quinazolin-4-yl)-2-oxoethyl) phosphate

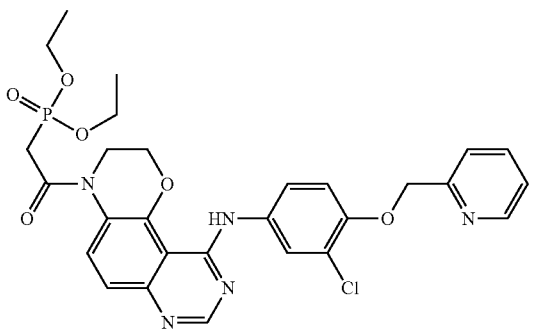 [SMILES: CCOP(=O)(CC(=O)N1CCOc2c1ccc1ncnc(Nc3ccc(OCc4ccccn4)c(Cl)c3)c21)OCC]

N-(3-chloro-4-(pyridin-2-ylmethoxy)phenyl)-3,4-dihydro-2H-[1,4]oxazino[2,3-f]quinazolin-10-amine (VIII-5) (210 mg, 0.5 mmol), 2-(diethoxyphosphoryl)acetic acid (0.5 mmol) were dissolved in tetrahydrofuran, to which N,N'-carbonyldiimidazole (81 mg, 0.5 mmol) was added, stirred at room temperature until the reaction was completed. Water and ethyl acetate were added for extraction, the organic phase was concentrated and purified using column chromatography to afford 253 mg of yellow solid with a yield of 85%. MS: 598[M+H]⁺.

Step 2) Preparation of (S,E)-1-(10-((3-chloro-4-(pyridin-2-ylmethoxy)phenyl)amino)-2,3-dihydro-4H-[1,4]oxazino[2,3-f]quinazolin-4-yl)-3-(1-methylpyrrolidin-2-yl)prop-2-en-1-one diethyl (2-(10-((3-chloro-4-(pyridin-2-ylmethoxy)phenyl)amino)-2,3-dihydro-4H-[1,4]oxazino[2,3-f]quinazolin-4-yl)-2-oxoethyl)phosphate (253 mg, 0.43 mmol) was dissolved in tetrahydrofuran, which was cooled to −78° C., and 1 mol/l of toluene solution of bistrimethylsilylamide lithium (0.83 mL, 0.83 mmol) was added dropwise, and stirred until the all of the materials were disappeared. (S)-1-methylpyrrolidinyl-2-carbaldehyde (48.6 mg, 0.43 mmol) was added, the reaction was warmed to room temperature and stirred until the reaction was completed. Water and ethyl acetate were added for extraction, the organic phase was concentrated and purified using column chromatography to afford 167 mg of off-white solid with a yield of 70%. ¹H NMR (300 MHz, DMSO-d₆) δ 9.82 (s, 1H), 8.65-8.56 (m, 1H), 8.46 (s, 1H), 8.01 (d, J=2.6 Hz, 1H), 7.95-7.72 (m, 2H), 7.71-7.61 (m, 1H), 7.58 (d, J=7.9 Hz, 1H), 7.40-7.32 (m, 1H), 7.32-7.26 (m, 2H), 6.77-6.64 (m, 1H), 6.64-6.48 (m, 1H), 5.31 (s, 2H), 4.66 (s, 2H), 4.16-3.92 (m, 2H), 3.09-2.94 (m, 1H), 2.91-2.74 (m, 1H), 2.29-2.11 (m, 4H), 2.06-1.91 (m, 1H), 1.82-1.64 (m, 2H), 1.62-1.44 (m, 1H); MS: 557[M+H]⁺.

Example 113

Preparation of 1-(10-((3-chloro-4-(pyridin-2-yl-methoxy)phenyl)amino)-2,3-dihydro-4H-[1,4]oxazino[2,3-f]quinazolin-4-yl)but-2-yne-1-one

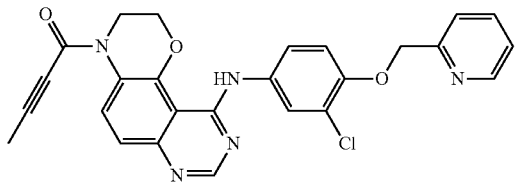 [SMILES: CC#CC(=O)N1CCOc2c1ccc1ncnc(Nc3ccc(OCc4ccccn4)c(Cl)c3)c21]

But-2-ynoic acid (42 mg, 0.5 mmol) was dissolved in dichloromethane, and 0.05 mL of dimethylformamide was added dropwise, which was cooled in an ice bath and then oxalyl chloride (32 mg, 0.25 mmol) was added. After stirring for 0.5 h, N-(3-chloro-4-(pyridin-2-ylmethoxy)phenyl)-3,4-dihydro-2H-[1,4]oxazino[2,3-f]quinazolin-10-amine (VIII-5)(210 mg, 0.5 mmol) was added, and the reaction was warmed to room temperature and stirred until the reaction was completed. The reaction was quenched by potassium carbonate aqueous solution, extracted with ethyl acetate, and the organic phase was concentrated and purified using column chromatography to afford 75 mg of off-white solid product, with a yield of 31%. $^1$H NMR (400 MHz, DMSO-$d_6$) δ 9.82 (s, 1H), 8.63-8.59 (m, 1H), 8.46 (s, 1H), 8.40-8.34 (m, 1H), 8.01-7.97 (m, 1H), 7.92-7.86 (m, 1H), 7.69-7.63 (m, 1H), 7.60-7.57 (m, 1H), 7.40-7.36 (m, 1H), 7.33-7.25 (m, 2H), 5.34-5.28 (m, 2H), 4.76-4.68 (m, 2H), 4.28 (s, 2H), 2.14 (s, 3H). MS: 486[M+H]$^+$.

Example 114: Preparation of (R,E)-1-(10-(3-chloro-4-(pyridin-2-ylmethoxy)phenyl)amino)-2,3-dihydro-4H-[1,4]oxazino[2,3-f]quinazolin-4-yl)-3-(1-methylpyrrolidin-2-yl)prop-2-en-1-one Step 1): Preparation of diethyl (2-(10-((3-chloro-4-(pyridin-2-ylmethoxy)phenyl)amino)-2,3-dihydro-4H-[1,4]oxazino[2,3-f]quinazolin-4-yl)-2-oxoethyl)phosphonate

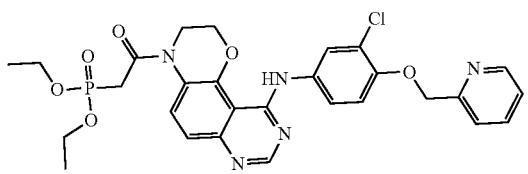 [SMILES: CCOP(=O)(CC(=O)N1CCOc2c1ccc1ncnc(Nc3ccc(OCc4ccccn4)c(Cl)c3)c21)OCC]

N-(3-chloro-4-(pyridin-2-ylmethoxy)phenyl)-3,4-dihydro-2H-[1,4]oxazino[2,3-f]quinazolin-10-amine (210 mg, 0.5 mmol), 2-(diethoxyphosphoryl)acetic acid (98 mg, 0.5 mmol) were dissolved in tetrahydrofuran, to which N,N'-carbonyldiimidazole (81 mg, 0.5 mmol) was added, the solution was stirred in a 40° C. oil bath until the reaction was completed. Water and ethyl acetate were added for extraction, the organic phase was concentrated and purified using column chromatography to afford 254 mg of yellow solid with a yield of 85%. MS: 598[M+H]$^+$.

Step 2) Preparation of (R,E)-1-(10-(3-chloro-4-(pyridin-2-ylmethoxy)phenyl)amino)-2,3-dihydro-4H-[1,4]oxazino[2,3-f]quinazolin-4-yl)-3-(1-methylpyrrolidinyl-2-yl)prop-2-en-1-one

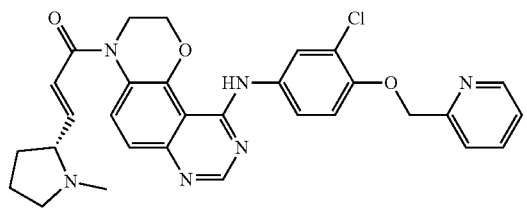 [SMILES: CN1CCC[C@@H]1/C=C/C(=O)N1CCOc2c1ccc1ncnc(Nc3ccc(OCc4ccccn4)c(Cl)c3)c21]

diethyl (2-(10-((3-chloro-4-(pyridin-2-ylmethoxy)phenyl)amino)-2,3-dihydro-4H-[1,4]oxazino[2,3-f]quinazolin-4-yl)-2-oxoethyl)phosphonate (254 mg, 0.43 mmol) was dissolved in tetrahydrofuran, cooled to −78° C., and 1 mol/l of toluene solution of bistrimethylsilylamide lithium (0.65 mL, 0.65 mmol) was added dropwise, which was stirred until the all of the materials were disappeared. (R)-1-methylpyrrolidinyl-2-carbaldehyde (48.6 mg, 0.43 mmol) was added, and the reaction was warmed to room temperature and stirred until the reaction was completed. Water and ethyl acetate were added for extraction, the organic phase was concentrated and separated by high performance liquid chromatography to afford 154 mg of white solid with a yield of 65%. $^1$H NMR (400 MHz, DMSO-$d_6$) δ 9.82 (s, 1H), 8.60 (d, J=4.9 Hz, 1H), 8.46 (s, 1H), 8.01 (d, J=2.5 Hz, 1H), 7.92-7.74 (m, 2H), 7.69-7.64 (m, 1H), 7.58 (d, J=7.8 Hz, 1H), 7.40-7.34 (m, 1H), 7.31-7.24 (m, 2H), 6.73-6.66 (m, 1H), 6.55 (d, J=15.4 Hz, 1H), 5.31 (s, 2H), 4.70-4.63 (m, 2H), 4.11-3.97 (m, 2H), 2.99 (d, J=8.2 Hz, 1H), 2.82-2.74 (m, 1H), 2.20 (s, 3H), 2.16 (d, J=8.7 Hz, 1H), 2.06-1.92 (m, 1H), 1.71 (d, J=9.4 Hz, 2H), 1.63-1.49 (m, 1H); MS: 557[M+H]$^+$.

Example 115: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-(4-hydroxypiperidin-1-yl)but-2-en-1-one

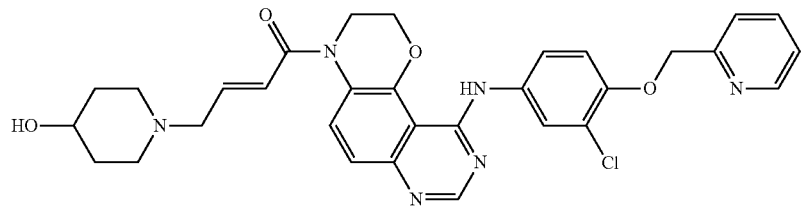 [SMILES: O=C(/C=C/CN1CCC(O)CC1)N1CCOc2c1ccc1ncnc(Nc3ccc(OCc4ccccn4)c(Cl)c3)c21]

N-(3-chloro-4-(pyridin-2-ylmethoxy)phenyl)-3,4-dihydro-2H-[1,4]oxazino[2,3-f]quinazolin-10-amine (210 mg, 0.5 mmol) was dissolved in dimethylformamide, to which 4-bromocrotonyl chloride (91 mg, 0.5 mmol) was added, and stirred at room temperature until the reaction was completed. The reaction was quenched by adding water, extracted with ethyl acetate, the organic phase was concentrated and directly dissolved in acetonitrile, to which diisopropylethylamine (129 mg, 1 mmol) and piperidin-4-ol (101 mg, 1 mmol) were added, and stirred at room temperature until the reaction was completed. The reaction was quenched by the addition of water, extracted with ethyl acetate, and the organic phase was concentrated and purified by high performance liquid chromatography to afford 97 mg of white solid with a yield of 33%. $^1$H NMR (400 MHz, DMSO-$d_6$) δ 9.81 (s, 1H), 8.60 (d, J=4.8 Hz, 1H), 8.46 (s, 1H), 8.01 (d, J=2.6 Hz, 1H), 7.92-7.85 (m, 1H), 7.81 (s, 1H), 7.71-7.63 (m, 1H), 7.58 (d, J=7.9 Hz, 1H), 7.41-7.33 (m, 1H), 7.28 (t, J=9.4 Hz, 2H), 6.86-6.76 (m, 1H), 6.57 (d, J=15.4 Hz, 1H), 5.31 (s, 2H), 4.66 (t, J=4.6 Hz, 2H), 4.50 (d, J=4.1 Hz, 1H), 4.04 (t, J=4.7 Hz, 2H), 3.44 (s, 1H), 3.11 (d, J=5.6 Hz, 2H), 2.69 (d, J=12.0 Hz, 2H), 2.07 (t, J=10.7 Hz, 2H), 1.70 (d, J=12.4 Hz, 2H), 1.37 (d, J=11.1 Hz, 2H); MS: 587[M+H]$^+$.

Example 116: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-(4-hydroxyl-4-methylpiperidin-1-yl)but-2-en-1-one

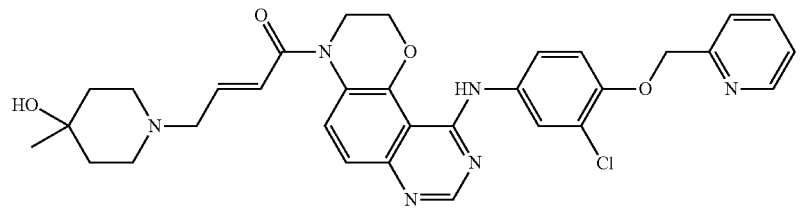 [SMILES: CC1(O)CCN(C/C=C/C(=O)N2CCOc3c2ccc2ncnc(Nc4ccc(OCc5ccccn5)c(Cl)c4)c32)CC1]

It was prepared by a method similar to that of Example 115, except that piperidin-4-ol was replaced by the same molar equivalent of 4-methylpiperidin-4-ol. $^1$H NMR (400 MHz, DMSO-$d_6$) δ 9.81 (s, 1H), 8.60 (d, J=4.9 Hz, 1H), 8.45 (s, 1H), 8.00 (s, 1H), 7.94-7.72 (m, 2H), 7.69-7.61 (m, 1H), 7.58 (d, J=7.8 Hz, 1H), 7.41-7.32 (m, 1H), 7.26 (t, J=8.7 Hz, 2H), 6.86-6.74 (m, 1H), 6.62-6.46 (m, 1H), 5.30 (s, 2H), 4.65 (t, J=4.7 Hz, 2H), 4.10 (s, 1H), 4.03 (t, J=4.8 Hz, 2H), 3.19-3.06 (m, 2H), 2.46-2.28 (m, 4H), 1.51-1.26 (m, 4H), 1.08 (s, 3H); MS: 601[M+H]$^+$.

Example 117: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-(4-(hydroxymethyl)piperidin-1-yl)but-2-en-1-one

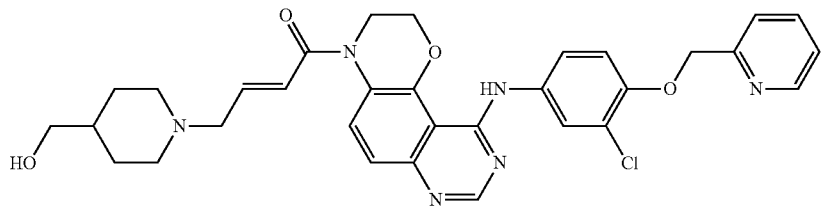 [SMILES: O=C(/C=C/CN1CCC(CO)CC1)N1CCOc2c1ccc1ncnc(Nc3ccc(OCc4ccccn4)c(Cl)c3)c21]

It was prepared by a method similar to that of Example 115, except that piperidin-4-ol was replaced by the same molar equivalent of piperidin-4-ylmethanol. $^1$H NMR (400 MHz, DMSO-$d_6$) δ 9.81 (s, 1H), 8.60 (d, J=4.8 Hz, 1H), 8.46 (s, 1H), 8.01 (d, J=2.5 Hz, 1H), 7.88 (t, J=8.0 Hz, 2H), 7.70-7.62 (m, 1H), 7.58 (d, J=7.9 Hz, 1H), 7.40-7.33 (m, 1H), 7.28 (t, J=9.4 Hz, 2H), 6.87-6.75 (m, 1H), 6.57 (d, J=15.3 Hz, 1H), 5.31 (s, 2H), 4.66 (d, J=5.0 Hz, 2H), 4.37 (t, J=5.3 Hz, 1H), 4.04 (s, 2H), 3.23 (t, J=5.9 Hz, 2H), 3.12 (d, J=5.7 Hz, 2H), 2.83 (d, J=11.1 Hz, 2H), 1.92 (t, J=11.4 Hz, 2H), 1.63 (d, J=12.6 Hz, 2H), 1.37-1.25 (m, 1H), 1.18-1.04 (m, 2H); MS: 601[M+H]$^+$.

Example 118: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-(4-fluoropiperidin-1-yl)but-2-en-1-one

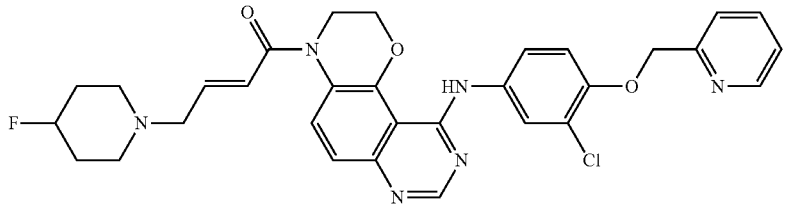

It was prepared by a method similar to that of Example 115, except that piperidin-4-ol was replaced by the same molar equivalent of 4-fluoropiperidine. $^1$H NMR (400 MHz, DMSO-$d_6$) δ 9.81 (s, 1H), 8.63-8.57 (m, 1H), 8.46 (s, 1H), 8.01 (d, J=2.5 Hz, 1H), 7.93-7.76 (m, 2H), 7.70-7.62 (m, 1H), 7.58 (d, J=7.9 Hz, 1H), 7.40-7.34 (m, 1H), 7.32-7.22 (m, 2H), 6.87-6.77 (m, 1H), 6.59 (d, J=15.2 Hz, 1H), 5.31 (s, 2H), 4.66 (t, J=4.7 Hz, 3H), 4.04 (t, J=4.4 Hz, 2H), 3.15 (d, J=5.6 Hz, 2H), 2.55 (d, J=6.9 Hz, 2H), 2.34 (s, 2H), 1.91-1.77 (m, 2H), 1.70 (s, 2H); MS: 589[M+H]$^+$.

Example 119: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-((2-methoxyethyl)(methyl)amino)but-2-en-1-one

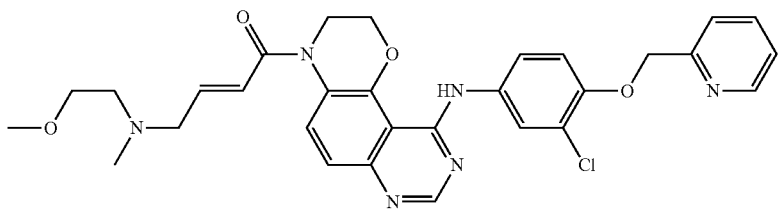 [SMILES: COCCN(C)C/C=C/C(=O)N1CCOc2c1ccc1ncnc(Nc3ccc(OCc4ccccn4)c(Cl)c3)c21]

It was prepared by a method similar to that of Example 115, except that piperidin-4-ol was replaced by the same molar equivalent of N-(2-methoxyethyl)methylamine. $^1$H NMR (400 MHz, DMSO-$d_6$) δ 9.81 (s, 1H), 8.60 (d, J=4.8 Hz, 1H), 8.46 (s, 1H), 8.01 (d, J=2.6 Hz, 1H), 7.93-7.73 (m, 2H), 7.70-7.61 (m, 1H), 7.58 (d, J=7.8 Hz, 1H), 7.42-7.31 (m, 1H), 7.31-7.18 (m, 2H), 6.87-6.73 (m, 1H), 6.64-6.51 (m, 1H), 5.30 (s, 2H), 4.65 (t, J=4.7 Hz, 2H), 4.04 (t, J=4.7 Hz, 2H), 3.40 (t, J=5.8 Hz, 2H), 3.24-3.14 (m, 5H), 2.55-2.51 (m, 2H), 2.21 (s, 3H); MS: 575[M+H]$^+$.

Example 120: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-((3-hydroxypropyl)(methyl)amino)but-2-en-1-one

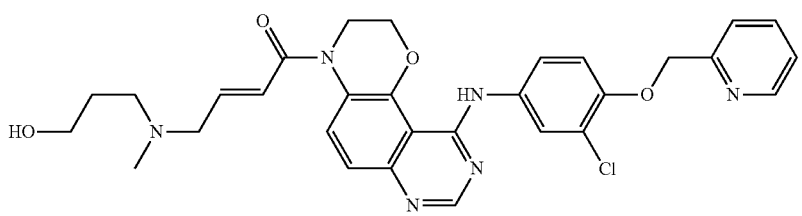 [SMILES: CN(C/C=C/C(=O)N1CCOc2c1ccc1ncnc(Nc3ccc(OCc4ccccn4)c(Cl)c3)c21)CCCO]

It was prepared by a method similar to that of Example 115, except that piperidin-4-ol was replaced by the same molar equivalent of 3-(methylamino)-1-propanol. $^1$H NMR (400 MHz, DMSO-d$_6$) δ 9.81 (s, 1H), 8.60 (d, J=4.8 Hz, 1H), 8.46 (s, 1H), 8.01 (d, J=2.6 Hz, 1H), 7.92-7.76 (m, 2H), 7.71-7.63 (m, 1H), 7.58 (d, J=7.9 Hz, 1H), 7.37 (t, J=6.3 Hz, 1H), 7.32-7.23 (m, 2H), 6.88-6.77 (m, 1H), 6.58 (d, J=15.2 Hz, 1H), 5.31 (s, 2H), 4.65 (d, J=4.8 Hz, 2H), 4.39 (s, 1H), 4.04 (t, J=4.6 Hz, 2H), 3.44 (d, J=5.8 Hz, 2H), 3.15 (d, J=5.7 Hz, 2H), 2.39 (t, J=7.3 Hz, 2H), 2.17 (s, 3H), 1.62-1.52 (m, 2H); MS: 575[M+H]$^+$.

Example 121: Preparation of (S,E)-1-(10-((3-chloro-4-(pyridin-2-ylmethoxy)phenyl)amino)-2,3-dihydro-4H-[1,4]oxazino[2,3-f]quinazolin-4-yl)-4-(2,4-dimethylpiperazin-1-yl)but-2-en-1-one

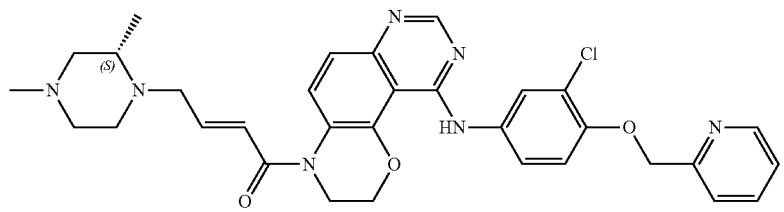

It was prepared by a method similar to that of Example 115, except that piperidin-4-ol was replaced by the same molar equivalent of (S)-1,3-dimethylpiperazine. $^1$H NMR (400 MHz, DMSO-d$_6$) δ 9.80 (s, 1H), 8.59 (d, J=4.7 Hz, 1H), 8.45 (s, 1H), 8.00 (d, J=2.6 Hz, 1H), 7.87 (t, J=7.7, 1.9 Hz, 1H), 7.84-7.69 (m, 1H), 7.69-7.62 (m, 1H), 7.57 (d, J=7.8 Hz, 1H), 7.41-7.32 (m, 1H), 7.26 (t, J=9.3 Hz, 2H), 6.89-6.78 (m, 1H), 6.65-6.51 (m, 1H), 5.29 (s, 2H), 4.72-4.56 (m, 2H), 4.13-3.90 (m, 2H), 3.55-3.41 (m, 1H), 3.05-2.94 (m, 1H), 2.72-2.62 (m, 1H), 2.58-2.52 (m, 1H), 2.47-2.30 (m, 2H), 2.28-2.20 (m, 1H), 2.10 (s, 3H), 2.04-1.96 (m, 1H), 1.74 (t, J=10.1 Hz, 1H), 0.96 (d, J=6.2 Hz, 3H); MS: 600[M+H]$^+$.

Example 122: Preparation of (E)-1-(10-((3-chloro-4-(pyridin-2-ylmethoxy)phenyl)amino)-2,3-dihydro-4H-[1,4]oxazino[2,3-f]quinazolin-4-yl)-4-((2-hydroxyethyl)(methyl)amino)but-2-en-1-one

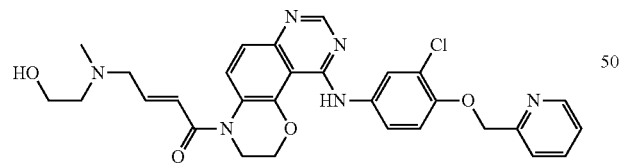

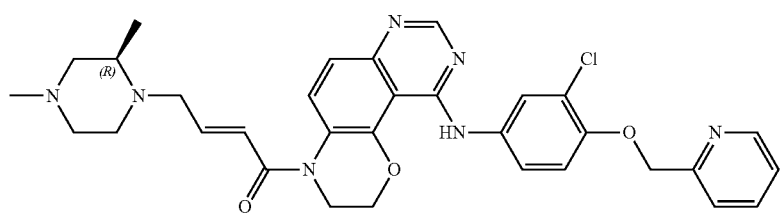

It was prepared by a method similar to that of Example 115, except that piperidin-4-ol was replaced by the same molar equivalent of 2-methylaminoethanol. $^1$H NMR (400 MHz, DMSO-$d_6$) δ 9.81 (s, 1H), 8.60 (d, J=4.8 Hz, 1H), 8.46 (s, 1H), 8.01 (d, J=2.6 Hz, 1H), 7.91-7.79 (m, 2H), 7.70-7.63 (m, 1H), 7.58 (d, J=7.8 Hz, 1H), 7.37 (t, J=6.3 Hz, 1H), 7.34-7.23 (m, 2H), 6.89-6.78 (m, 1H), 6.61 (d, J=15.5 Hz, 1H), 5.31 (s, 2H), 4.66 (t, J=4.5 Hz, 2H), 4.38 (t, J=5.4 Hz, 1H), 4.05 (t, J=4.7 Hz, 2H), 3.52-3.44 (m, 2H), 3.20 (d, J=5.7 Hz, 2H), 2.44 (t, J=6.3 Hz, 2H), 2.22 (s, 3H); MS: 561[M+H]$^+$.

Example 123: Preparation of (R,E)-1-(10-((3-chloro-4-(pyridin-2-ylmethoxy)phenyl)amino)-2,3-dihydro-4H-[1,4]oxazino[2,3-f]quinazolin-4-yl)-4-(2,4-dimethylpiperazin-1-yl)but-2-en-1-one It was prepared by a method similar to that of Example 115, except that piperidin-4-ol was replaced by the same molar equivalent of (R)-1,3-dimethylpiperazine. $^1$H NMR (400 MHz, DMSO-$d_6$) δ 9.82 (s, 1H), 8.60 (d, J=4.8 Hz, 1H), 8.46 (s, 1H), 8.01 (d, J=2.6 Hz, 1H), 7.92-7.72 (m, 2H), 7.71-7.63 (m, 1H), 7.58 (d, J=7.8 Hz, 1H), 7.37 (t, J=6.3 Hz, 1H), 7.28 (t, J=8.8 Hz, 2H), 6.90-6.80 (m, 1H), 6.66-6.51 (m, 1H), 5.31 (s, 2H), 4.72-4.59 (m, 2H), 4.13-3.95 (m, 2H), 3.50 (d, J=15.7 Hz, 1H), 3.13-2.96 (m, 2H), 2.70 (d, J=13.2 Hz, 1H), 2.54 (s, 1H), 2.41 (s, 1H), 2.26 (t, J=10.6 Hz, 1H), 2.11 (s, 3H), 2.04 (d, J=11.1 Hz, 1H), 1.76 (s, 1H), 0.97 (d, J=6.2 Hz, 3H); MS: 600[M+H]$^+$.

Example 124: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(dimethylamino)but-2-en-1-one

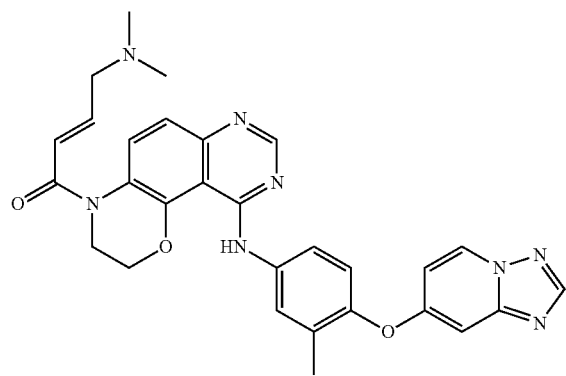 [SMILES: Cc1cc(Nc2ncnc3ccc4c(c23)OCCN4C(=O)/C=C/CN(C)C)ccc1Oc1ccn2ncnc2c1]

N-(4-([1,2,4]triazolo[1,5-a]pyridin-7-yloxy)-3-methylphenyl)-3,4-dihydro-2H-[1,4]oxazino[2,3-f]quinazolin-10-amine (213 mg, 0.5 mmol) was dissolved in dimethylformamide, to which (E)-4-(dimethylamino)but-2-enoyl chloride hydrochloride (137 mg, 0.75 mmol) was added at room temperature, and stirred at room temperature until the reaction was completed. The reaction was quenched by the addition of potassium carbonate aqueous solution, extracted with ethyl acetate, and the organic phase was concentrated and purified by high performance liquid chromatography to afford 200 mg of white solid with a yield of 75%. $^1$H NMR (400 MHz, DMSO-$d_6$) δ 9.93 (s, 1H), 8.94 (d, J=7.5 Hz, 1H), 8.50 (s, 1H), 8.38 (s, 1H), 7.97-7.69 (m, 3H), 7.32 (d, J=9.0 Hz, 1H), 7.22 (d, J=8.6 Hz, 1H), 7.08-6.98 (m, 1H), 6.87-6.72 (m, 2H), 6.64-6.52 (m, 1H), 4.69 (t, J=4.6 Hz, 2H), 4.06 (t, J=4.5 Hz, 2H), 3.14-3.01 (m, 2H), 2.33-2.03 (m, 9H); MS: 537[M+H]*.

Example 125: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(dimethylamino)but-2-en-1-one

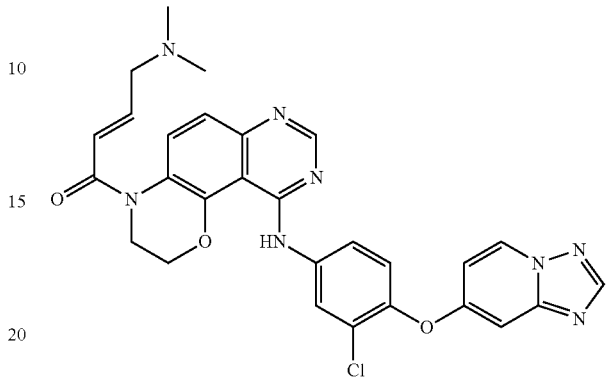

N-(4-([1,2,4]triazolo[1,5-a]pyridin-7-yloxy)-3-chlorophenyl)-3,4-dihydro-2H-[1,4]oxazino[2,3-f]quinazolin-10-amine (223 mg, 0.5 mmol) was dissolved in dimethylformamide, to which (E)-4-(dimethylamino)but-2-enoyl chloride hydrochloride (137 mg, 0.75 mmol) was added at room temperature, and stirred at room temperature until the reaction was completed. The reaction was quenched by the addition of potassium carbonate aqueous solution, extracted with ethyl acetate, and the organic phase was concentrated and purified by high performance liquid chromatography to afford 195 mg of white solid with a yield of 70%. $^1$H NMR (400 MHz, DMSO-$d_6$) δ 10.03 (s, 1H), 8.97 (d, J=7.3 Hz, 1H), 8.56 (s, 1H), 8.41 (s, 1H), 8.32 (d, J=2.5 Hz, 1H), 7.98-7.93 (m, 1H), 7.93-7.73 (m, 1H), 7.47 (d, J=8.8 Hz, 1H), 7.34 (d, J=9.1 Hz, 1H), 7.11-7.02 (m, 1H), 6.92 (d, J=2.6 Hz, 1H), 6.87-6.77 (m, 1H), 6.65-6.52 (m, 1H), 4.69 (t, 2H), 4.06 (t, J=4.7 Hz, 2H), 3.11-3.02 (m, 2H), 2.17 (s, 6H); MS: 557[M+H]$^+$.

Example 126: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(4-methylpiperazin-1-yl)but-2-en-1-one

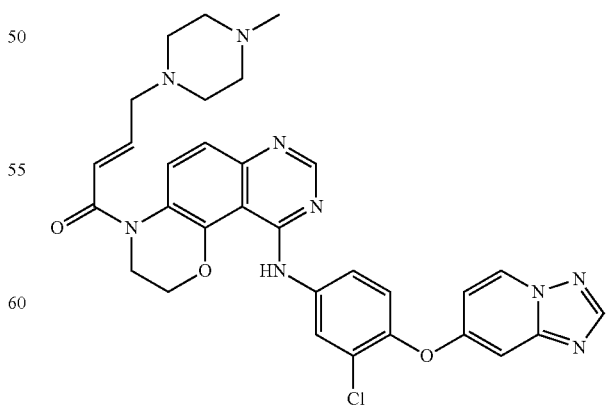

N-(4-([1,2,4]triazolo[1,5-a]pyridin-7-yloxy)-3-chlorophenyl)-3,4-dihydro-2H-[1,4]oxazino[2,3-f]quinazolin-10- amine (223 mg, 0.5 mmol) was dissolved in dimethylformamide, to which 4-bromocrotonyl chloride (91 mg, 0.5 mmol) was added, and stirred at room temperature until the reaction was completed. The reaction was quenched by adding water, extracted with ethyl acetate, the organic phase was concentrated and directly dissolved in acetonitrile, to which diisopropylethylamine (129 mg, 1 mmol) and 1-methylpiperazine (100 mg, 1 mmol) were added, and stirred at room temperature until the reaction was completed. The reaction was quenched by the addition of water, extracted with ethyl acetate, the organic phase was concentrated and purified by high-performance liquid chromatography to afford a white solid 125 mg with a yield of 41%. $^1$H NMR (400 MHz, MeOH-d$_4$) δ 8.66 (d, J=7.5 Hz, 1H), 8.46-8.38 (m, 2H), 8.21-8.18 (m, 2H), 7.73 (d, J=2.6 Hz, 1H), 7.71 (d, J=2.6 Hz, 1H), 7.29-7.24 (m, 2H), 7.00-6.96 (m, 1H), 6.91-6.83 (m, 1H), 6.74 (d, J=2.5 Hz, 1H), 6.58 (d, J=15.3 Hz, 1H), 4.64 (t, J=4.7 Hz, 2H), 4.06 (t, 2H), 3.18 (dd, J=6.1, 1.6 Hz, 2H), 2.76-2.62 (m, 4H), 2.61-2.45 (m, 4H), 2.40 (s, 3H); MS: 612[M+H]$^+$.

Example 127: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(isopropyl(methyl)amino)but-2-en-1-one

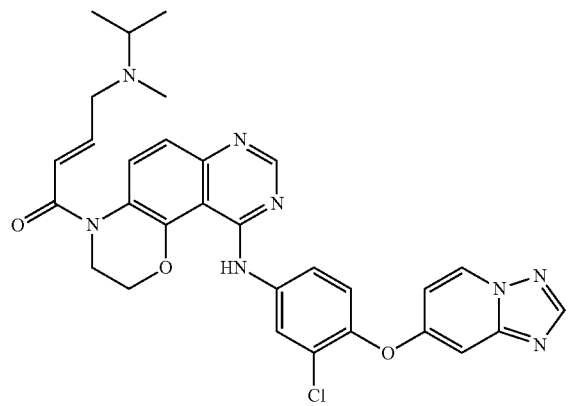 [SMILES: CC(C)N(C)C/C=C/C(=O)N1CCOc2c1ccc1ncnc(Nc3ccc(Oc4ccn5ncnc5c4)c(Cl)c3)c21]

It was prepared by a method similar to that of Example 126, except that 1-methylpiperazine was replaced by the same molar equivalent of N-isopropylmethylamine. $^1$H NMR (400 MHz, MeOH-d$_4$) δ 8.65 (d, J=7.5 Hz, 1H), 8.40 (d, J=1.7 Hz, 2H), 8.22-8.16 (m, 2H), 7.79-7.68 (m, 2H), 7.29-7.22 (m, 2H), 6.99-6.95 (m, 1H), 6.92-6.85 (m, 1H), 6.73 (d, J=2.6 Hz, 1H), 6.68-6.62 (m, 1H), 4.64 (t, J=4.7 Hz, 2H), 4.06 (t, J=4.7 Hz, 2H), 3.41 (dd, J=6.6, 1.4 Hz, 2H), 3.06-2.98 (m, 1H), 2.30 (s, 3H), 1.06 (d, J=6.6 Hz, 6H); MS: 585[M+H]$^+$.

Example 128: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(piperidin-1-yl)but-2-en-1-one

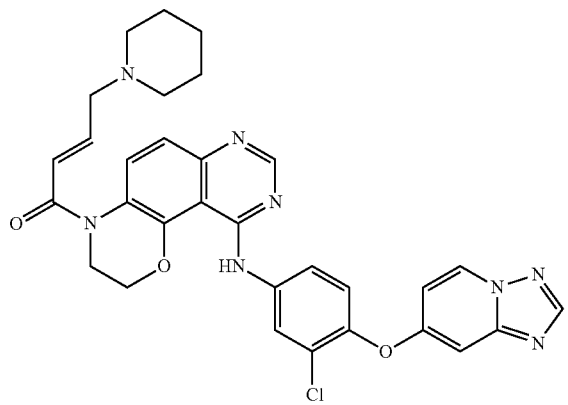 [SMILES: O=C(/C=C/CN1CCCCC1)N1CCOc2c1ccc1ncnc(Nc3ccc(Oc4ccn5ncnc5c4)c(Cl)c3)c21]

It was prepared by a method similar to that of Example 126, except that 1-methylpiperazine was replaced by the same molar equivalent of piperidine. $^1$H NMR (400 MHz, MeOH-d$_4$) δ 8.67 (d, J=7.5 Hz, 1H), 8.43 (s, 2H), 8.23-8.18 (m, 2H), 7.73 (dd, J=8.8, 2.6 Hz, 2H), 7.30-7.25 (m, 2H), 6.99 (dd, J=7.5, 2.6 Hz, 1H), 6.93-6.84 (m, 1H), 6.75 (d, J=2.6 Hz, 1H), 6.63 (d, J=15.3 Hz, 1H), 4.65 (t, J=4.7 Hz, 2H), 4.07 (t, J=4.7 Hz, 2H), 3.38-3.31 (m, 2H), 2.62 (s, 4H), 1.64-1.57 (m, 4H), 1.48-1.40 (m, 2H); MS: 597[M+H]$^+$.

Example 129: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(cyclobutyl(methyl)amino)but-2-en-1-one

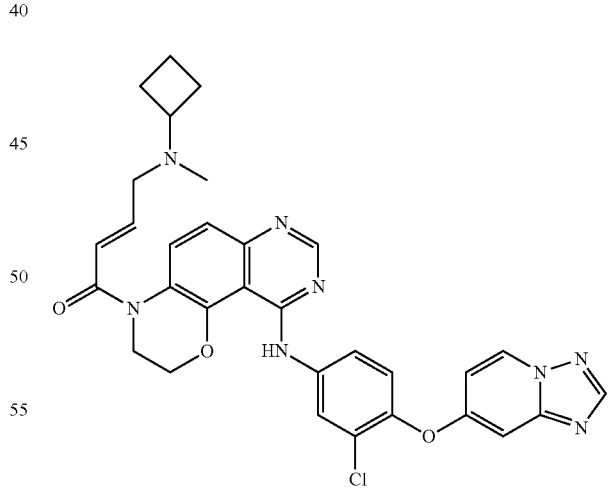

It was prepared by a method similar to that of Example 126, except that 1-methylpiperazine was replaced by the same molar equivalent of N-methylcyclobutylamine hydrochloride. $^1$H NMR (400 MHz, MeOH-d$_4$) δ 8.66 (dd, J=7.4, 0.6 Hz, 1H), 8.42 (s, 1H), 8.40 (s, 1H), 8.24-8.17 (m, 2H), 7.72 (dd, J=8.8, 2.6 Hz, 2H), 7.30-7.24 (m, 2H), 7.00-6.96 (m, 1H), 6.93-6.85 (m, 1H), 6.74 (d, J=2.6 Hz, 1H), 6.58 (d, J=15.2 Hz, 1H), 4.65 (t, J=4.6 Hz, 2H), 4.06 (t, 2H), 3.16

(dd, J=6.7, 1.4 Hz, 2H), 3.00-2.91 (m, 1H), 2.14 (s, 3H), 2.06-1.98 (m, 2H), 1.90-1.79 (m, 2H), 1.69-1.57 (m, 2H); MS: 597[M+H]⁺.

Example 130: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-((2-methoxyethyl)(methyl)amino)but-2-en-1-one

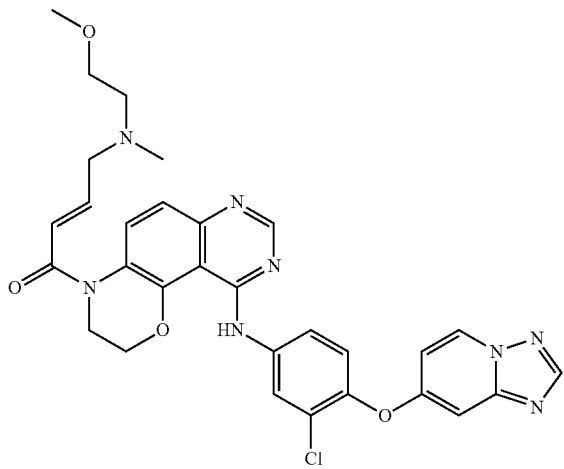 [SMILES: COCCN(C)C/C=C/C(=O)N1CCOc2c1ccc1ncnc(Nc3ccc(Oc4ccn5ncnc5c4)c(Cl)c3)c21]

It was prepared by a method similar to that of Example 126, except that 1-methylpiperazine was replaced by the same molar equivalent of N-(2-methoxyethyl)methylamine. ¹H NMR (400 MHz, MeOH-d₄) δ 8.79 (dd, J=7.5, 0.7 Hz, 1H), 8.56 (s, 1H), 8.34-8.32 (m, 2H), 7.94-7.89 (m, 1H), 7.88-7.87 (m, 1H), 7.86-7.85 (m, 1H), 7.41 (dd, J=8.9, 4.0 Hz, 2H), 7.12 (dd, J=7.5, 2.6 Hz, 1H), 7.07-6.99 (m, 1H), 6.89-6.87 (m, 1H), 6.71 (d, J=15.3 Hz, 1H), 4.77 (t, J=4.8 Hz, 2H), 4.19 (t, J=4.7 Hz, 2H), 3.55 (t, J=5.5 Hz, 2H), 3.35 (t, 2H), 3.35 (s, 3H), 2.68 (t, J=5.5 Hz, 2H), 2.37 (s, 3H); MS: 601 [M+H]⁺.

Example 131: Preparation of (E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(diethylamino)but-2-en-1-one

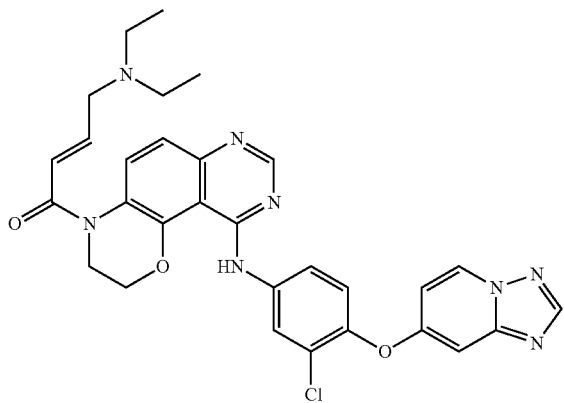 [SMILES: CCN(CC)C/C=C/C(=O)N1CCOc2c1ccc1ncnc(Nc3ccc(Oc4ccn5ncnc5c4)c(Cl)c3)c21]

It was prepared by a method similar to that of Example 126, except that 1-methylpiperazine was replaced by the same molar equivalent of diethylamine. ¹H NMR (400 MHz, MeOH-d₄) δ 8.79 (dd, J=7.5, 0.7 Hz, 1H), 8.56 (s, 1H), 8.33 (s, 1H), 8.32 (d, J=2.5 Hz, 1H), 7.91-7.88 (m, 1H), 7.88-7.86 (m, 1H), 7.86 (d, J=2.6 Hz, 1H), 7.43-7.39 (m, 2H), 7.13-7.10 (m, 1H), 7.09-7.01 (m, 1H), 6.88-6.87 (m, 1H), 6.70 (d, J=15.3 Hz, 1H), 4.77 (t, J=4.7 Hz, 2H), 4.20-4.16 (m, 2H), 3.39 (dd, J=6.3, 1.5 Hz, 2H), 2.64 (q, J=7.2 Hz, 4H), 1.12 (t, J=7.2 Hz, 6H); MS: 585 [M+H]⁺.

Example 132: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(4-methylpiperazin-1-yl)but-2-en-1-one

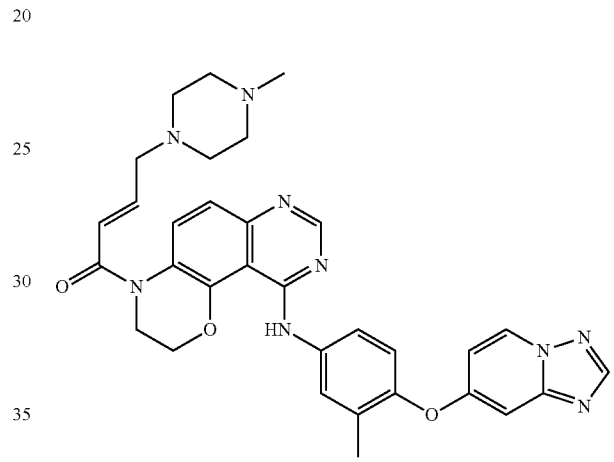

N-(4-([1,2,4]triazolo[1,5-a]pyridin-7-yloxy)-3-methylphenyl)-3,4-dihydro-2H-[1,4]oxazino[2,3-f]quinazolin-10-amine (212 mg, 0.5 mmol) was dissolved in dimethylformamide, to which 4-bromocrotonyl chloride (91 mg, 0.5 mmol) was added, and stirred at room temperature until the reaction was completed. The reaction was quenched by adding water, extracted with ethyl acetate, the organic phase was concentrated and directly dissolved in acetonitrile, to which diisopropylethylamine (129 mg, 1 mmol) and 1-methylpiperazine (100 mg, 1 mmol) were added, and stirred at room temperature until the reaction was completed. The reaction was quenched by the addition of water, extracted with ethyl acetate, and the organic phase was concentrated and purified by high performance liquid chromatography to afford 110 mg of a white solid with a yield of 37%. ¹H NMR (400 MHz, MeOH-d₄) δ 8.77 (d, J=7.5 Hz, 1H), 8.49 (s, 1H), 8.31 (s, 1H), 7.88-7.83 (m, 1H), 7.83-7.80 (m, 2H), 7.79-7.77 (m, 1H), 7.38 (d, J=9.1 Hz, 1H), 7.21 (d, J=8.5 Hz, 1H), 7.12-7.09 (m, 1H), 7.03-6.96 (m, 1H), 6.84 (d, J=2.5 Hz, 1H), 6.70 (d, J=15.3 Hz, 1H), 4.76 (t, J=4.7 Hz, 2H), 4.18 (t, J=4.7 Hz, 2H), 3.30-3.28 (m, 2H), 2.78-2.55 (m, 8H), 2.45 (s, 3H), 2.27 (s, 3H); MS: 592 [M+H]⁺.

Example 133: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(isopropyl(methyl)amino)but-2-en-1-one

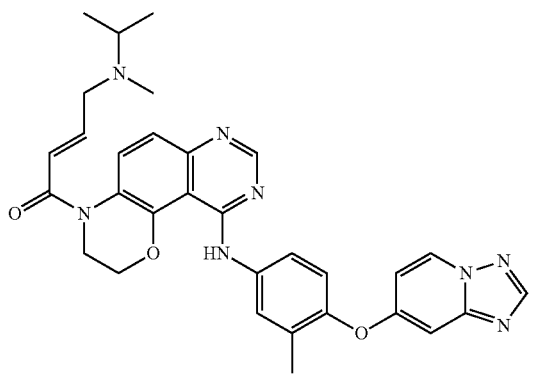

It was prepared by a method similar to that of Example 132, except that 1-methylpiperazine was replaced by the same molar equivalent of N-isopropylmethylamine. $^1$H NMR (400 MHz, MeOH-$d_4$) δ 8.76 (d, J=7.5 Hz, 1H), 8.48 (s, 1H), 8.31 (s, 1H), 7.89-7.83 (m, 1H), 7.81 (t, J=2.4 Hz, 2H), 7.78 (d, J=2.7 Hz, 1H), 7.40-7.36 (m, 1H), 7.21 (d, J=8.5 Hz, 1H), 7.12-7.08 (m, 1H), 7.06-6.98 (m, 1H), 6.84 (d, J=2.6 Hz, 1H), 6.71 (d, J=15.2 Hz, 1H), 4.76 (t, J=4.7 Hz, 2H), 4.18 (t, J=4.7 Hz, 2H), 3.41-3.39 (m, 2H), 3.03-2.96 (m, 1H), 2.32 (s, 3H), 2.27 (s, 3H), 1.13 (s, 3H), 1.12 (s, 3H); MS: 565 [M+H]$^+$.

Example 134: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(piperidin-1-yl)but-2-en-1-one

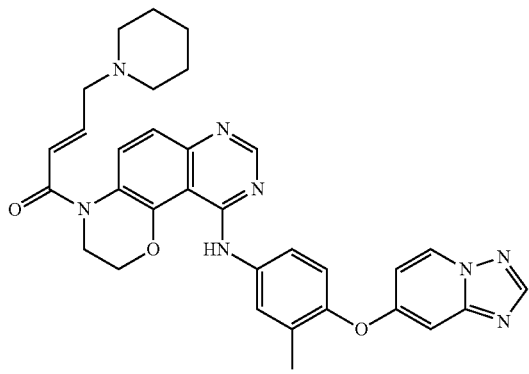 [SMILES: Cc1cc(Nc2ncnc3ccc4c(c23)OCCN4C(=O)/C=C/CN2CCN(C)CC2)ccc1Oc1ccn2ncnc2c1]

It was prepared by a method similar to that of Example 132, except that 1-methylpiperazine was replaced by the same molar equivalent of piperidine. $^1$H NMR (400 MHz, MeOH-$d_4$) δ 8.64 (d, J=7.5 Hz, 1H), 8.37 (s, 1H), 8.19 (s, 1H), 7.79-7.75 (m, 1H), 7.70-7.67 (m, 2H), 7.66 (d, J=2.7 Hz, 1H), 7.26 (d, J=9.0 Hz, 1H), 7.09 (d, J=8.4 Hz, 1H), 7.00-6.96 (m, 1H), 6.89-6.82 (m, 1H), 6.75 (s, 1H), 6.71 (d, J=2.6 Hz, 1H), 4.66 (d, J=4.7 Hz, 2H), 4.10-4.05 (m, 2H), 3.63 (d, J=6.6 Hz, 2H), 2.97-2.86 (m, 4H), 2.15 (s, 3H), 1.75-1.67 (m, 4H), 1.57-1.50 (m, 2H); MS: 577 [M+H]$^+$.

Example 135: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(cyclobutyl(methyl)amino)but-2-en-1-one

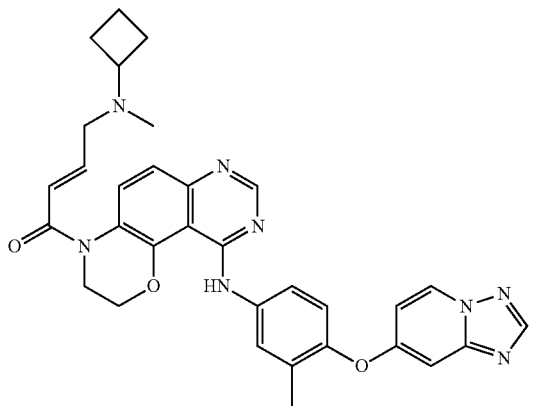 [SMILES: Cc1cc(Nc2ncnc3ccc4c(c23)OCCN4C(=O)/C=C/CN(C)C2CCC2)ccc1Oc1ccn2ncnc2c1]

It was prepared by a method similar to that of Example 132, except that 1-methylpiperazine was replaced by the same molar equivalent of N-methylcyclobutylamine hydrochloride. $^1$H NMR (400 MHz, MeOH-$d_4$) δ 8.74 (d, J=7.5 Hz, 1H), 8.50 (s, 1H), 8.45 (s, 1H), 8.29 (s, 1H), 7.88-7.81 (m, 1H), 7.80-7.75 (m, 2H), 7.34 (d, J=9.1 Hz, 1H), 7.19-7.16 (m, 1H), 7.09-7.05 (m, 1H), 7.02-6.94 (m, 1H), 6.84-6.75 (m, 2H), 4.75 (t, J=4.6 Hz, 2H), 4.18 (t, J=4.6 Hz, 2H), 3.56 (d, J=6.8 Hz, 2H), 3.42-3.37 (m, 1H), 2.66 (d, J=9.4 Hz, 2H), 2.49 (s, 3H), 2.24 (s, 3H), 2.17-2.09 (m, 2H), 1.85-1.75 (m, 2H); MS: 577 [M+H]$^+$.

Example 136: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-((2-methoxyethyl)(methyl)amino)but-2-en-1-one

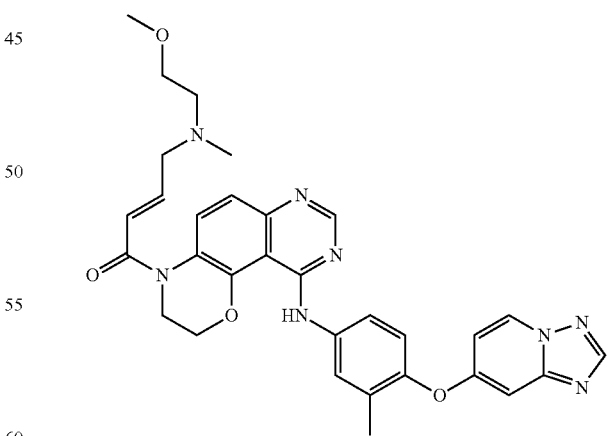

It was prepared by a method similar to that of Example 132, except that 1-methylpiperazine was replaced by the same molar equivalent of N-(2-methoxyethyl)methylamine. $^1$H NMR (400 MHz, MeOH-$d_4$) δ 8.76 (dd, J=7.6, 0.7 Hz, 1H), 8.48 (s, 1H), 8.31 (s, 1H), 7.93-7.83 (m, 1H), 7.83-7.80 (m, 2H), 7.79-7.77 (m, 1H), 7.38 (d, J=9.1 Hz, 1H), 7.21 (d, J=8.5 Hz, 1H), 7.12-7.08 (m, 1H), 7.07-6.99 (m, 1H), 6.85-6.83 (m, 1H), 6.70 (d, J=15.3 Hz, 1H), 4.76 (t, J=4.7 Hz, 2H), 4.18 (t, 2H), 3.57-3.52 (m, 2H), 3.35-3.34 (m, 5H), 2.67 (t, J=5.5 Hz, 2H), 2.35 (s, 3H), 2.27 (s, 3H); MS: 581 [M+H]$^+$.

Example 137: Preparation of (E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(diethylamino)but-2-en-1-one

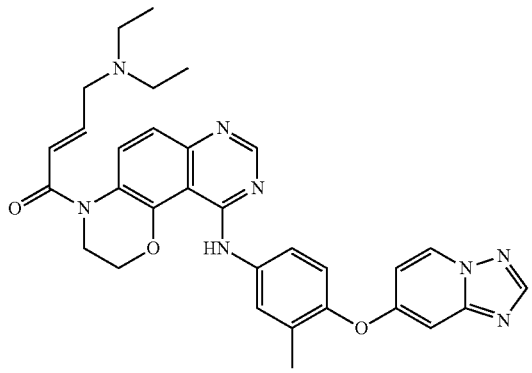 [SMILES: CCN(CC)C/C=C/C(=O)N1CCOc2c1ccc1ncnc(Nc3ccc(Oc4ccn5ncnc5c4)c(C)c3)c21]

It was prepared by a method similar to that of Example 132, except that 1-methylpiperazine was replaced by the same molar equivalent of diethylamine. $^1$H NMR (400 MHz, MeOH-d$_4$) δ 8.76 (dd, J=7.5, 0.7 Hz, 1H), 8.48 (s, 1H), 8.31 (s, 1H), 7.84-7.80 (m, 2H), 7.78 (d, J=2.7 Hz, 1H), 7.38 (d, J=9.1 Hz, 1H), 7.21 (d, J=8.5 Hz, 1H), 7.12-7.10 (m, 1H), 7.10-7.08 (m, 1H), 7.07-7.01 (m, 1H), 6.84 (dd, J=2.7, 0.7 Hz, 1H), 6.70 (d, J=15.3 Hz, 1H), 4.77 (t, J=4.7 Hz, 2H), 4.19 (d, J=4.7 Hz, 2H), 3.41-3.39 (m, 2H), 2.67-2.63 (m, 4H), 2.27 (s, 3H), 1.12 (t, J=7.1 Hz, 6H); MS: 565 [M+H]$^+$.

Assay Example 1

The assay for the inhibition of EGFR and HER2 kinase activity by small molecular compounds was carried out using the method as follows:

1) Dilution of the compounds

In a 96-well plate a, the compounds were diluted with DMSO using a 3-fold gradient dilution to form 11 concentrations, the 12th concentration is pure DMSO (as a positive control); and in a new 96-well plate b the above solutions were diluted 25 times with ultrapure water (DMSO concentration is 4%).

2) Transferring the compounds to 384-well plate

The compound solutions diluted with ultrapure water in the 96-well plate b above was transferred to the corresponding wells of a 384-well plate in duplicate.

3) Addition of 4×kinase solution: 2.5 µl of the above 4× kinase solution was taken using multichannel pipette and added to the corresponding reaction wells of the 384-well plate, mixed well and pre-reacted at room temperature for 5 minutes.

4) Addition of 2×substrate/ATP mixed solution: 5 µl of the above 2×substrate/ATP mixed solution was taken using multichannel pipette and added to the corresponding reaction wells of the 384-well plate.

5) Negative control: negative control wells were set in the 384-well plate, and 2.5 µl 4×substrate, 2.5 µl 4×enzyme solution, 2.5 µl 1×Kinase Assay Buffer and 2.5 µl ultrapure water containing 4% DMSO were added to each well.

6) Mixed by centrifugation and kept at room temperature for 2 hours in the dark.

7) Termination of the enzymatic reaction:

5 µl of the above 4× stop solution was pipetted to the corresponding wells of the 384-well plate, centrifuged and mixed, and reacted at room temperature for 5 minutes.

8) Development reaction:

5 µl of the above 4× detection solution was pipetted into the corresponding wells of the 384-well plate, centrifuged and mixed, and reacted at room temperature for 1 hour.

9) The 384-well plate was placed into a microplate reader and the signal was detected using the corresponding program.

10) IC$_{50}$ analysis:

Well reading value=10000*EU665 value/EU615 value

Inhibition rate=(reading value of positive control well−reading value of experimental well)/(reading value of positive control well−reading value of negative control well)*100%

Corresponding IC$_{50}$s can be calculated by entering the drug concentrations and the corresponding inhibition rates into GraphPad Prism 5.

Conditions of experiment for screening EGFR kinase inhibitory molecules:

The final concentration of EGFR kinase in the reaction system is 0.35 nM, and the final concentration of ATP is 150 µM, the final concentration of substrate ULight™-labeled JAK-1 (Tyr1023) Peptide is 100 nM, and the enzymatic reaction time is 2 hours.

The maximum final concentration of the compound in the reaction system is 2.5 µM, 11 concentrations were made with a 3-fold gradient dilution, and the minimal final concentration is 0.042 nM. The final concentration of DMSO is 1%.

Conditions of experiment for screening HER2 kinase inhibitory molecules:

The final concentration of HER2 kinase in the reaction system is 10 nM, the final concentration of ATP is 10 µM, the final concentration of substrate ULight™-labeled PolyGT is 100 nM, and the enzymatic reaction time is 2 hours.

The maximum final concentration of the compound in the reaction system is 2.5 µM, 11 concentrations were made with a 3-fold gradient dilution, and the minimal final concentration is 0.042 nM. The final concentration of DMSO is 1%.

Assay results of the inhibitory activity of some compounds disclosed herein on tyrosine kinases were listed in Table (1), wherein A means IC$_{50}$ is less than or equal to 50 nM, B means IC$_{50}$ is greater than 50 nM but less than or equal to 500 nM, C means IC$_{50}$ is greater than 500 nM but less than or equal to 5000 nM, D means IC$_{50}$ is greater than 5000 nM, and NT means that the compound was not tested for the corresponding kinase.

Table (1), assay results of the inhibitory activity of the compounds disclosed herein on EGFR and HER2 kinases

| Example No. | HER2 IC$_{50}$ nM | EGFR IC$_{50}$ nM |
| --- | --- | --- |
| 1 | A | NT |
| 2 | A | A |
| 3 | A | A |

| Example No. | HER2 IC$_{50}$ nM | EGFR IC$_{50}$ nM |
|---|---|---|
| 4 | A | A |
| 5 | A | NT |
| 6 | A | NT |
| 7 | A | NT |
| 8 | A | NT |
| 9 | A | NT |
| 10 | A | NT |
| 11 | A | NT |
| 12 | A | NT |
| 13 | A | NT |
| 14 | A | NT |
| 15 | A | NT |
| 16 | A | NT |
| 17 | A | NT |
| 18 | A | NT |
| 19 | A | NT |
| 20 | A | NT |
| 21 | A | NT |
| 22 | A | NT |
| 23 | A | NT |
| 24 | A | NT |
| 25 | A | NT |
| 26 | A | NT |
| 27 | A | NT |
| 28 | A | NT |
| 29 | A | NT |
| 30 | A | NT |
| 31 | B | NT |
| 32 | A | NT |
| 33 | A | A |
| 34 | A | A |
| 35 | A | A |
| 36 | A | NT |
| 37 | A | A |
| 38 | A | NT |
| 39 | A | A |
| 40 | A | A |
| 41 | A | A |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 51 | A | A |
| 52 | A | A |
| 53 | A | A |
| 54 | A | C |
| 55 | A | C |
| 56 | A | A |
| 57 | A | B |
| 58 | A | NT |
| 59 | A | A |
| 60 | A | A |
| 61 | A | A |
| 62 | A | A |
| 63 | A | B |
| 64 | A | B |
| 65 | A | A |
| 66 | A | A |
| 67 | A | A |
| 68 | A | A |
| 69 | A | A |
| 70 | A | A |
| 71 | A | A |
| 72 | A | A |
| 73 | A | B |
| 74 | A | B |
| 75 | A | B |
| 76 | A | C |
| 77 | A | C |
| 78 | A | NT |
| 79 | A | NT |
| 80 | A | NT |
| 81 | A | NT |
| 82 | A | NT |
| 83 | A | A |
| 84 | A | NT |
| 85 | A | NT |
| 86 | A | NT |
| 87 | A | NT |
| 88 | A | NT |
| 89 | A | NT |
| 90 | A | NT |
| 91 | A | A |
| 92 | A | A |
| 93 | A | A |
| 94 | A | A |
| 95 | A | A |
| 96 | A | A |
| 97 | A | NT |
| 98 | A | NT |
| 99 | A | B |
| 100 | A | NT |
| 101 | B | NT |
| 102 | A | NT |
| 103 | A | NT |
| 104 | A | A |
| 105 | A | A |
| 106 | A | A |
| 107 | A | A |
| 108 | A | A |
| 109 | A | NT |
| 110 | A | A |
| 111 | A | A |
| 112 | A | NT |
| 113 | A | NT |
| 114 | A | NT |
| 115 | A | NT |
| 116 | A | NT |
| 117 | A | NT |
| 118 | A | NT |
| 119 | A | NT |
| 120 | A | NT |
| 121 | A | NT |
| 122 | A | NT |
| 123 | A | NT |
| 124 | A | B |
| 125 | A | B |
| 126 | A | A |
| 127 | A | B |
| 128 | A | B |
| 129 | A | B |
| 130 | A | B |
| 131 | A | B |
| 132 | A | B |
| 133 | A | C |
| 134 | A | B |
| 135 | A | B |
| 136 | A | B |
| 137 | A | C |

Assay Example 2

The assay for the inhibition of cell proliferation by small molecular compounds was carried out using the method as follows:

1. 600 μL pancreatin was added to a T75 cell culture flask, which was digested in a 37° C. incubator for about 1 min before 5 mL of DMEM complete culture solution was added, blew evenly, transferred to a 15 mL centrifuge tube, and centrifuged at 1000 rpm for 4 min;

2. The supernatant was removed and 5 mL DMEM complete culture solution was added, blew evenly, and 10 μL cell suspension was taken and mixed with 10 μL 0.4% Trypan Blue, and counted using a cell counter;

3. BT474 and HCC827 cell lines were seeded in 96-well plates at a cell density of 10,000 and 3000 cells/well/80 μL, respectively, and cultured overnight. Only sterile water was added to the 36 wells on the periphery of the 96-well plate without adding cells, and only the 60 wells in the center of the 96-well plate were used for cell assays and controls;

4. Dilution of compounds: the compounds were diluted with a 3-fold dilution to make 10 concentrations in total with an initial concentration of 10 mM;

5. 20 μL of different compounds with different concentrations were added to each well, and 20 μL of complete culture solution was added to the remaining wells. The final concentration of DMSO in each well is 0.25%;

6. After 72 h of incubation, 10 μL CCK-8 reagent was added to each well, and incubated at 37° C. for 1-2 h; and the OD value was read at 450 nm;

7. Cell survival rate (%)=[(As−Ab)/(Ac−Ab)]*100%

As: Assay well (medium containing cell, CCK-8, compound)

Ac: Control well (medium containing cell, CCK-8)

Ab: Blank well (CCK-8, medium without cell and compound)

8. The value was imported into Graphpad Prism5 software for the calculation of $IC_{50}$s (compound concentration at which 50% maximum survival rate is observed).

Table (2) lists the assay results of representative compounds disclosed herein on the viability of BT474 and HCC827 cancer cells. Wherein A means $IC_{50}$ is less than or equal to 50 nM, B means $IC_{50}$ is greater than 50 nM but less than or equal to 500 nM, C means $IC_{50}$ is greater than 500 nM but less than or equal to 5000 nM, D means $IC_{50}$ is greater than 5000 nM, and NT means that the compound was not tested for the corresponding cell.

TABLE 2

Assay results of representative compounds disclosed herein on cell viability

| Example No. | BT474 $IC_{50}$ | HCC827 $IC_{50}$ |
|---|---|---|
| 44 | A | C |
| 46 | A | B |
| 47 | A | C |
| 48 | B | C |
| 49 | A | B |
| 50 | A | C |
| 51 | A | C |
| 53 | A | C |
| 54 | A | C |
| 55 | A | C |
| 56 | A | C |
| 57 | A | C |
| 58 | A | B |
| 59 | A | C |
| 60 | A | C |
| 61 | A | D |
| 62 | B | D |
| 63 | A | C |
| 64 | A | B |
| 65 | A | B |
| 66 | A | C |
| 68 | A | C |
| 69 | A | C |
| 70 | A | NT |
| 71 | A | C |
| 72 | A | B |
| 73 | A | C |
| 74 | A | C |
| 76 | A | B |
| 78 | A | C |
| 79 | A | C |
| 80 | A | C |
| 81 | A | C |
| 82 | A | C |
| 83 | A | C |

TABLE 2-continued

Assay results of representative compounds disclosed herein on cell viability

| Example No. | BT474 $IC_{50}$ | HCC827 $IC_{50}$ |
|---|---|---|
| 84 | A | B |
| 85 | A | C |
| 86 | A | C |
| 87 | B | C |
| 88 | A | C |
| 89 | A | C |
| 90 | A | C |
| 91 | A | C |
| 92 | A | C |
| 93 | A | B |
| 94 | A | C |
| 95 | A | B |
| 96 | A | B |
| 100 | A | B |
| 101 | NT | C |
| 102 | A | B |
| 103 | A | B |
| 104 | A | B |
| 105 | A | B |
| 106 | A | B |
| 107 | A | C |
| 108 | A | B |
| 109 | A | B |
| 110 | A | B |
| 111 | A | C |
| 112 | A | B |
| 113 | B | C |
| 114 | A | NT |
| 115 | A | NT |
| 116 | A | B |
| 117 | A | NT |
| 118 | A | NT |
| 119 | A | B |
| 120 | A | NT |
| 121 | A | NT |
| 122 | A | NT |
| 123 | A | NT |
| 124 | A | NT |
| 125 | A | NT |
| 126 | A | NT |
| 127 | A | NT |
| 128 | A | NT |
| 129 | A | NT |
| 130 | A | NT |
| 131 | A | NT |
| 132 | A | NT |
| 133 | A | NT |
| 134 | A | NT |
| 135 | A | NT |
| 136 | A | NT |
| 137 | A | NT |

The biological data provided by the present disclosure indicates that the compounds of the present disclosure have extremely strong inhibitory ability on HER2 kinase and HER2 expressing cells, which are beneficial to the treatment or prevention of diseases caused by abnormality of HER2 kinase. Another feature of the compound of the present disclosure is that its ability to inhibit cells with EGFR expression is relatively weak, thereby greatly reducing side effects caused by excessive inhibition of EGFR.

The above is a preferred embodiment of the present disclosure, and it should be noted that those skilled in the art can make various improvements and modifications to the embodiments of the present disclosure without departing from the principles of the present disclosure. These improvements and modifications are also considered to be within the scope of the disclosure.

The invention claimed is:
1. A compound of Formula (I), or a diastereomer, enantiomer, hydrate, solvate, or pharmaceutically acceptable salt thereof:

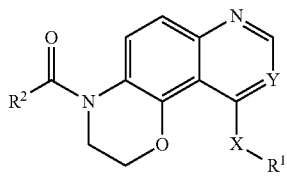

Formula (I)

in the formula (I),
X is O, or NH;
Y is N or C—Z, wherein Z is —H or —CN;
$R^1$ is

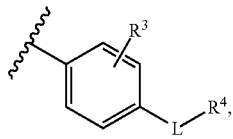

$R^3$ is —H, halogen, $C_1$-$C_3$ alkyl, $C_1$-$C_3$ alkoxy, $C_1$-$C_3$ alkyl substituted by halogen, or $C_1$-$C_3$ alkoxy substituted by halogen;
L is

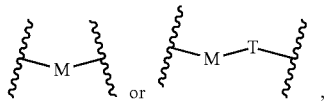

M is O or S;
T is linear $C_1$-$C_3$ alkylene, or linear $C_1$-$C_3$ alkylene independently substituted by $R^5$ and $R^6$, respectively;
$R^5$ and $R^6$ are independently —H, halogen, $C_1$-$C_3$ alkyl, or $C_1$-$C_3$ alkyl substituted by halogen;
$R^4$ is aryl, 5- to 6-membered heteroaryl, aryl substituted by 1-3 identical or different $R^7$, or 5- to 6-membered heteroaryl substituted by 1-3 identical or different $R^7$, wherein the heteroaryl group is a heteroaryl group containing 1-3 heteroatoms selected from N, O or S;
$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl;
$R^2$ is

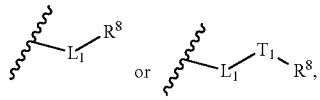

$L_1$ is selected from:

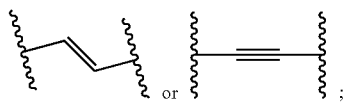

$T_1$ is linear $C_1$-$C_8$ alkylene, linear $C_1$-$C_8$ alkylene independently substituted by $R^9$ and $R^{10}$, respectively;
$R^9$ and $R^{10}$ are each independently —H, or $C_1$-$C_3$ alkyl;
$R^8$ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —$NR^{11}R^{12}$;
$R^{11}$ and $R^{12}$ are each independently —H, $C_1$-$C_6$ alkyl, $C_3$-$C_6$ cycloalkyl, $C_1$-$C_6$ alkyl substituted by hydroxy, or $C_1$-$C_6$ alkyl substituted by $C_1$-$C_3$ alkoxy;
the 4- to 7-membered heterocyclyl is a heterocyclyl containing 1-2 heteroatoms selected from N, O or S, the heterocyclyl is unsubstituted or substituted by one or two of the group consisting of: $C_1$-$C_3$ alkyl, aldehyde group, $C_1$-$C_4$ alkylacyl, aminoacyl, aminoacyl wherein the amino is substituted with mono- or di-$C_1$-$C_3$ alkyl, $C_1$-$C_3$ alkylsulfonyl, and $C_1$-$C_3$ alkylsulfinyl, or the sulfur in the heterocycle is oxidized by one to two oxygen atoms.

2. The compound, or a diastereomer, enantiomer, hydrate, solvate, or pharmaceutically acceptable salt thereof according to claim 1, wherein:
$R^1$ is

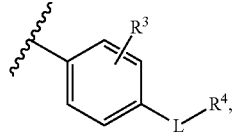

$R^3$ is —H, fluorine, chlorine, bromine, methyl, ethyl, methoxy, ethoxy, trifluoromethyl or trifluoromethoxy;
L is

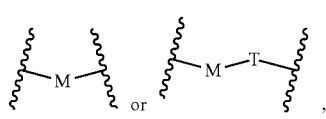

M is O or S,
T is linear $C_1$-$C_2$ alkylene, or linear $C_1$-$C_2$ alkylene independently substituted by $R^5$ and $R^6$, respectively;
$R^5$ and $R^6$ are independently —H, —F, methyl, ethyl or trifluoromethyl;
$R^4$ is aryl, 5- to 6-membered heteroaryl, aryl substituted by 1-2 identical or different $R^7$, or 5- to 6-membered heteroaryl substituted by 1-2 identical or different $R^7$, wherein the aryl or heteroaryl group is selected from the group consisting of: phenyl, pyridyl, pyrimidinyl, thiazolyl, thienyl, pyrrolyl, thiadiazolyl, furyl, oxazolyl or isoxazolyl;
$R^7$ is —H, —F, —Cl, —Br, —$CF_3$, —$OCF_3$, amino, hydroxy, cyano, methylthio, ethylthio, propylthio, isopropylthio, methylamino, ethylamino, dimethylamino, diethyl amino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methylaminoethoxy, methylaminopropoxy, ethylaminoethoxy, ethylaminopropoxy, dimethylaminoethoxy, dimethylaminopropoxy, diethylaminoethoxy, or diethylaminopropoxy.

3. The compound, or a diastereomer, enantiomer, hydrate, solvate, or pharmaceutically acceptable salt thereof according to claim 1, wherein:

$R^2$ is

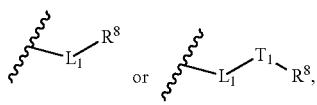

$L_1$ is selected from:

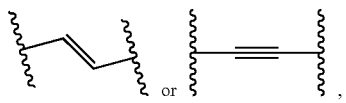

$T_1$ is linear $C_1$-$C_6$ alkylene, or linear $C_1$-$C_6$ alkylene independently substituted by $R^9$ and $R^{10}$, respectively;

$R^9$ and $R^{10}$ are independently —H or methyl;

$R^8$ is —H, hydroxy, methyl, ethyl, propyl, isopropyl, cyclopropyl, cyclobutyl, cyclopentyl, cyclohexyl, methoxy, ethoxy, propoxy, isopropoxy, methylthio, ethylthio, propylthio, isopropylthio, 5- to 6-membered heterocyclyl or —NR$^{11}$R$^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, cyclohexyl, hydroxyethyl, hydroxypropyl, hydroxybutyl, hydroxypentyl, hydroxyhexyl, methoxyethyl, methoxypropyl, methoxybutyl, methoxypentyl, methoxyhexyl, ethoxyethyl, ethoxypropyl, ethoxybutyl, ethoxypentyl, ethoxyhexyl, propoxyethyl, propoxypropyl, propoxybutyl, propoxypentyl, propoxyhexyl, isopropoxyethyl, isopropoxypropyl, isopropoxybutyl, isopropoxypentyl or isopropoxyhexyl;

the 5- to 6-membered heterocyclyl is a heterocyclyl containing 1-2 heteroatoms selected from N, O or S, the 5- to 6-membered heterocyclyl is unsubstituted or substituted by one or two of the group consisting of: methyl, ethyl, propyl, isopropyl, formyl, acetyl, propionyl, butyryl, isobutyryl, aminoacyl, methyl aminoacyl, dimethylaminoacyl, methylsulfonyl, ethyl sulfonyl, isopropylsulfonyl, methylsulfinyl, ethylsulfinyl, or isopropylsulfinyl, or sulfur in the heterocycle is oxidized by one to two oxygen atoms.

4. The compound, or a diastereomer, enantiomer, hydrate, solvate, or pharmaceutically acceptable salt thereof according to claim 3, wherein the 5- to 6-membered heterocyclyl is derived from the 5- to 6-membered heterocycle selected from the following:

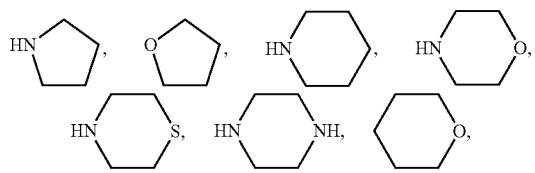

and the 5- to 6-membered heterocyclyl is unsubstituted or substituted by one or two of the group consisting of: methyl, ethyl, propyl, isopropyl, formyl, acetyl, propionyl, butyryl, isobutyryl, aminoacyl, methylaminoacyl, dimethylaminoacyl, methyl sulfonyl, ethyl sulfonyl, isopropylsulfonyl, methylsulfinyl, ethylsulfinyl, or isopropylsulfinyl, or sulfur in the heterocycle is oxidized by one to two oxygen atoms.

5. The compound, or a diastereomer, enantiomer, hydrate, solvate, or pharmaceutically acceptable salt thereof according to claim 1, wherein:

$R^2$ is

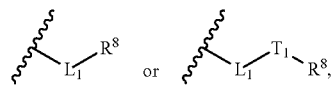

$L_1$ is selected from:

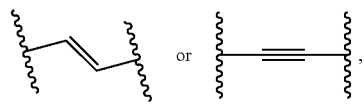

$T_1$ is linear $C_1$-$C_6$ alkylene, or linear $C_1$-$C_6$ alkylene independently substituted by $R^9$ and $R^{10}$, respectively;

$R^9$ and $R^{10}$ are each independently —H or methyl;

$R^8$ is —H, hydroxy, methyl, ethyl, propyl, isopropyl, methoxy, ethoxy, propoxy, isopropoxy, methylthio, ethylthio, propylthio, isopropylthio, cyclopropyl, cyclobutyl, cyclopentyl, cyclohexyl, 5- to 6-membered heterocyclyl or —NR$^{11}$R$^{12}$, $R^{11}$ and $R^{12}$ are each independently —H, methyl, ethyl, propyl, butyl, pentyl, hexyl, isopropyl, sec-butyl, 1-ethylpropyl, cyclopropyl, cyclobutyl, cyclopentyl, hydroxyethyl, hydroxypropyl, hydroxybutyl, hydroxypentyl, methoxyethyl, methoxypropyl, methoxybutyl, methoxypentyl, ethoxyethyl, ethoxypropyl, ethoxybutyl, ethoxypentyl, propoxyethyl, propoxypropyl, propoxybutyl, propoxypentyl, isopropoxyethyl, isopropoxypropyl, isopropoxybutyl or isopropoxypentyl;

the 5- to 6-membered heterocyclyl is selected from:

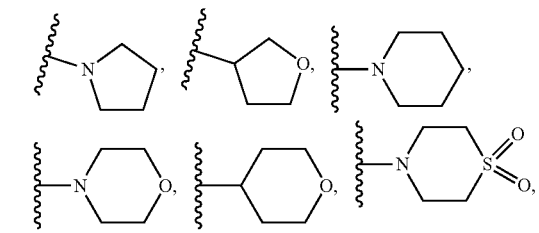

R¹³ is —H, methyl, ethyl, propyl, or isopropyl.

6. The compound, or a diastereomer, enantiomer, hydrate, solvate, or pharmaceutically acceptable salt thereof according to claim 1, wherein:
in the formula (I),
X is NH;
Y is N;
R¹ is R³ is —H, halogen, C₁-C₃ alkyl, or C₁-C₃ alkyl substituted by halogen;
L is M is O or S;
T is linear C₁-C₃ alkylene;
R⁴ is aryl, 5- to 6-membered heteroaryl, or aryl substituted by 1-3 identical or different R⁷, wherein the heteroaryl group is a heteroaryl group containing 1-3 heteroatoms selected from N, O or S;
R⁷ is —H, or halogen;
R² is L₁ is selected from:

T₁ is linear C₁-C₈ alkylene;
R⁸ is —NR¹¹R¹²;
R¹¹ and R¹² are each independently —H, C₁-C₆ alkyl, or C₃-C₆ cycloalkyl.

7. The compound of Formula (I) according to claim 1, a pharmaceutically acceptable salt, diastereomer, enantiomer, hydrate, or solvate thereof, wherein the pharmaceutically acceptable salt is selected from one or more of the following salts of the said compound: hydrochloride, hydrobromide, hydroiodide, perchlorate, sulfate, nitrate, phosphate, formate, acetate, propionate, glycolate, lactate, succinate, maleate, tartrate, malate, citrate, fumarate, gluconate, benzoate, mandelate, methanesulfonate, isethionate, benzenesulfonate, oxalate, palmitate, 2-naphthalenesulfonate, p-toluenesulfonate, cyclohexylsulfamate, salicylate, hexonate, trifluoroacetate, aluminum salt, calcium salt, chloroprocaine salt, choline salt, diethanolamine salt, ethylenediamine salt, lithium salt, magnesium salt, potassium salt, sodium salt and zinc salt.

8. The compound, or a diastereomer, enantiomer, hydrate, solvate, or pharmaceutically acceptable salt thereof according to claim 1, wherein the compound is selected from the group consisting of:
1-(10-((4-(3-(trifluoromethyl)phenoxy)phenyl)amino)-2,3-dihydro-4H-[1,4]oxazino[2,3-f]quinazolin-4-yl)prop-2-en-1-one;
1-(10-((4-phenoxyphenyl)amino)-2,3-dihydro-4H-[1,4]oxazino[2,3-f]quinazolin-4-yl)prop-2-en-1-one;
1-(10-((3-chloro-4-((3-fluorobenzyloxy)phenyl)amino)-2,3-dihydro-4H-[1,4]oxazino[2,3-f]quinazolin-4-yl)prop-2-en-1-one;
1-(10-((3-chloro-4-(pyridin-2-ylmethoxy)phenyl)amino)-2,3-dihydro-4H-[1,4]oxazino[2,3-f]quinazolin-4-yl)prop-2-en-1-one;
1-(10-((4-(m-tolyloxy)phenyl)amino)-2,3-dihydro-4H-[1,4]oxazino[2,3-f]quinazolin-4-yl)prop-2-en-1-one;
1-(10-((4-(3-chlorophenoxy)phenyl)amino)-2,3-dihydro-4H-[1,4]oxazino[2,3-f]quinazolin-4-yl)prop-2-en-1-one;
1-(10-((4-(3-fluorophenoxy)phenyl)amino)-2,3-dihydro-4H-[1,4]oxazino[2,3-f]quinazolin-4-yl)prop-2-en-1-one;
1-(10-((4-(2-fluorophenoxy)phenyl)amino)-2,3-dihydro-4H-[1,4]oxazino[2,3-f]quinazolin-4-yl)prop-2-en-1-one;
1-(10-((4-(4-fluorophenoxy)phenyl)amino)-2,3-dihydro-4H-[1,4]oxazino[2,3-f]quinazolin-4-yl)prop-2-en-1-one;
1-(10-((4-(4-chlorophenoxy)phenyl)amino)-2,3-dihydro-4H-[1,4]oxazino[2,3-f]quinazolin-4-yl)prop-2-en-1-one;
1-(10-((4-(2-methoxyphenoxy)phenyl)amino)-2,3-dihydro-4H-[1,4]oxazino[2,3-f]quinazolin-4-yl)prop-2-en-1-one;
1-(10-((4-(pyridin-2-yloxy)phenyl)amino)-2,3-dihydro-4H-[1,4]oxazino[2,3-f]quinazolin-4-yl)prop-2-en-1-one;
1-(10-((4-(pyridin-3-yloxy)phenyl)amino)-2,3-dihydro-4H-[1,4]oxazino[2,3-f]quinazolin-4-yl)prop-2-en-1-one;
1-(10-((4-(3-methoxyphenoxy)phenyl)amino)-2,3-dihydro-4H-[1,4]oxazino[2,3-f]quinazolin-4-yl)prop-2-en-1-one;
1-(10-((4-(thiazol-2-yloxy)phenyl)amino)-2,3-dihydro-4H-[1,4]oxazino[2,3-f]quinazolin-4-yl)prop-2-en-1-one;
1-(10-((3-fluoro-4-phenoxyphenyl)amino)-2,3-dihydro-4H-[1,4]oxazino[2,3-f]quinazolin-4-yl)prop-2-en-1-one;
1-(10-((3-chloro-4-phenoxyphenyl)amino)-2,3-dihydro-4H-[1,4]oxazino[2,3-f]quinazolin-4-yl)prop-2-en-1-one;

1-(10-((4-((4-fluorobenzyl)oxy)phenyl)amino)-2,3-dihydro-4H-[1,4]oxazino[2,3-f]quinazolin-4-yl)prop-2-en-1-one;
1-(10-((4-((3-fluorobenzyl)oxy)phenyl)amino)-2,3-dihydro-4H-[1,4]oxazino[2,3-f]quinazolin-4-yl)prop-2-en-1-one;
1-(10-((4-((3-trifluoromethylbenzyl)oxy)phenyl)amino)-2,3-dihydro-4H-[1,4]oxazino[2,3-f]quinazolin-4-yl)prop-2-en-1-one;
1-(10-((4-(pyridin-2-ylmethoxy)phenyl)amino)-2,3-dihydro-4H-[1,4]oxazino[2,3-f]quinazolin-4-yl)prop-2-en-1-one;
1-(10-((4-(thiophen-2-ylmethoxy)phenyl)amino)-2,3-dihydro-4H-[1,4]oxazino[2,3-f]quinazolin-4-yl)prop-2-en-1-one;
1-(10-((4-(thiazol-2-ylmethoxy)phenyl)amino)-2,3-dihydro-4H-[1,4]oxazino[2,3-f]quinazolin-4-yl)prop-2-en-1-one;
1-(10-((4-(benzylthio)phenyl)amino)-2,3-dihydro-4H-[1,4]oxazino[2,3-f]quinazolin-4-yl)prop-2-en-1-one;
1-(10-((4-((3-fluorobenzyl)oxy)-3-(trifluoromethyl)phenyl)amino)-2,3-dihydro-4H-[1,4]oxazino[2,3-f]quinazolin-4-yl)prop-2-en-1-one;
1-(10-((4-((3-fluorobenzyl)oxy)-3-(methoxy)phenyl)amino)-2,3-dihydro-4H-[1,4]oxazino[2,3-f]quinazolin-4-yl)prop-2-en-1-one;
1-(10-((4-((3-fluorobenzyl)oxy)-3-fluorophenyl)amino)-2,3-dihydro-4H-[1,4]oxazino[2,3-f]quinazolin-4-yl)prop-2-en-1-one;
1-(10-((4-((4-fluorophenyl)thio)phenyl)amino)-2,3-dihydro-4H-[1,4]oxazino[2,3-f]quinazolin-4-yl)prop-2-en-1-one;
1-(10-((2-fluoro-4-phenoxyphenyl)amino)-2,3-dihydro-4H-[1,4]oxazino[2,3-f]quinazolin-4-yl)prop-2-en-1-one;
1-(10-((4-(2-(2-(dimethylamino)ethoxy)phenoxy)phenyl)amino)-2,3-dihydro-4H-[1,4]oxazino[2,3-f]quinazolin-4-yl)prop-2-en-1-one;
1-(10-((4-(2-(3-(dimethylamino)propoxy)phenoxy)phenyl)amino)-2,3-dihydro-4H-[1,4]oxazino[2,3-f]quinazolin-4-yl)prop-2-en-1-one;
1-(10-((4-(2-(2-methoxyethoxy)phenoxy)phenyl)amino)-2,3-dihydro-4H-[1,4]oxazino[2,3-f]quinazolin-4-yl)prop-2-en-1-one;
1-(10-(4-phenoxyphenoxy)-2,3-dihydro-4H-[1,4]oxazino[2,3-f]quinazolin-4-yl)prop-2-en-1-one;
1-(10-(3-chloro-4-(pyridin-2-ylmethoxy)phenoxy)-2,3-dihydro-4H-[1,4]oxazino[2,3-f]quinazolin-4-yl)prop-2-en-1-one;
1-(10-(3-chloro-4-((3-fluorobenzyl)oxy)phenoxy)-2,3-dihydro-4H-[1,4]oxazino[2,3-f]quinazolin-4-yl)prop-2-en-1-one;
1-(10-(4-(4-chlorophenoxy)phenoxy)-2,3-dihydro-4H-[1,4]oxazino[2,3-f]quinazolin-4-yl)prop-2-en-1-one;
1-(10-(4-(4-fluorophenoxy)phenoxy)-2,3-dihydro-4H-[1,4]oxazino[2,3-f]quinazolin-4-yl)prop-2-en-1-one;
1-(10-(4-(2,5-dichlorophenoxy)phenoxy)-2,3-dihydro-4H-[1,4]oxazino[2,3-f]quinazolin-4-yl)prop-2-en-1-one;
1-(10-(4-(pyridin-2-ylmethoxy)phenoxy)-2,3-dihydro-4H-[1,4]oxazino[2,3-f]quinazolin-4-yl)prop-2-en-1-one;
1-(10-(4-((2-fluorobenzyl)oxy)phenoxy)-2,3-dihydro-4H-[1,4]oxazino[2,3-f]quinazolin-4-yl)prop-2-en-1-one;
1-(10-(4-((3-fluorobenzyl)oxy)phenoxy)-2,3-dihydro-4H-[1,4]oxazino[2,3-f]quinazolin-4-yl)prop-2-en-1-one;
1-(10-(4-((4-fluorobenzyl)oxy)phenoxy)-2,3-dihydro-4H-[1,4]oxazino[2,3-f]quinazolin-4-yl)prop-2-en-1-one;
(E)-4-(dimethylamino)-1-(10-((4-(3-(trifluoromethyl)phenoxy)phenyl)amino)-2,3-dihydro-4H-[1,4]oxazino[2,3-f]quinazolin-4-yl)but-2-en-1-one;
(E)-4-(dimethylamino)-1-(10-((4-phenoxyphenyl)amino)-2,3-dihydro-4H-[1,4]oxazino[2,3-f]quinazolin-4-yl)but-2-en-1-one;
(E)-1-(10-((3-chloro-4-((3-fluorobenzyl)oxy)phenyl)amino)-2,3-dihydro-4H-[1,4]oxazino[2,3-f]quinazolin-4-yl)-4-(dimethylamino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(dimethylamino)but-2-en-1-one;
(E)-4-(dimethylamino)-1-(10-((4-(m-tolyloxy)phenyl)amino)-2,3-dihydro-4H-[1,4]oxazino[2,3-f]quinazolin-4-yl)but-2-en-1-one;
(E)-4-(dimethylamino)-1-(10-((4-(3-chlorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(3-fluorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(2-fluorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(4-fluorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(4-chlorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(2-methoxyphenoxy)phenyl)amino)-2,3-dihydro-4H-[1,4]oxazino[2,3-f]quinazolin-4-yl)but-2-en-1-one;
(E)-4-(dimethylamino)-1-(10-((4-(pyridin-2-yloxy)phenyl)amino)-2,3-dihydro-4H-[1,4]oxazino[2,3-f]quinazolin-4-yl)but-2-en-1-one;
(E)-4-(dimethylamino)-1-(10-((4-(pyridin-3-yloxy)phenyl)amino)-2,3-dihydro-4H-[1,4]oxazino[2,3-f]quinazolin-4-yl)but-2-en-1-one;
(E)-4-(dimethylamino)-1-(10-((4-(3-methoxyphenoxy)phenyl)amino)-2,3-dihydro-4H-[1,4]oxazino[2,3-f]quinazolin-4-yl)but-2-en-1-one;
(E)-4-(dimethylamino)-1-(10-((4-(thiazol-2-yloxy)phenyl)amino)-2,3-dihydro-4H-[1,4]oxazino[2,3-f]quinazolin-4-yl)but-2-en-1-one;
(E)-4-(dimethylamino)-1-(10-((3-fluoro-4-phenoxyphenyl)amino)-2,3-dihydro-4H-[1,4]oxazino[2,3-f]quinazolin-4-yl)but-2-en-1-one;
(E)-4-(dimethylamino)-1-(10-((3-chloro-4-phenoxyphenyl)amino)-2,3-dihydro-4H-[1,4]oxazino[2,3-f]quinazolin-4-yl)but-2-en-1-one;
(E)-4-(dimethylamino)-1-(10-((4-((4-fluorobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((3-fluorobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((3-(trifluoromethylbenzyl)oxy)phenyl)amino)-2,3-dihydro-4H-[1,4]oxazino[2,3-f]quinazolin-4-yl)but-2-en-1-one;

(E)-4-(dimethylamino)-1-(10-((4-(pyridin-2-ylmethoxy)phenyl)amino)-2,3-dihydro-4H-[1,4]oxazino[2,3-f]quinazolin-4-yl)but-2-en-1-one;
(E)-4-(dimethylamino)-1-(10-((4-(thiophen-2-ylmethoxy)phenyl)amino)-2,3-dihydro-4H-[1,4]oxazino[2,3-f]quinazolin-4-yl)but-2-en-1-one;
(E)-4-(dimethylamino)-1-(10-((4-(thiazol-2-ylmethoxy)phenyl)amino)-2,3-dihydro-4H-[1,4]oxazino[2,3-f]quinazolin-4-yl)but-2-en-1-one;
(E)-4-(dimethylamino)-1-(10-((4-(benzylthio)phenyl)amino)-2,3-dihydro-4H-[1,4]oxazino[2,3-f]quinazolin-4-yl)but-2-en-1-one;
(E)-4-(dimethylamino)-1-(10-((4-((3-fluorobenzyl)oxy-3-(trifluoromethyl)phenyl)amino)-2,3-dihydro-4H-[1,4]oxazino[2,3-f]quinazolin-4-yl)but-2-en-1-one;
(E)-4-(dimethylamino)-1-(10-((4-((3-fluorobenzyl)oxy)-3-methoxyphenyl)amino)-2,3-dihydro-4H-[1,4]oxazino[2,3-f]quinazolin-4-yl)but-2-en-1-one;
(E)-4-(dimethylamino)-1-(10-((4-((3-fluorobenzyl)oxy)-3-fluorophenyl)amino)-2,3-dihydro-4H-[1,4]oxazino[2,3-f]quinazolin-4-yl)but-2-en-1-one;
(E)-4-(dimethylamino)-1-(10-((4-((4-fluorophenyl)thio)phenyl)amino)-2,3-dihydro-4H-[1,4]oxazino[2,3-f]quinazolin-4-yl)but-2-en-1-one;
(E)-4-(dimethylamino)-1-(10-((4-(2-fluoro-5-methylphenoxy)phenyl)amino)-2,3-dihydro-4H-[1,4]oxazino[2,3-f]quinazolin-4-yl)but-2-en-1-one;
(E)-4-(dimethylamino)-1-(10-((4-(5-chloro-2-fluorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(2,5-difluorophenoxy)phenyl)amino)-2,3-dihydro-4H-[1,4]oxazino[2,3-f]quinazolin-4-yl)but-2-en-1-one;
(E)-4-(dimethylamino)-1-(10-((4-(1-(3-fluorophenyl)ethoxy)phenyl)amino)-2,3-dihydro-4H-[1,4]oxazino[2,3-f]quinazolin-4-yl)but-2-en-1-one;
(E)-4-(dimethylamino)-1-(10-((4-(1-(pyridin-2-yl)ethoxy)phenyl)amino)-2,3-dihydro-4H-[1,4]oxazino[2,3-f]quinazolin-4-yl)but-2-en-1-one;
(E)-4-(dimethylamino)-1-(10-((4-(pyridin-3-ylmethoxy)phenyl)amino)-2,3-dihydro-4H-[1,4]oxazino[2,3-f]quinazolin-4-yl)but-2-en-1-one;
(E)-4-(dimethylamino)-1-(10-((4-(pyridin-4-ylmethoxy)phenyl)amino)-2,3-dihydro-4H-[1,4]oxazino[2,3-f]quinazolin-4-yl)but-2-en-1-one;
(E)-1-(10-((4-(benzyloxy)phenyl)amino)-2,3-dihydro-4H-[1,4]oxazino[2,3-f]quinazolin-4-yl)-4-(dimethylamino)but-2-en-1-one;
(E)-4-(dimethylamino)-1-(10-((4-((2-fluorobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((2-chlorobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((2-methylbenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((2-methoxybenzyl)oxy)phenyl)amino)-2,3-dihydro-4H-[1,4]oxazino[2,3-f]quinazolin-4-yl)but-2-en-1-one;
(E)-1-(10-((4-((3-chlorobenzyl)oxy)phenyl)amino)-2,3-dihydro-4H-[1,4]oxazino[2,3-f]quinazolin-4-yl)-4-(dimethylamino)but-2-en-1-one;
(E)-1-(10-((4-((3-methylbenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((3-cyanobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((3-methoxybenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((4-chlorobenzyl)oxy)phenyl)amino)-2,3-dihydro-4H-[1,4]oxazino[2,3-f]quinazolin-4-yl)but-2-en-1-one;
(E)-4-(dimethylamino)-1-(10-((4-((4-methylbenzyl)oxy)phenyl)amino)-2,3-dihydro-4H-[1,4]oxazino[2,3-f]quinazolin-4-yl)but-2-en-1-one;
(E)-1-(10-((4-(2,5-difluorobenzyl)oxy)phenyl)amino)-2,3-dihydro-4H-[1,4]oxazino[2,3-f]quinazolin-4-yl)-4-(dimethylamino)but-2-en-1-one;
(E)-1-(10-((4-((2-chloro-5-fluorobenzyl)oxy)phenyl)amino)-2,3-dihydro-4H-[1,4]oxazino[2,3-f]quinazolin-4-yl)-4-(dimethylamino)but-2-en-1-one;
(E)-1-(10-((4-phenoxyphenyl)amino)-2,3-dihydro-4H-[1,4]oxazino[2,3-f]quinazolin-4-yl)-4-(pyrrolidin-1-yl)but-2-en-1-one;
(E)-4-(diethylamino)-1-(10-((4-phenoxyphenyl)amino)-2,3-dihydro-4H-[1,4]oxazino[2,3-f]quinazolin-4-yl)but-2-en-1-one;
(E)-1-(10-((4-phenoxyphenyl)amino)-2,3-dihydro-4H-[1,4]oxazino[2,3-f]quinazolin-4-yl)-4-(piperidin-1-yl)but-2-en-1-one;
(E)-4-morpholino-1-(10-((4-phenoxyphenyl)amino)-2,3-dihydro-4H-[1,4]oxazino[2,3-f]quinazolin-4-yl)but-2-en-1-one;
(E)-4-(4-methylpiperazin-1-yl)-1-(10-((4-phenoxyphenyl)amino)-2,3-dihydro-4H-[1,4]oxazino[2,3-f]quinazolin-4-yl)but-2-en-1-one;
(E)-1-(10-((3-chloro-4-((3-fluorobenzyl)oxy)phenyl)amino)-2,3-dihydro-4H-[1,4]oxazino[2,3-f]quinazolin-4-yl)-4-morpholinobut-2-en-1-one;
(E)-1-(10-((2-fluoro-4-phenoxyphenyl)amino)-2,3-dihydro-4H-[1,4]oxazino[2,3-f]quinazolin-4-yl)-4-(piperidin-1-yl)but-2-en-1-one;
(E)-1-(10-((3-fluoro-4-phenoxyphenyl)amino)-2,3-dihydro-4H-[1,4]oxazino[2,3-f]quinazolin-4-yl)-4-(piperidin-1-yl)but-2-en-1-one;
(E)-1-(10-((4-(2-fluorophenoxy)phenyl)amino)-2,3-dihydro-4H-[1,4]oxazino[2,3-f]quinazolin-4-yl)-4-((4-methoxybutyl)amino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(cyclopropyl(methyl)amino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(cyclopropylamino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(isopropylamino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-morpholinobut-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(4-methylpiperazin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(diethylamino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(pyrrolidin-1-yl)but-2-en-1-one;

(E)-1-(10-((3-chloro-4-(pyridin-2-ylmethoxy)phenyl)amino)-2,3-dihydro-4H-[1,4]oxazino[2,3-f]quinazolin-4-yl)-4-(piperidin-1-yl)but-2-en-1-one;
(E)-4-(4-acetylpiperazin-1-yl)-1-(10-((3-chloro-4-(pyridin-2-ylmethoxy)phenyl)amino)-2,3-dihydro-4H-[1,4]oxazino[2,3-f]quinazolin-4-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(cyclobutylamino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(cyclobutyl(methyl)amino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(isopropyl(methyl)amino)but-2-en-1-one;
(S,E)-1-(10-((3-chloro-4-(pyridin-2-ylmethoxy)phenyl)amino)-2,3-dihydro-4H-[1,4]oxazino[2,3-f]quinazolin-4-yl)-3-(1-methylpyrrolidin-2-yl)prop-2-en-1-one;
1-(10(3-chloro-4-(pyridin-2-ylmethoxy)phenyl)amino)-2,3-dihydro-4H-[1,4]oxazino[2,3-f]quinazolin-4-yl)but-2-yne-1-one;
(R,E)-1-(10-(3-chloro-4-(pyridin-2-ylmethoxy)phenyl)amino)-2,3-dihydro-4H-[1,4]oxazino[2,3-f]quinazolin-4-yl)-3-(1-methylpyrrolidin-2-yl)prop-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(4-hydroxypiperidin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(4-hydroxyl-4-methylpiperidin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(4-(hydroxymethyl)piperidin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-(4-fluoropiperidin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-((2-methoxyethyl)(methyl)amino)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-((3-hydroxypropyl)(methyl)amino)but-2-en-1-one;
(S,E)-1-(10-((3-chloro-4-(pyridin-2-ylmethoxy)phenyl)amino)-2,3-dihydro-4H-[1,4]oxazino[2,3-f]quinazolin-4-yl)-4-(2,4-dimethylpiperazin-1-yl)but-2-en-1-one;
(E)-1-(10-((3-chloro-4-(pyridin-2-ylmethoxy)phenyl)amino)-2,3-dihydro-4H-[1,4]oxazino[2,3-f]quinazolin-4-yl)-4-((2-hydroxyethyl)(methyl)amino)but-2-en-1-one;
(R,E)-1-(10-((3-chloro-4-(pyridin-2-ylmethoxy)phenyl)amino)-2,3-dihydro-4H-[1,4]oxazino[2,3-f]quinazolin-4-yl)-4-(2,4-dimethylpiperazin-1-yl)but-2-en-1-one;
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(dimethylamino)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(dimethylamino)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(4-methylpiperazin-1-yl)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(isopropyl(methyl)amino)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(piperidin-1-yl)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(cyclobutyl(methyl)amino)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-((2-methoxyethyl)(methyl)amino)but-2-en-1-one;
(E)-1-(10-((4-([1,2,4]triazolo[1,5-a]pyridin-7-yloxy)-3-chlorophenyl)amino)-2,3-dihydro-4H-[1,4]oxazino[2,3-f]quinazolin-4-yl)-4-(diethylamino)but-2-en-1-one;
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(4-methylpiperazin-1-yl)but-2-en-1-one;
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(isopropyl(methyl)amino)but-2-en-1-one;
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(piperidin-1-yl)but-2-en-1-one;
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(cyclobutyl(methyl)amino)but-2-en-1-one;
(E)-1-(10-((4-([1,2,4]triazolo[1,5-a]pyridin-7-yloxy)-3-methylphenyl)amino)-2,3-dihydro-4H-[ 1,4]oxazino[2,3-f]quinazolin-4-yl)-4-((2-methoxyethyl)(methyl)amino)but-2-en-1-one; and
(E)-1-(10-((4-([1,2,4]triazolo[1,5-a]pyridin-7-yloxy)-3-methylphenyl)amino)-2,3-dihydro-4H-[1,4]oxazino[2,3-f]quinazolin-4-yl)-4-(diethylamino)but-2-en-1-one.

9. The compound according to claim 8 having the following structure:

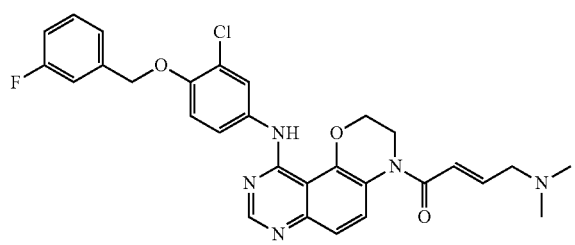 [SMILES: CN(C)C/C=C/C(=O)N1CCOc2c1ccc1ncnc(Nc3ccc(OCc4cccc(F)c4)c(Cl)c3)c21]

or the pharmaceutically acceptable salt thereof.

10. The compound according to claim 8 having the following structure:

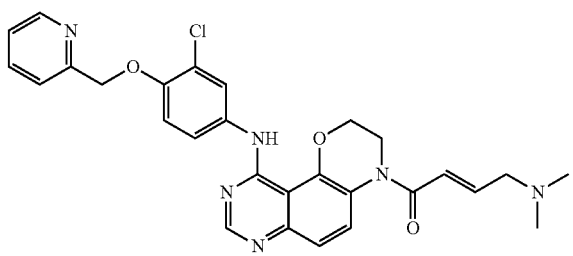 [SMILES: CN(C)C/C=C/C(=O)N1CCOc2c1ccc1ncnc(Nc3ccc(OCc4ccccn4)c(Cl)c3)c21]

or the pharmaceutically acceptable salt thereof.

11. The compound according to claim 8 having the following structure:

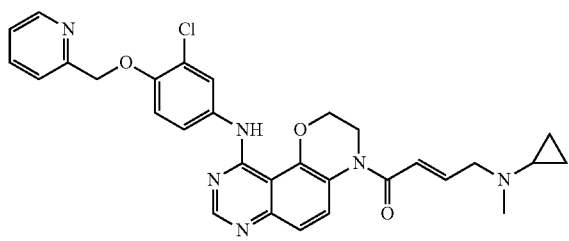 [SMILES: CN(C/C=C/C(=O)N1CCOc2c1ccc1ncnc(Nc3ccc(OCc4ccccn4)c(Cl)c3)c21)C1CC1]

or the pharmaceutically acceptable salt thereof.

12. The compound according to claim 8 having the following structure:

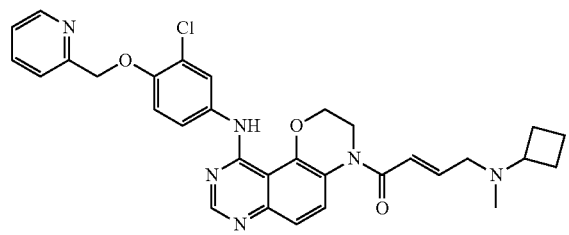 [SMILES: CN(C/C=C/C(=O)N1CCOc2c1ccc1ncnc(Nc3ccc(OCc4ccccn4)c(Cl)c3)c21)C1CCC1]

or the pharmaceutically acceptable salt thereof.

13. The compound according to claim 8 having the following structure:

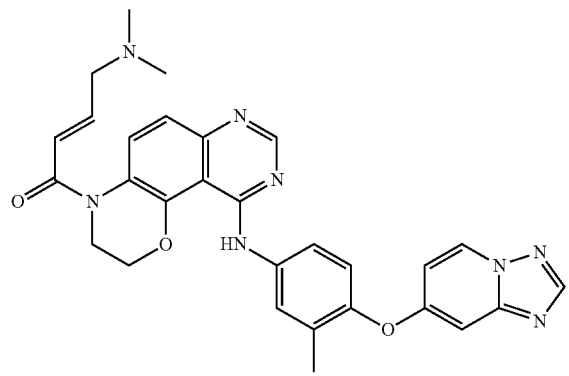 [SMILES: Cc1cc(Nc2ncnc3ccc4c(c23)OCCN4C(=O)/C=C/CN(C)C)ccc1Oc1ccn2ncnc2c1]

or the pharmaceutically acceptable salt thereof.

14. A pharmaceutical composition for treating diseases related to tyrosine kinases EGFR, HER2, HER3 or HER4, which consists of the compound of Formula (I) or a pharmaceutically acceptable salt, diastereomer, enantiomer, hydrate, or solvate thereof according to claim 1 and pharmaceutically acceptable carrier(s) or excipient(s).

15. A pharmaceutical composition comprising the compound of Formula (I) or a pharmaceutically acceptable salt, diastereomer, enantiomer, hydrate, or solvate thereof according to claim 1 as an active ingredient, one or more other therapeutic agents, and one or more pharmaceutically acceptable carriers or excipients.

16. A compound of Formula (I), or a diastereomer, enantiomer, hydrate, solvate, or pharmaceutically acceptable salt thereof:

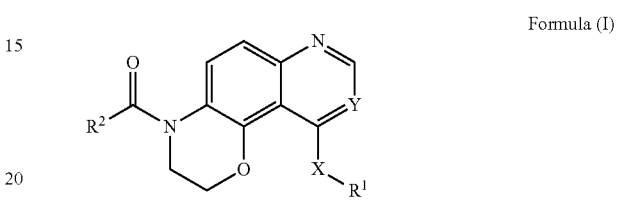

Formula (I)

in the formula (I),
X is O, or NH;
Y is N or C—Z, wherein Z is —H or —CN;
$R^1$ is

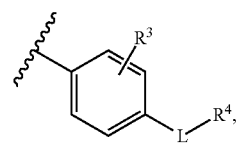

$R^3$ is —H, halogen, $C_1$-$C_3$ alkyl, $C_1$-$C_3$ alkoxy, $C_1$-$C_3$ alkyl substituted by halogen or $C_1$-$C_3$ alkoxy substituted by halogen;

L is

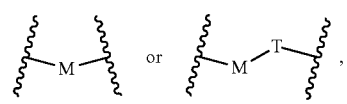

M is O or S;
T is linear $C_1$-$C_3$ alkylene, or linear $C_1$-$C_3$ alkylene independently substituted by $R^5$ and $R^6$, respectively;
$R^5$ and $R^6$ are each —H, halogen, $C_1$-$C_3$ alkyl, or $C_1$-$C_3$ alkyl substituted by halogen;
$R^4$ is substituted or unsubstituted fused heteroaryl, the substituted fused heteroaryl is substituted by 1-3 identical or different $R^7$, the fused ring heteroaryl group is a heteroaryl group containing 1-3 heteroatoms selected from N, O or S;
$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl;

$R^2$ is

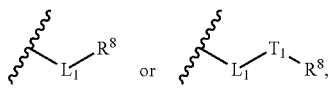

$L_1$ is selected from:

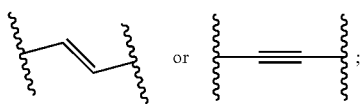

$T_1$ is linear $C_1$-$C_8$ alkylene, or linear $C_1$-$C_8$ alkylene independently substituted by $R^9$ and $R^{10}$, respectively;

$R^9$ and $R^{10}$ are each independently —H, or $C_1$-$C_3$ alkyl;

$R^8$ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —NR$^{11}$R$^{12}$;

$R^{11}$ and $R^{12}$ are each independently —H, $C_1$-$C_6$ alkyl, $C_3$-$C_6$ cycloalkyl, $C_1$-$C_6$ alkyl substituted by hydroxy or $C_1$-$C_6$ alkyl substituted by $C_1$-$C_3$ alkoxy;

the 4- to 7-membered heterocyclyl is a heterocyclyl containing 1-2 heteroatoms selected from N, O or S, the heterocyclyl is unsubstituted or substituted by any one or two of the group consisting of: $C_1$-$C_3$ alkyl, aldehyde group, $C_1$-$C_4$ alkylacyl, aminoacyl, aminoacyl wherein the amino is substituted with mono- or di-$C_1$-$C_3$ alkyl, $C_1$-$C_3$ alkylsulfonyl, $C_1$-$C_3$ alkylsulfinyl, hydroxy, halogen, $C_1$-$C_3$ hydroxyalkyl, or $C_1$-$C_3$ haloalkyl, or the sulfur in the heterocycle is oxidized by one to two oxygen atoms.

17. The compound, or a diastereomer, enantiomer, hydrate, solvate, or pharmaceutically acceptable salt thereof according to claim 16, wherein:

$R^1$ is

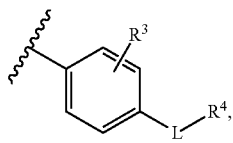

$R^3$ is —H, fluorine, chlorine, bromine, methyl, ethyl, methoxy, ethoxy, trifluoromethyl or trifluoromethoxy;

L is

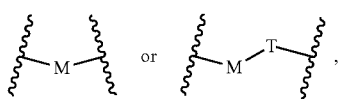

M is O or S;

T is linear $C_1$-$C_2$ alkylene, or linear $C_1$-$C_2$ alkylene independently substituted by $R^5$ and $R^6$, respectively;

$R^5$ and $R^6$ are each independently —H, —F, methyl, ethyl or trifluoromethyl;

$R^4$ is unsubstituted or substituted

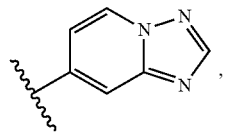 [SMILES: *c1ccn2ncnc2c1]

the group is substituted by 1-3 identical or different $R^7$, $R^7$ is —H, —F, —Cl, —Br, —CF$_3$, —OCF$_3$, amino, hydroxy, cyano, methylthio, ethylthio, propylthio, isopropylthio, methylamino, ethylamino, dimethylamino, diethylamino, cyclopropyl, cyclobutyl, methyl, ethyl, propyl, isopropyl, methoxy, ethoxy, propoxy, isopropoxy, hydroxymethyl, hydroxyethyl, hydroxypropyl, methylaminomethyl, methylaminoethyl, methylaminopropyl, dimethylaminomethyl, dimethylaminoethyl, dimethylaminopropyl, methoxymethyl, methoxyethyl, methoxypropyl, ethoxymethyl, ethoxyethyl, ethoxypropyl, methoxyethoxy, methoxypropoxy, ethoxyethoxy, ethoxypropoxy, methylaminoethoxy, methylaminopropoxy, ethylaminoethoxy, ethylaminopropoxy, dimethylaminoethoxy, dimethylaminopropoxy, diethylaminoethoxy, or diethylaminopropoxy.

18. The compound, or a diastereomer, enantiomer, hydrate, solvate, or pharmaceutically acceptable salt thereof according to claim 5, wherein:

in the formula (I),

X is NH;

Y is N;

$R^1$ is

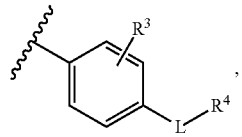

$R^3$ is —H, halogen, $C_1$-$C_3$ alkyl, or $C_1$-$C_3$ alkyl substituted by halogen;

L is

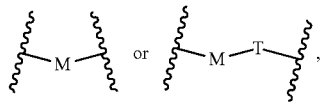

M is O or S;

T is linear $C_1$-$C_3$ alkylene;

$R^4$ is substituted or unsubstituted fused heteroaryl, wherein the fused ring heteroaryl group is a heteroaryl group containing 1-3 heteroatoms selected from N, O or S;

$R^2$ is

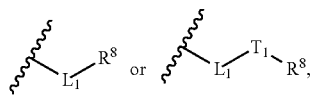

L₁ is selected from:

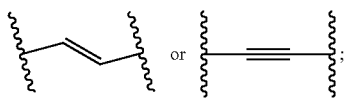

T₁ is linear $C_1$-$C_8$ alkylene;
R⁸ is —NR¹¹R¹²;
R¹¹ and R¹² are each independently —H, or $C_1$-$C_6$ alkyl.

19. A compound of Formula (I), or a diastereomer, enantiomer, hydrate, solvate, or pharmaceutically acceptable salt thereof:

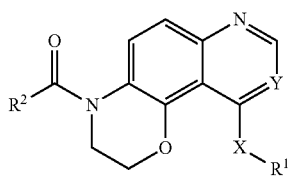

Formula (I)

in the formula (I),
X is O, or NH;
Y is N or C—Z, wherein Z is —H or —CN;
R¹ is

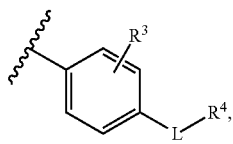

R³ is —H, halogen, $C_1$-$C_3$ alkyl, $C_1$-$C_3$ alkoxy, $C_1$-$C_3$ alkyl substituted by halogen or $C_1$-$C_3$ alkoxy substituted by halogen;
L is

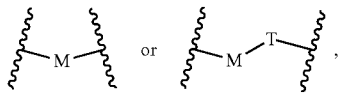

M is O or S;
T is linear $C_1$-$C_3$ alkylene, or linear $C_1$-$C_3$ alkylene independently substituted by R⁵ and R⁶, respectively;
R⁵ and R⁶ are each independently —H, halogen, $C_1$-$C_3$ alkyl, or $C_1$-$C_3$ alkyl substituted by halogen;
R⁴ is aryl, 5- to 6-membered heteroaryl, aryl substituted by 1-3 identical or different R⁷, or 5- to 6-membered heteroaryl substituted by 1-3 identical or different R⁷, wherein the heteroaryl group is a heteroaryl group containing 1-3 heteroatoms selected from N, O or S;
R⁷ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_1$-$C_6$ alkyl, or unsubstituted or substituted $C_1$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_1$-$C_6$ alkoxy is halogen, $C_1$-$C_3$ alkoxy, or amino substituted with mono- or di-$C_1$-$C_3$ alkyl;

R² is

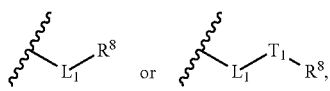

L₁ is selected from

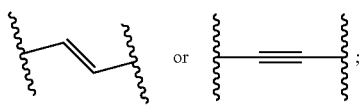

T₁ is linear $C_1$-$C_8$ alkylene, or linear $C_1$-$C_8$ alkylene independently substituted by R⁹ and R¹⁰, respectively;
R⁹ and R¹⁰ are each independently —H, or $C_1$-$C_3$ alkyl;
R⁸ is —H, hydroxy, $C_1$-$C_3$ alkyl, $C_3$-$C_7$ cycloalkyl, $C_1$-$C_3$ alkoxy, $C_1$-$C_3$ alkylthio, 4- to 7-membered heterocyclyl or —NR¹¹R¹²;
R¹¹ and R¹² are each independently —H, $C_1$-$C_6$ alkyl, $C_3$-$C_6$ cycloalkyl, $C_1$-$C_6$ alkyl substituted by hydroxyl or $C_1$-$C_6$ alkyl substituted by $C_1$-$C_3$ alkoxy;
the 4- to 7-membered heterocyclyl is a heterocyclyl containing 1-2 heteroatoms selected from N, O or S, the heterocyclyl is unsubstituted or substituted by any one or two of the group consisting of: $C_1$-$C_3$ alkyl, hydroxy, halogen, $C_1$-$C_3$ hydroxyalkyl, or $C_1$-$C_3$ haloalkyl.

20. A method of treating cancer and autoimmune diseases associated with tyrosine kinases EGFR, HER2, HER3 or HER4 in a subject, comprising administering to the subject a therapeutically effective amount of a compound of Formula (I) or a pharmaceutically acceptable salt, diastereomer, enantiomer, hydrate, or solvate thereof according to claim 1, wherein the cancer and autoimmune diseases include ocular fundus disease, xerophthalmia, psoriasis, leucoderma, dermatitis, alopecia areata, rheumatoid arthritis, colitis, multiple sclerosis, systemic lupus erythematosus, Crohn's disease, atherosclerosis, pulmonary fibrosis, liver fibrosis, myelofibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, and cholangiocarcinoma.

21. A compound represented by formula (VIII),

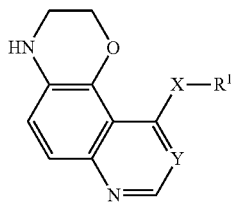

(VIII)

wherein
X is O, or NH;
Y is N or C—Z, wherein Z is —H or —CN;

$R^1$ is

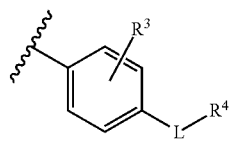

$R^3$ is —H, halogen, $C_1$-$C_3$ alkyl, $C_1$-$C_3$ alkoxy, $C_1$-$C_3$ alkyl substituted by halogen, or $C_1$-$C_3$ alkoxy substituted by halogen;

L is

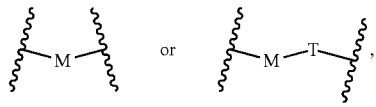

M is O or S;

T is linear $C_1$-$C_3$ alkylene, or linear $C_1$-$C_3$ alkylene independently substituted by $R^5$ and $R^6$, respectively;

$R^5$ and $R^6$ are independently —H, halogen, $C_1$-$C_3$ alkyl, or $C_1$-$C_3$ substituted by halogen;

$R^4$ is aryl, 5- to 6-membered heteroaryl, aryl substituted by 1-3 identical or different $R^7$, or 5- to 6-membered heteroaryl substituted by 1-3 identical or different $R^7$, wherein the heteroaryl group is a heteroaryl group containing 1-3 heteroatoms selected from N, O or S;

$R^7$ is —H, halogen, amino, hydroxy, cyano, $C_1$-$C_3$ alkylthio, amino substituted with mono- or di-$C_1$-$C_3$ alkyl, $C_3$-$C_4$ cycloalkyl, unsubstituted or substituted $C_3$-$C_6$ alkyl, or unsubstituted or substituted $C_3$-$C_6$ alkoxy, wherein the substituent of the substituted $C_1$-$C_6$ alkyl is halogen, hydroxy, amino substituted with mono- or di-$C_1$-$C_3$ alkyl, or $C_1$-$C_3$ alkoxy, and wherein the substituent of the substituted $C_3$-$C_6$ alkoxy is halogen, $C_1$-$C_3$ alkoxy, or amino substituted with mono- or di-$C_1$-$C_3$ alkyl.

22. A compound having the following structure:

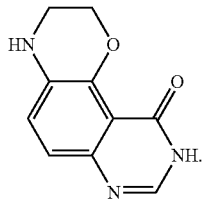 [SMILES: O=c1[nH]cnc2ccc3c(c12)OCCN3]

* * * * *

UNITED STATES PATENT AND TRADEMARK OFFICE
CERTIFICATE OF CORRECTION

PATENT NO. : 11,548,900 B2
APPLICATION NO. : 16/978158
DATED : January 10, 2023
INVENTOR(S) : Qiang Zhang et al.

It is certified that error appears in the above-identified patent and that said Letters Patent is hereby corrected as shown below:

In the Claims

Column 153, Claim 8, Line 20: delete "(3" and replace with --((3--.

Column 158, Claim 18, Line 29: delete "claim 5" and replace with --claim 16--.

Column 161, Claim 21, Line 26: insert --alkyl-- after "$C_1$-$C_3$".

Column 162, Claim 21, Line 8: delete "$C_3$-$C_6$ alkyl" and replace with --$C_1$-$C_6$ alkyl--; also delete "$C_3$-$C_6$ alkoxy" and replace with --$C_1$-$C_6$ alkoxy--.

Column 162, Claim 21, Line 12: delete "$C_3$-$C_6$ alkoxy" and replace with --$C_1$-$C_6$ alkoxy--.

Signed and Sealed this
Sixteenth Day of January, 2024

Katherine Kelly Vidal
*Director of the United States Patent and Trademark Office*